United States Patent
Yang et al.

(10) Patent No.: US 9,920,049 B2
(45) Date of Patent: *Mar. 20, 2018

(54) DIHYDROQUINOLIZINONES FOR THE TREATMENT AND PROPHYLAXIS OF HEPATITIS B VIRUS INFECTION

(71) Applicant: Hoffmann-La Roche Inc., Little Falls, NJ (US)

(72) Inventors: Song Yang, Shanghai (CN); Xingchun Han, Shanghai (CN); Zhanguo Wang, Shanghai (CN)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,343

(22) Filed: Nov. 11, 2016

(65) Prior Publication Data

US 2017/0057952 A1    Mar. 2, 2017

Related U.S. Application Data

(63) Continuation of application No. PCT/EP2015/060284, filed on May 11, 2015.

(30) Foreign Application Priority Data

May 13, 2014  (WO) ............... PCT/CN2014/077354
Mar. 18, 2015  (WO) ............... PCT/CN2015/074462

(51) Int. Cl.
C07D 455/06    (2006.01)
(52) U.S. Cl.
CPC .................. C07D 455/06 (2013.01)
(58) Field of Classification Search
CPC ................................................. C07D 455/06
(Continued)

(56) References Cited

U.S. PATENT DOCUMENTS 9,458,153 B2 * 10/2016 Han ..................... C07D 455/06
9,637,485 B2 *  5/2017 Han ..................... C07D 471/04

FOREIGN PATENT DOCUMENTS

JP     60-197684     * 10/1985
JP     S60197684 A    10/1985
(Continued)

OTHER PUBLICATIONS

JP 60-197684 A, 1986, CAPLUS Abstract, AN 1986:148761.*
(Continued)

*Primary Examiner* — Shengjun Wang
(74) *Attorney, Agent, or Firm* — Brian L. Buckwalter

(57) ABSTRACT

The invention provides novel compounds having the general formula:

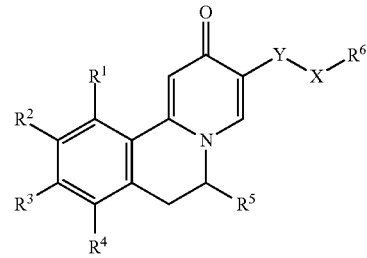

wherein $R^1$, $R^2$, $R^3$, $R^4$, $R^5$, $R^6$, X and Y are as described in the description and in the claims, as well as or pharmaceutically acceptable salts, or enantiomers, or diastereomers thereof. The invention also contains compositions including the compounds and methods of using the compounds.

16 Claims, 1 Drawing Sheet

X-ray structure of (6S)-6-ethyl-9,10-dimethoxy-2-oxo-6,7-dihydrobenzo[a]quinolizine-3-carboxylic acid [the (S)-enantiomer intermediate of step 6 in Example 31]

(58) Field of Classification Search
USPC .......................................... 546/95; 514/294
See application file for complete search history.

(56) References Cited

FOREIGN PATENT DOCUMENTS

| WO | 2015/113990 A1 | 6/2015 |
| WO | WO 2015/173164 | * 11/2015 |

OTHER PUBLICATIONS

Chemical Abstract, RN 100891-45-0, 1986.*
Chemical Abstract, RN 100891-44-9, 1986.*
Chemical Abstract, RN 100891-42-7, 1986.*
Chemical Abstract, RN 100891-41-6, 1986.*
JP 60-197684 A Machine translation.*
Acs et al., Proc Natl Acad Sci USA 84:4641-4644 ( 1987).
Bastin et al., "Salt selection and optimisation procedures for pharmaceutical new chemical entities" Organic Process Res & Dev 4:427-435 ( 2000).
Belloni et al., "IFN-α inhibits HBV transcription and replication in cell culture and in humanized mice by targeting the epigenetic regulation of the nuclear cccDNa minichromosome" J Clin Inves 122(2):529-537 (Feb. 2012).
Buster et al., "Peginterferon alpha-2b is safe and effective in HBeAg-Positive chronic hepatitis B patients with advanced fibrosis" Hepatology 46:388-394 ( 2007).
Fecik et al., "Chiral DNA gyrase inhibitors. 3. Probing the chiral preference of the active site of DNA gyrase. Synthesis of 10-fluoro-6-methyl-6,7-dihydro-9-piperazinyl-2H-benzo[a]quinolizin-20-one-3-carboxylic acid analogues" J Med Chem 48(4):1229-1236 ( 2005).
Fisicaro et al., "Antiviral intrahepatic T-cell responses can be restored by blocking programmed death-1 pathway in chronic hepatitis B" Gastroenterology 138:682-693 ( 2010).
Geng et al., "Small-molecule inhibitors for the treatment of hepatitis B virus documented in patents" Mini Reviews in Medicinal Chemistry 13(5):749-776 (Apr. 1, 2013).
Janssen et al., "Pegylated interferon alfa-2b alone or in combination with lamivudine for HBeAg-positive chronic hepatitis B: a randomised trial" Lancet 365:123-129 (Jan. 8, 2005).
Kondo et al., "Hepatitis B surface antigen could contribute to the immunopathogenesis of hepatitis B virus infection" ISRN Gastroenterology (Article ID 935295), 2013.
Kondo et al., "Recovery of Functional Cytotoxic T Lymphocytes During Lamivudine Therapy by Acquiring Multi-Specificity" J Med Virol 74:425-433 ( 2004).
Kumar et al., "Hepatitis B virus regulatory HBx protein binds to adaptor protein IPS-1 and inhibits the activation of beta interferon" J Virol 85(2):987-995 (Jan. 2011).
Lambert et al., "Posttranslational N-glycosylation of the hepatitis B virus large envelope protein" Virol J 4( Suppl 1-9):45 (May 2007).
Locarnini, S., "Molecular virology and the development of resistant mutants: implications for therapy" Semin Liver Dis 25( Suppl 1):9-19 ( 2005).
Mao et al., "Indoleamine 2,3-dioxygenase mediates the antiviral effect of gagamma interferon against hepatitis B virus in human hepatocyte-derived cells" J Virol 85(2):1048-1057 (Jan. 2011).
Mao et al., "Inhibition of hepatitis B virus replication by the host zinc finger antiviral protein" PLoS Pathogens 9(7 Suppl 1-18):e1003494 (Jul. 2013).
Marcellin et al., "Peginterferon alfa-2a alone, lamivudine alone, and the two in combination in patients with HBeAg-negative chronic hepatitis B" New E J Med 351(12):1206-1217 (Sep. 16, 2004).
N H Georgopapadakou et al., "Monocyclic and tricyclic analogs of quinolones: mechanism of action" Antimicrob Agents CH 31(4):614 (Apr. 1987).
Nayersina et al., "HLA A2 restricted cytotoxic T lymphocyte responses to multiple hepatitis B surface atigen epitopes during hepatitis B virus infection" J Immunol 150:4659-4671 (May 15, 1993).
Op den Brouw et al., "Hepatitis B virus surface antigen impairs myeloid dendritic cell function: a possible immune escape mechanism of hepatitis B virus" Immunol 126:280-290 ( 2008).
Quasdorff et al., "Control of hepatitis B virus at the level of transcription" J Viral Hepatitis 17:527-536 ( 2010).
Schulze et al., "Hepatitis B virus infection initiates with a large surface protein-dependent binding to heparan sulfate proteoglycans" Hepatology 46:1759-1768 ( 2007).
Shi et al., "Hepatitis B virus suppresses the functional interaction between natural killer cells and plasmacytoid dendritic cells" J Viral Hepatitis 19:e26-e33 ( 2012).
Wieland et al., "Stealth and cunning: hepatitis B and hepatitis C viruses" J Virol 79(15):9369-9380 (Aug. 2005).
Woltman et al., "Heptatitis B virus lacks immune activating capacity, but actively inhibits plasmacytoid dendritic cell function" PLoS ONE 6(1 Suppl 1-14):e15324 (Jan. 2011).
Yan et al., "Molecular determinants of hepatitis B and D virus entry restriction in mouse sodium taurocholate cotransporting polypeptide" J Virol 87(14):7977-7991 (Jul. 2013).

* cited by examiner

X-ray structure of (6S)-6-ethyl-9,10-dimethoxy-2-oxo-6,7-dihydrobenzo[a]quinolizine-3-carboxylic acid [the (S)-enantiomer intermediate of step 6 in Example 31]
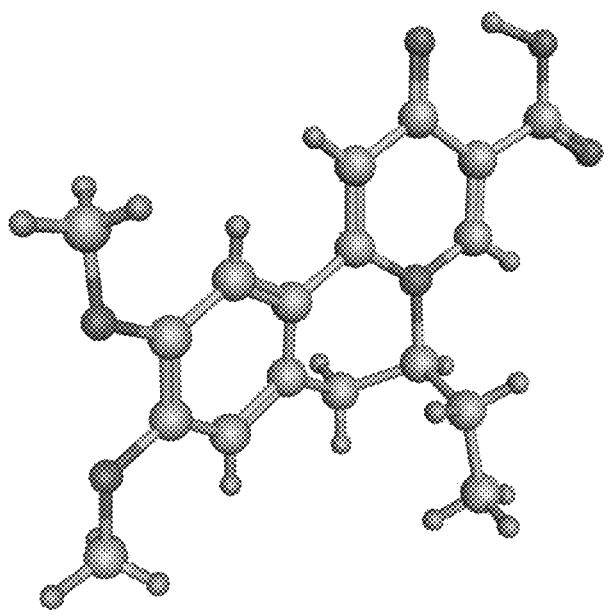

DIHYDROQUINOLIZINONES FOR THE TREATMENT AND PROPHYLAXIS OF HEPATITIS B VIRUS INFECTION

The present invention relates to organic compounds useful for therapy and/or prophylaxis in a mammal, and in particular to HBsAg (HBV Surface antigen) inhibitors useful for treating HBV infection.

FIELD OF THE INVENTION

The present invention relates to novel dihydroquinolizinones having pharmaceutical activity, their manufacture, pharmaceutical compositions containing them and their potential use as medicaments.

The present invention relates to compounds of formula I

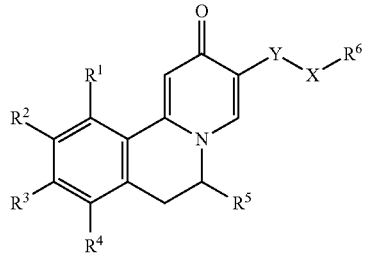

(I)

wherein $R^1$ to $R^6$ are as described below, or to pharmaceutically acceptable salts, or to enantiomers thereof.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins. The Pol ORF is the longest and the envelope ORF is located within it, while the X and core ORFs overlap with the Pol ORF. The lifecycle of HBV has two main events: 1) generation of closed circular DNA (cccDNA) from relaxed circular (RC DNA), and 2) reverse transcription of pregenomic RNA (pgRNA) to produce RC DNA. Prior to the infection of host cells, the HBV genome exists within the virion as RC DNA. It has been determined that HBV virions are able to gain entry into host cells by non-specifically binding to the negatively charged proteoglycans present on the surface of human hepatocytes (Schulze, A., P. Gripon & S. Urban. *Hepatology*, 46, (2007), 1759-68) and via the specific binding of HBV surface antigens (HBsAg) to the hepatocyte sodium-taurocholate cotransporting polypeptide (NTCP) receptor (Yan, H. et al. *J Virol*, 87, (2013), 7977-91). Once the virion has entered the cell, the viral cores and the encapsidated RC DNA are transported by host factors, via a nuclear localization signal, into the nucleus through the Impβ/Impα nuclear transport receptors. Inside the nucleus, host DNA repair enzymes convert the RC DNA into cccDNA. cccDNA acts as the template for all viral mRNAs and as such, is responsible for HBV persistence in infected individuals. The transcripts produced from cccDNA are grouped into two categories; Pregenomic RNA (pgRNA) and subgenomic RNA. Subgenomic transcripts encode for the three envelopes (L, M and S) and X proteins, and pgRNA encodes for Pre-Core, Core, and Pol proteins (Quasdorff, M. & U. Protzer. *J Viral Hepat*, 17, (2010), 527-36) Inhibition of HBV gene expression or HBV RNA synthesis leads to the inhibition of HBV viral replication and antigens production (Mao, R. et al. *PLoS Pathog*, 9, (2013), e1003494; Mao, R. et al. *J Virol*, 85, (2011), 1048-57). For instance, IFN-α was shown to inhibit HBV replication and viral HBsAg production by decreasing the transcription of pgRNA and subgenomic RNA from the HBV covalently closed circular DNA (cccDNA) minichromosome. (Belloni, L. et al. *J Clin Invest*, 122, (2012), 529-37; Mao, R. et al. *J Virol*, 85, (2011), 1048-57). All HBV viral mRNAs are capped and polyadenylated, and then exported to the cytoplasm for translation. In the cytoplasm, the assembly of new virons is initiated and nascent pgRNA is packaged with viral Pol so that reverse transcription of pgRNA, via a single stranded DNA intermediate, into RC DNA can commence. The mature nucleocapsids containing RC DNA are enveloped with cellular lipids and viral L, M, and S proteins and then the infectious HBV particles are then released by budding at the intracellular membrane (Locarnini, S. *Semin Liver Dis*, (2005), 25 Suppl 1, 9-19). Interestingly, non-infectious particles are also produced that greatly outnumber the infectious virions. These empty, enveloped particles (L, M and S) are referred to as subviral particles. Importantly, since subviral particles share the same envelope proteins and as infectious particles, it has been surmised that they act as decoys to the host immune system and have been used for HBV vaccines. The S, M, and L envelope proteins are expressed from a single ORF that contains three different start codons. All three proteins share a 226aa sequence, the S-domain, at their C-termini. M and L have additional pre-S domains, Pre-S2 and Pre-S2 and Pre-S1, respectively. However, it is the S-domain that has the HBsAg epitope (Lambert, C. & R. Prange. *Virol J*, (2007), 4, 45).

The control of viral infection needs a tight surveillance of the host innate immune system which could respond within minutes to hours after infection to impact on the initial growth of the virus and limit the development of a chronic and persistent infection. Despite the available current treatments based on IFN and nucleos(t)ide analogues, the Hepatitis B virus (HBV) infection remains a major health problem worldwide which concerns an estimated 350 million chronic carriers who have a higher risk of liver cirrhosis and hepatocellular carcinoma.

The secretion of antiviral cytokines in response to HBV infection by the hepatocytes and/or the intra-hepatic immune cells plays a central role in the viral clearance of infected liver. However, chronically infected patients only display a weak immune response due to various escape strategies adopted by the virus to counteract the host cell recognition systems and the subsequent antiviral responses.

Many observations showed that several HBV viral proteins could counteract the initial host cellular response by interfering with the viral recognition signaling system and subsequently the interferon (IFN) antiviral activity. Among these, the excessive secretion of HBV empty subviral particles (SVPs, HBsAg) may participate to the maintenance of the immunological tolerant state observed in chronically infected patients (CHB). The persistent exposure to HBsAg and other viral antigens can lead to HBV-specific T-cell deletion or to progressive functional impairment (Kondo et al. *Journal of Immunology* (1993), 150, 4659-4671; Kondo et al. *Journal of Medical Virology* (2004), 74, 425-433; Fisicaro et al. *Gastroenterology*, (2010), 138, 682-93;). Moreover HBsAg has been reported to suppress the function of immune cells such as monocytes, dendritic cells (DCs) and natural killer (NK) cells by direct interaction (Op den Brouw et al. *Immunology*, (2009b), 126, 280-9; Woltman et al. *PLoS One*, (2011), 6, e15324; Shi et al. *J Viral Hepat*. (2012), 19, e26-33; Kondo et al. *ISRN Gasteroenterology*, (2013), Article ID 935295).

HBsAg quantification is a significant biomarker for prognosis and treatment response in chronic hepatitis B. However the achievement of HBsAg loss and seroconversion is rarely observed in chronically infected patients but remains the ultimate goal of therapy. Current therapy such as Nucleos(t)ide analogues are molecules that inhibit HBV DNA synthesis but are not directed at reducing HBsAg level. Nucleos(t)ide analogs, even with prolonged therapy, have demonstrated rates of HBsAg clearance comparable to those observed naturally (between −1%-2%) (Janssen et al. *Lancet*, (2005), 365, 123-9; Marcellin et al. *N. Engl. J. Med.*, (2004), 351, 1206-17; Buster et al. *Hepatology*, (2007), 46, 388-94). Therefore, targeting HBsAg together with HBV DNA levels in CHB patients may significantly improve CHB patient immune reactivation and remission (Wieland, S. F. & F. V. Chisari. *J Virol*, (2005), 79, 9369-80; Kumar et al. *J Virol*, (2011), 85, 987-95; Woltman et al. *PLoS One*, (2011), 6, e15324; Op den Brouw et al. *Immunology*, (2009b), 126, 280-9).

SUMMARY OF THE INVENTION

The present invention relates to novel compounds of formula (I)

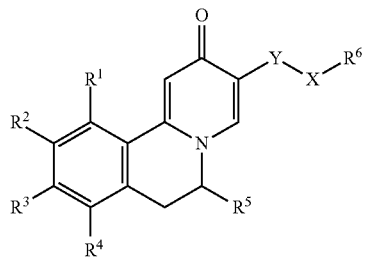

(I)

wherein
X is oxygen or N—$R^7$;
Y is $CH_2$ or $C(O)$;
$R^1$ is hydrogen, halogen, $C_{1-6}$alkyl, or $C_{1-6}$alkoxy;
$R^2$ is hydrogen; halogen; $C_{1-6}$alkyl, which is unsubstituted or once or more times substituted by fluoro; or $C_{1-6}$alkoxy;
$R^3$ is hydrogen; halogen; $C_{1-6}$alkyl, which is unsubstituted or once or more times substituted by fluoro; cyano; morpholinyl; pyrrolidinyl; or $R^8$—O—, wherein $R^8$ is $C_{1-6}$alkyl, which is unsubstituted or once or more times substituted by fluoro, $C_{1-6}$alkoxy, $C_{1-6}$alkylsulfonyl, cyano, $C_{3-7}$cycloalkyl, $C_{1-6}$alkylamino, di$C_{1-6}$alkylamino, hydroxy, phenyl, pyrrolidinyl or tetrahydropyranyl;
$R^4$ is hydrogen, halogen or $C_{1-6}$alkyl;
$R^5$ is hydrogen; $C_{1-6}$alkyl, which is unsubstituted or once or more times substituted by fluoro; $C_{1-6}$alkoxy; $C_{3-7}$cycloalkyl or $C_{3-7}$cycloalkyl-$C_xH_{2x}$—;
$R^6$ is hydrogen; $C_{1-6}$alkylsulfonyl; hydroxyl; 1H-tetrazol-5-yl; $C_{1-6}$alkyl, which is unsubstituted or once or more times substituted by fluoro, $C_{3-7}$cycloalkyl, carboxyl-$C_xH_{2x}$—, phenyl, hydroxy, $C_{1-6}$alkoxy, amino, $C_{1-6}$alkylamino or di$C_{1-6}$alkylamino;
$R^7$ is hydrogen or $C_{1-6}$alkyl;
or $R^6$ and $R^7$, together with the nitrogen to which they are attached, form pyrrolidinyl, piperidinyl, morpholinyl, which is unsubstituted or once or two times substituted by carboxyl;
or pharmaceutically acceptable salts, enantiomers or diastereomers thereof.

The invention is also relates to their manufacture, medicaments based on a compound in accordance with the invention and their production as well as the use of compounds of formula I as HBsAg inhibitors. Accordingly, the compounds of formula I are useful for the treatment or prophylaxis of HBV infection.

DETAILED DESCRIPTION OF THE INVENTION

Unless otherwise defined, all technical and scientific terms used herein have the same meaning as commonly understood by one of ordinary skill in the art to which this invention belongs. Furthermore, the following definitions are set forth to illustrate and define the meaning and scope of the various terms used to describe the invention.

Definitions

As used herein, the term "$C_{1-6}$alkyl" alone or in combination signifies a saturated, linear- or branched chain alkyl group containing 1 to 6, particularly 1 to 4 carbon atoms, for example methyl, ethyl, propyl, isopropyl, 1-butyl, 2-butyl, tert-butyl and the like. Particular "$C_{1-6}$alkyl" groups are methyl, ethyl, isopropyl and tert-butyl.

The term "$C_xH_{2x}$" alone or in combination signifies a saturated, linear- or branched chain alkyl group containing 1 to 6, particularly 1 to 4 carbon atoms.

The term "$C_{3-7}$cycloalkyl", alone or in combination, refers to a saturated carbon ring containing from 3 to 7 carbon atoms, particularly from 3 to 6 carbon atoms, for example, cyclopropyl, cyclobutyl, cyclopentyl, cyclohexyl, cycloheptyl and the like. Particular "$C_{3-7}$cycloalkyl" groups are cyclopropyl, cyclopentyl and cyclohexyl.

The term "$C_{1-6}$alkoxy" alone or in combination signifies a group $C_{1-6}$alkyl-O—, wherein the "$C_{1-6}$alkyl" is as defined above; for example methoxy, ethoxy, propoxy, iso-propoxy, n-butoxy, iso-butoxy, 2-butoxy, tert-butoxy and the like. Particular "$C_{1-6}$alkoxy" groups are methoxy and ethoxy and more particularly methoxy.

The term "amino", alone or in combination, refers to primary (—$NH_2$), secondary (—NH—) or tertiary amino

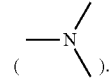

The term "carboxy" or "carboxyl" alone or in combination refers to the group —COOH.

The term "cyano" alone or in combination refers to the group —CN.

The term "halogen" means fluorine, chlorine, bromine or iodine. Halogen is particularly fluorine, chlorine or bromine.

The term "hydroxy" alone or in combination refers to the group —OH.

The term "1H-tetrazol-5-yl" alone or in combination refers to the group

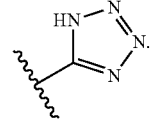 [SMILES: *c1nnn[nH]1]

The term "sulfonyl" alone or in combination refers to the group —$S(O)_2$—.

The term "$C_{1-6}$alkylamino" refers to amino group as defined above wherein at least one of the hydrogen atoms of the amino group is replaced by a $C_{1-6}$alkyl group.

The term "$C_{1-6}$alkylsulfonyl" refers to a group $C_{1-6}$alkyl-$S(O)_2$—, wherein the "$C_{1-6}$alkyl" is as defined above.

The term "compound(s) of this invention" and "compound(s) of the present invention" refers to compounds of formula I and stereoisomers, solvates or salts thereof (e.g., pharmaceutically acceptable salts).

The term "substituent" denotes an atom or a group of atoms replacing a hydrogen atom on the parent molecule.

The term "enantiomer" denotes two stereoisomers of a compound which are non-superimposable mirror images of one another.

The term "diastereomer" denotes a stereoisomer with two or more centers of chirality and whose molecules are not mirror images of one another.

The compounds according to the present invention may exist in the form of their pharmaceutically acceptable salts.

The term "pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et al., Organic Process Research & Development 2000, 4, 427-435; or in Ansel, H., et al., In: Pharmaceutical Dosage Forms and Drug Delivery Systems, 6th ed. (1995), pp. 196 and 1456-1457. Particular are the sodium salts of the compounds of formula I.

Compounds of the general formula I which contain one or several chiral centers can either be present as racemates, diastereomeric mixtures, or optically active single isomers. The racemates can be separated according to known methods into the enantiomers. Particularly, diastereomeric salts which can be separated by crystallization are formed from the racemic mixtures by reaction with an optically active acid such as e.g. D- or L-tartaric acid, mandelic acid, malic acid, lactic acid or camphorsulfonic acid.

Inhibitors of HBsAg

The present invention relates to (i) a compound of formula (I):

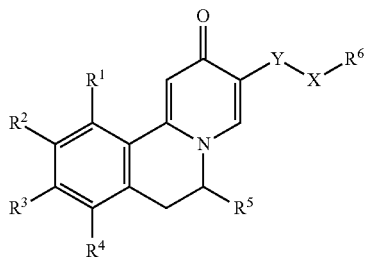

(I)

wherein
X is oxygen or N—$R^7$;
Y is $CH_2$ or C(O);
$R^1$ is hydrogen, halogen, $C_{1-6}$alkyl, or $C_{1-6}$alkoxy;
$R^2$ is hydrogen; halogen; $C_{1-6}$alkyl, which is unsubstituted or once or more times substituted by fluoro; or $C_{1-6}$alkoxy;
$R^3$ is hydrogen; halogen; $C_{1-6}$alkyl, which is unsubstituted or once or more times substituted by fluoro; cyano; morpholinyl; pyrrolidinyl; or $R^8$—O—, wherein $R^8$ is $C_{1-6}$alkyl, which is unsubstituted or once or more times substituted by fluoro, $C_{1-6}$alkoxy, $C_{1-6}$alkylsulfonyl, cyano, $C_{3-7}$cycloalkyl, $C_{1-6}$alkylamino, $diC_{1-6}$alkylamino, hydroxy, phenyl, pyrrolidinyl or tetrahydropyranyl;
$R^4$ is hydrogen, halogen or $C_{1-6}$alkyl;
$R^5$ is hydrogen; $C_{1-6}$alkyl, which is unsubstituted or once or more times substituted by fluoro; $C_{1-6}$alkoxy; $C_{3-7}$cycloalkyl or $C_{3-7}$cycloalkyl-$C_xH_{2x}$—;
$R^6$ is hydrogen; $C_{1-6}$alkylsulfonyl; hydroxyl; 1H-tetrazol-5-yl; $C_{1-6}$alkyl, which is unsubstituted or once or more times substituted by fluoro, $C_{3-7}$cycloalkyl, carboxyl-$C_xH_{2x}$—, phenyl, hydroxy, $C_{1-6}$alkoxy, amino, $C_{1-6}$alkylamino or $diC_{1-6}$alkylamino;
$R^7$ is hydrogen or $C_{1-6}$alkyl;
or $R^6$ and $R^7$, together with the nitrogen to which they are attached, form pyrrolidinyl, piperidinyl, morpholinyl, which is unsubstituted or once or two times substituted by carboxyl;
or pharmaceutically acceptable salts, enantiomers or diastereomers thereof.

Another embodiment of present invention is (ii) a compound of formula (I), wherein
X is oxygen or N—$R^7$;
Y is $CH_2$ or C(O);
$R^1$ is hydrogen or halogen;
$R^2$ is hydrogen, halogen or $C_{1-6}$alkoxy;
$R^3$ is $R^8$—O—, wherein $R^8$ is $C_{1-6}$alkyl, which is unsubstituted or once or two times substituted by $C_{1-6}$alkoxy, $C_{3-7}$cycloalkyl or phenyl;
$R^4$ is hydrogen;
$R^5$ is $C_{1-6}$alkyl, which is unsubstituted or once or two times substituted by trifluoromethyl; or $C_{3-7}$cycloalkyl;
$R^6$ is hydrogen; $C_{1-6}$alkyl, which is unsubstituted or once or two times substituted by phenyl, hydroxy, $C_{1-6}$alkoxy, carboxy, $diC_{1-6}$alkyl amino; hydroxy; 1H-tetrazol-5-yl or $C_{1-6}$alkylsulfonyl;
$R^7$ is hydrogen or $C_{1-6}$alkyl;
or $R^6$ and $R^7$, together with the nitrogen to which they are attached, form pyrrolidinyl, piperidinyl, morpholinyl, which is unsubstituted or once or two times substituted by carboxyl;
or pharmaceutically acceptable salts, enantiomers or diastereomers thereof.

A further embodiment of present invention is (iii) a compound of formula (I), wherein
X is oxygen or N—$R^7$;
Y is $CH_2$ or C(O);
$R^1$ is hydrogen or chloro;
$R^2$ is hydrogen, methoxy or chloro;
$R^3$ is $R^8$—O—, wherein $R^8$ is methyl, ethyl, propyl, isobutyl, which is unsubstituted or once or two times substituted by methoxy, cyclopropyl or phenyl;
$R^4$ is hydrogen;
$R^5$ is ethyl, isopropyl, trifluoromethylmethyl, tert-butyl or cyclobutyl;
$R^6$ is hydrogen; methyl, ethyl, propyl, isopropyl or isobutyl, which is unsubstituted or once or two times substituted by phenyl, hydroxy, methoxy, carboxy, dimethylamino; hydroxy; 1H-tetrazol-5-yl or methylsulfonyl;
$R^7$ is hydrogen or methyl;
or $R^6$ and $R^7$, together with the nitrogen to which they are attached, form pyrrolidinyl, piperidinyl, morpholinyl, which is unsubstituted or once or two times substituted by carboxyl;
or pharmaceutically acceptable salts, enantiomers or diastereomers thereof.

Another embodiment of the present invention is (iv) a compound of formula (I) as defined above, or pharmaceutically acceptable salts, enantiomers or diastereomers thereof, wherein $R^1$ is hydrogen, and all remaining substituents have the significances given herein before.

Another embodiment of present invention is (v) a compound of formula (I) as defined above, or pharmaceutically acceptable salts, enantiomers or diastereomers thereof, wherein $R^2$ is $C_{1-6}$alkoxy or halogen, and all remaining substituents have the significances given herein before.

A further embodiment of present invention is (vi) a compound of formula (I) wherein $R^2$ is methoxy or chloro.

Another embodiment of present invention is (vii) a compound of formula (I) as defined above, or pharmaceutically acceptable salts, enantiomers or diastereomers thereof, wherein $R^3$ is $R^8$—O—, wherein $R^8$ is $C_{1-6}$alkyl, which is unsubstituted or once or two times substituted by $C_{1-6}$alkoxy or phenyl, and all remaining substituents have the significances given herein before.

A further embodiment of present invention is (viii) a compound of formula (I), wherein $R^3$ is $R^8$—O—, wherein $R^8$ is methyl or propyl, which is unsubstituted or once or two times substituted by methoxy or phenyl.

Another embodiment of present invention is (ix) a compound of formula (I) as defined above, or pharmaceutically acceptable salts, enantiomers or diastereomers thereof, wherein $R^5$ is $C_{1-6}$alkyl, which is unsubstituted or once or two times substituted by fluoro; or $C_{3-7}$cycloalkyl, and all remaining substituents have the significances given herein before.

A further embodiment of present invention is (x) a compound of formula (I) as defined above, or pharmaceutically acceptable salts, enantiomers or diastereomers thereof, wherein $R^5$ is ethyl or isopropyl, and all remaining substituents have the significances given herein before.

Another embodiment of present invention is (xi) a compound of formula (I) as defined above, or pharmaceutically acceptable salts, enantiomers or diastereomers thereof, wherein $R^6$ is hydrogen; methyl, ethyl, propyl, isopropyl or isobutyl, which is unsubstituted or once or two times substituted by phenyl, hydroxy, methoxy, carboxy, dimethylamino; hydroxy; 1H-tetrazol-5-yl or methylsulfonyl, and all remaining substituents have the significances given herein before.

Another embodiment of present invention is (xii) a compound of formula (I) as defined above, or pharmaceutically acceptable salts, enantiomers or diastereomers thereof, wherein $R^6$ and $R^7$, together with the nitrogen to which they are attached, form pyrrolidinyl, piperidinyl, morpholinyl, which is unsubstituted or once or two times substituted by carboxyl, and all remaining substituents have the significances given herein before.

Still another embodiment of present invention is (xiii) a compound of formula (I), wherein
X is oxygen, NH or N($C_{1-6}$alkyl);
Y is $CH_2$ or C(O);
$R^1$ is hydrogen;
$R^2$ is $C_{1-6}$alkoxy or halogen;
$R^3$ is $R^8$—O—,
wherein $R^8$ is $C_{1-6}$alkyl, which is unsubstituted or once substituted by phenyl or $C_{1-6}$alkoxy;
$R^4$ is hydrogen;
$R^5$ is $C_{1-6}$alkyl or $C_{3-7}$cycloalkyl;
$R^6$ is $C_{1-6}$alkylsulfonyl; 1H-tetrazol-5-yl; $C_{1-6}$alkyl, which is unsubstituted or once substituted by $C_{1-6}$alkoxy;
or pharmaceutically acceptable salts, or enantiomers thereof.

A further embodiment of present invention is (xiv) a compound of formula (I), wherein
X is oxygen, NH or N($CH_3$);
Y is $CH_2$ or C(O);
$R^1$ is hydrogen;
$R^2$ is methoxy or chloro;
$R^3$ is $R^8$—O—,
wherein $R^8$ is methyl, ethyl, propyl or isobutyl, which is unsubstituted or once substituted by phenyl or methoxy;
$R^4$ is hydrogen;
$R^5$ is ethyl, isopropyl, tert-butyl or cyclobutyl;
$R^6$ is methylsulfonyl; 1H-tetrazol-5-yl; methyl; or isopropyl, which is once substituted by methoxy; or pharmaceutically acceptable salts, or enantiomers thereof.

Particular compounds of formula (I) according to the invention are the following:
N-benzyl-9-benzyloxy-6-ethyl-10-methoxy-2-oxo-6,7-dihydrobenzo[a]quinolizine-3-carboxamide;
9-benzyloxy-6-ethyl-10-methoxy-N-methyl-2-oxo-6,7-dihydrobenzo[a]quinolizine-3-carboxamide;
9-benzyloxy-6-ethyl-10-methoxy-N-(2-methoxy-1-methylethyl)-2-oxo-6,7-dihydrobenzo[a]quinolizine-3-carboxamide;
9-benzyloxy-6-ethyl-10-methoxy-N-methylsulfonyl-2-oxo-6,7-dihydrobenzo[a]quinolizine-3-carboxamide;
9-benzyloxy-6-ethyl-10-methoxy-2-oxo-N-propyl-6,7-dihydrobenzo[a]quinolizine-3-carboxamide;
9-benzyloxy-6-ethyl-N-(2-hydroxyethyl)-10-methoxy-2-oxo-6,7-dihydrobenzo[a]quinolizine-3-carboxamide;
9-benzyloxy-6-ethyl-N-(2-hydroxy-1-methyl-ethyl)-10-methoxy-2-oxo-6,7-dihydrobenzo[a]quinolizine-3-carboxamide;
9-benzyloxy-N-[2-(dimethylamino)ethyl]-6-ethyl-10-methoxy-2-oxo-6,7-dihydrobenzo[a]quinolizine-3-carboxamide;
9-benzyloxy-6-ethyl-10-methoxy-2-oxo-N-sec-butyl-6,7-dihydrobenzo[a]quinolizine-3-carboxamide;
9-benzyloxy-6-ethyl-10-methoxy-2-oxo-6,7-dihydrobenzo[a]quinolizine-3-carbohydroxamic acid;
9-benzyloxy-N-[2-(dimethylamino)-1-methyl-ethyl]-6-ethyl-10-methoxy-2-oxo-6,7-dihydrobenzo[a]quinolizine-3-carboxamide;
9-benzyloxy-6-ethyl-10-methoxy-N-(2-methoxyethyl)-2-oxo-6,7-dihydrobenzo[a]quinolizine-3-carboxamide;
4-[6-ethyl-10-methoxy-9-(3-methoxypropoxy)-2-oxo-6,7-dihydrobenzo[a]quinolizine-3-carbonyl]morpholine-2-carboxylic acid;
6-ethyl-10-methoxy-9-(3-methoxypropoxy)-2-oxo-N-(1H-tetrazol-5-yl)-6,7-dihydrobenzo[a]quinolizine-3-carboxamide;
N-benzyl-6-ethyl-10-methoxy-9-(3-methoxypropoxy)-2-oxo-6,7-dihydrobenzo[a]quinolizine-3-carboxamide;
6-ethyl-10-methoxy-N-(2-methoxy-1-methyl-ethyl)-9-(3-methoxypropoxy)-2-oxo-6,7-dihydrobenzo[a]quinolizine-3-carboxamide;
9-ethoxy-6-ethyl-10-methoxy-N-(2-methoxy-1-methyl-ethyl)-2-oxo-6,7-dihydrobenzo[a]quinolizine-3-carboxamide;
6-ethyl-9-isobutoxy-10-methoxy-N-(2-methoxy-1-methyl-ethyl)-2-oxo-6,7-dihydrobenzo[a]quinolizine-3-carboxamide;
9-(cyclopropylmethoxy)-6-ethyl-10-methoxy-N-(2-methoxy-1-methyl-ethyl)-2-oxo-6,7-dihydrobenzo[a]quinolizine-3-carboxamide;
6-ethyl-3-(hydroxymethyl)-10-methoxy-9-(3-methoxypropoxy)-6,7-dihydrobenzo[a]quinolizin-2-one;
4-[[6-ethyl-10-methoxy-9-(3-methoxypropoxy)-2-oxo-6,7-dihydrobenzo[a]quinolizin-3-yl]methyl]morpholine-3-carboxylic acid;
1-[[6-ethyl-10-methoxy-9-(3-methoxypropoxy)-2-oxo-6,7-dihydrobenzo[a]quinolizin-3-yl]methyl]piperidine-2-carboxylic acid;
1-[[6-ethyl-10-methoxy-9-(3-methoxypropoxy)-2-oxo-6,7-dihydrobenzo[a]quinolizin-3-yl]methyl]pyrrolidine-2-carboxylic acid;
6-ethyl-10-methoxy-9-(3-methoxypropoxy)-3-(1-piperidylmethyl)-6,7-dihydrobenzo[a]quinolizin-2-one;
6-ethyl-10-methoxy-9-(3-methoxypropoxy)-3-(pyrrolidin-1-ylmethyl)-6,7-dihydrobenzo[a]quinolizin-2-one;
6-ethyl-10-methoxy-9-(3-methoxypropoxy)-3-(morpholinomethyl)-6,7-dihydrobenzo[a]quinolizin-2-one;
6-ethyl-10-methoxy-9-(3-methoxypropoxy)-3-(methylaminomethyl)-6,7-dihydrobenzo[a]quinolizin-2-one;
3-[(dimethylamino)methyl]-6-ethyl-10-methoxy-9-(3-methoxypropoxy)-6,7-dihydrobenzo[a]quinolizin-2-one;
6-ethyl-10-methoxy-3-(methoxymethyl)-9-(3-methoxypropoxy)-6,7-dihydrobenzo[a]quinolizin-2-one;

6-cyclobutyl-10-methoxy-9-(3-methoxypropoxy)-2-oxo-N-(1H-tetrazol-5-yl)-6,7-dihydrobenzo[a]quinolizine-3-carboxamide;

(6R)-6-ethyl-9,10-dimethoxy-2-oxo-N-(1H-tetrazol-5-yl)-6,7-dihydrobenzo[a]quinolizine-3-carboxamide;

6-tert-butyl-10-methoxy-9-(3-methoxypropoxy)-2-oxo-N-(1H-tetrazol-5-yl)-6,7-dihydrobenzo[a]quinolizine-3-carboxamide;

6-cyclobutyl-10-methoxy-9-(3-methoxypropoxy)-2-oxo-N-(1H-tetrazol-5-yl)-6,7-dihydrobenzo[a]quinolizine-3-carboxamide;

11-chloro-6-isopropyl-9-(2-methoxyethoxy)-2-oxo-N-(1H-tetrazol-5-yl)-6,7-dihydrobenzo[a]quinolizine-3-carboxamide;

9,10-dimethoxy-2-oxo-N-(1H-tetrazol-5-yl)-6-(2,2,2-trifluoroethyl)-6,7-dihydrobenzo[a]quinolizine-3-carboxamide;

6-isopropyl-10-methoxy-9-(3-methoxypropoxy)-2-oxo-N-(1H-tetrazol-5-yl)-6,7-dihydrobenzo[a]quinolizine-3-carboxamide;

10-chloro-6-isopropyl-9-(3-methoxypropoxy)-2-oxo-N-(1H-tetrazol-5-yl)-6,7-dihydrobenzo[a]quinolizine-3-carboxamide;

(+)-10-chloro-6-isopropyl-9-(3-methoxypropoxy)-2-oxo-N-(1H-tetrazol-5-yl)-6,7-dihydrobenzo[a]quinolizine-3-carboxamide;

or pharmaceutically acceptable salts thereof.

More particularly, the invention relates to the following compounds of formula (I):

9-benzyloxy-6-ethyl-10-methoxy-N-methylsulfonyl-2-oxo-6,7-dihydrobenzo[a]quinolizine-3-carboxamide;

6-ethyl-10-methoxy-9-(3-methoxypropoxy)-2-oxo-N-(1H-tetrazol-5-yl)-6,7-dihydrobenzo[a]quinolizine-3-carboxamide;

9-ethoxy-6-ethyl-10-methoxy-N-(2-methoxy-1-methyl-ethyl)-2-oxo-6,7-dihydrobenzo[a]quinolizine-3-carboxamide;

6-ethyl-9-isobutoxy-10-methoxy-N-(2-methoxy-1-methyl-ethyl)-2-oxo-6,7-dihydrobenzo[a]quinolizine-3-carboxamide;

3-[(dimethylamino)methyl]-6-ethyl-10-methoxy-9-(3-methoxypropoxy)-6,7-dihydrobenzo[a]quinolizin-2-one;

6-ethyl-10-methoxy-3-(methoxymethyl)-9-(3-methoxypropoxy)-6,7-dihydrobenzo[a]quinolizin-2-one;

6-tert-butyl-10-methoxy-9-(3-methoxypropoxy)-2-oxo-N-(1H-tetrazol-5-yl)-6,7-dihydrobenzo[a]quinolizine-3-carboxamide;

6-cyclobutyl-10-methoxy-9-(3-methoxypropoxy)-2-oxo-N-(1H-tetrazol-5-yl)-6,7-dihydrobenzo[a]quinolizine-3-carboxamide;

10-chloro-6-isopropyl-9-(3-methoxypropoxy)-2-oxo-N-(1H-tetrazol-5-yl)-6,7-dihydrobenzo[a]quinolizine-3-carboxamide;

(6S)-10-chloro-6-isopropyl-9-(3-methoxypropoxy)-2-oxo-N-(1H-tetrazol-5-yl)-6,7-dihydrobenzo[a]quinolizine-3-carboxamide;

or pharmaceutically acceptable salts thereof.

It will be appreciated, that the compounds of general formula (I) in this invention may be derivatised at functional groups to provide derivatives which are capable of conversion back to the parent compound in vivo. Physiologically acceptable and metabolically labile derivatives, which are capable of producing the parent compounds of general formula (I) in vivo are also within the scope of this invention.

Synthesis

The compounds of the present invention can be prepared by any conventional means. Suitable processes for synthesizing these compounds as well as their starting materials are provided in the schemes below and in the examples. All substituents, in particular, $R^1$ to $R^7$, X and Y are as defined above unless otherwise indicated. Furthermore, and unless explicitly otherwise stated, all reactions, reaction conditions, abbreviations and symbols have the meanings well known to a person of ordinary skill in organic chemistry.

General Synthetic Route for Intermediates (Scheme 1)

Scheme 1

Method 1)

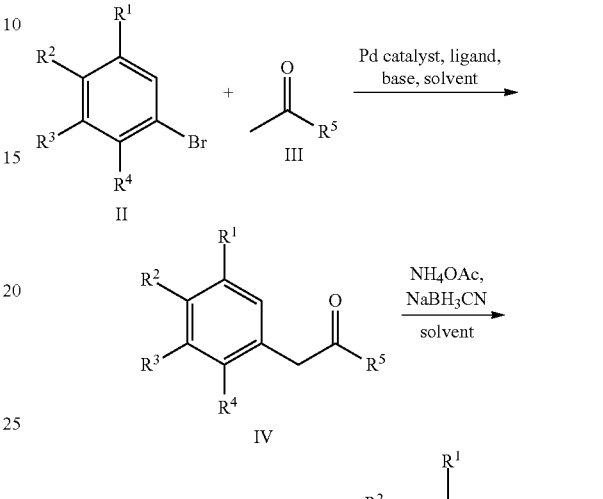

Method 2)

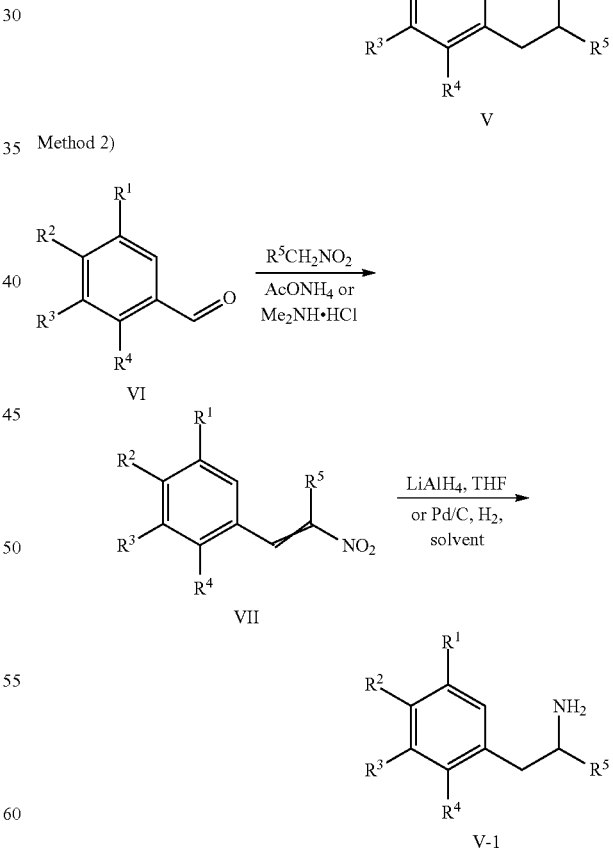

Intermediates can be Prepared According to Scheme 1.

By Method 1), coupling reaction of II with III affords IV. The reaction can be carried out in the presence of Pd catalyst such as $Pd_2(dba)_3$, $Pd(PPh_3)_4$ or $PdCl_2(PPh_3)_2$, a ligand such as Xantphos, and a suitable base such as t-BuONa, $Na_2CO_3$ or Cs$_2$CO$_3$, in a suitable solvent such as THF, toluene or 1,4-dioxane at room temperature to 130° C. Reductive amination of IV affords Compound V.

By Method 2), Compound VI reacts with nitroalkane in the presence of ammonium acetate or dimethylamine hydrochloride affords VII, which is reduced by LiAlH$_4$ or undergoes hydrogenation in the presence of Pd/C to give V-1.

General Synthetic Route for Compounds Ia, Ib and Ic (Scheme 2)

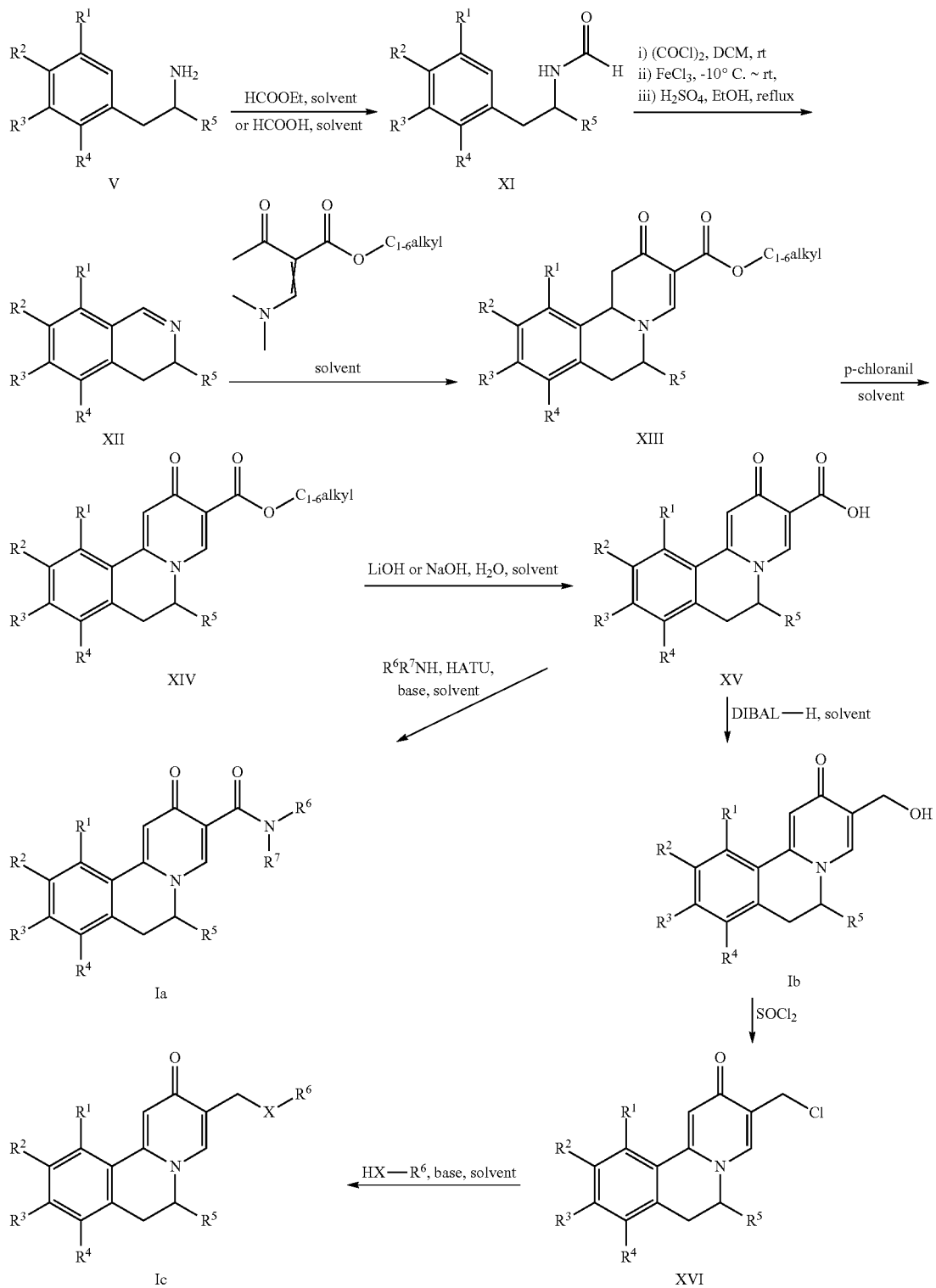

The compound of formula Ia, Ib, and Ic can be prepared according to Scheme 2. Compound V is heated with ethyl formate or formic acid in a solvent such as ethanol or dioxane to afford Compound XI. Compound XI is treated with oxalyl chloride followed by $FeCl_3$ at −10° C. to room temperature, and then after separation, the intermediate is heated with a solution of concentrated $H_2SO_4$ in methanol to give Compound XII. Compound XII reacts with $C_{1-6}$alkyl 2-(dimethylaminomethylene)-3-oxo-butanoate in a solvent such as DMSO, DMF or ethanol to give Compound XIII. After dehydrogenation by p-chloranil, Compound XIV is obtained. Hydrolyzation of XIV by lithium hydroxide or sodium hydroxide in a suitable solvent such as $THF/H_2O$, $EtOH/H_2O$ or $MeOH/H_2O$ affords Compound XV. Compound XV reacts with an amine in the presence of HATU, a base such as DIPEA, TEA or $NaHCO_3$, in a solvent such as DMF to give Ia. Compound XV can be reduced by DIBAL-H to give compound Ib, which is converted to compound XVI by $SOCl_2$. Compound XVI reacts with an amine or alcohol in the presence of a base such as TEA to give compound Ic.

Chiral compound of formula I can be prepared by chiral HPLC separation of corresponding racemic compound.

This invention also relates to a process for the preparation of a compound of formula (I) comprising one of the following steps:

(a) the reaction of a compound of formula (A)

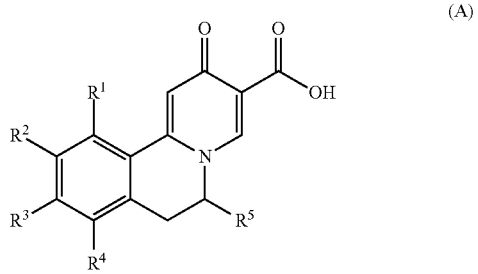

with $R^6R^7NH$ and HATU in the presence of a base; or (b) the reaction of a compound of formula (B)

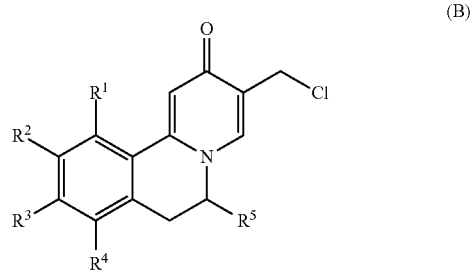

with $HX—R^6$ in the presence of a base; wherein X, $R^1$ to $R^7$ are defined above unless otherwise indicated.

In step (a) and step (b), a base can be for example independently selected from $Et_3N$, DIPEA and $K_2CO_3$.

A compound of formula I when manufactured according to the above process is also an object of the invention.

Pharmaceutical Compositions and Administration

The invention also relates to a compound of formula I for use as therapeutically active substance.

Another embodiment provides pharmaceutical compositions or medicaments containing the compounds of the invention and a therapeutically inert carrier, diluent or excipient, as well as methods of using the compounds of the invention to prepare such compositions and medicaments. In one example, compounds of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compounds of formula (I) are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations, and is the minimum amount necessary to inhibit HBsAg. For example, such amount may be below the amount that is toxic to normal cells, or the mammal as a whole.

In one example, the pharmaceutically effective amount of the compound of the invention administered parenterally per dose will be in the range of about 0.01 to 100 mg/kg, alternatively about 0.01 to 100 mg/kg of patient body weight per day, with the typical initial range of compound used being 0.3 to 15 mg/kg/day. In another embodiment, oral unit dosage forms, such as tablets and capsules, preferably contain from about 0.1 to about 1000 mg of the compound of the invention.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

An example of a suitable oral dosage form is a tablet containing about 0.1 to 1000 mg of the compound of the invention compounded with about 0 to 2000 mg anhydrous lactose, about 0 to 2000 mg sodium croscarmellose, about 0 to 2000 mg polyvinylpyrrolidone (PVP) K30, and about 0 to 2000 mg magnesium stearate. The powdered ingredients are first mixed together and then mixed with a solution of the PVP. The resulting composition can be dried, granulated, mixed with the magnesium stearate and compressed to tablet form using conventional equipment. An example of an aerosol formulation can be prepared by dissolving the compound, for example 0.1 to 1000 mg, of the invention in a suitable buffer solution, e.g. a phosphate buffer, adding a tonicifier, e.g. a salt such sodium chloride, if desired. The solution may be filtered, e.g., using a 0.2 micron filter, to remove impurities and contaminants.

An embodiment, therefore, includes a pharmaceutical composition comprising a compound of Formula I, or a stereoisomer or pharmaceutically acceptable salt thereof. In a further embodiment includes a pharmaceutical composition comprising a compound of Formula I, or a stereoisomer or pharmaceutically acceptable salt thereof, together with a pharmaceutically acceptable carrier or excipient.

The following example A and B illustrate typical compositions of the present invention, but serve merely as representative thereof.

Example A

A compound of formula I can be used in a manner known per se as the active ingredient for the production of tablets of the following composition:

|  | Per tablet |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
|  | 425 mg |

Example B

A compound of formula I can be used in a manner known per se as the active ingredient for the production of capsules of the following composition:

|  | Per capsule |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
|  | 220.0 mg |

Indications and Methods of Treatment

The compounds of the invention can inhibit HBsAg production or secretion and inhibit HBV gene expression. Accordingly, the compounds of the invention are useful for the treatment or prophylaxis of HBV infection.

The invention relates to the use of a compound of formula I for the inhibition of HBsAg production or secretion.

The invention relates to the use of a compound of formula I for the inhibition of HBV gene expression.

The invention relates to the use of a compound of formula I for the treatment or prophylaxis of HBV infection.

The use of a compound of formula I for the preparation of medicaments useful in the treatment or prophylaxis diseases that are related to HBV infection is an object of the invention.

The invention relates in particular to the use of a compound of formula I for the preparation of a medicament for the treatment or prophylaxis of HBV infection.

Another embodiment includes a method for the treatment or prophylaxis of HBV infection, which method comprises administering an effective amount of a compound of Formula I, a stereoisomer, tautomer, prodrug, conjugates or pharmaceutically acceptable salt thereof.

Combination Therapy

The compounds of the invention can be combined with other anti HBV agents such as interferon alpha-2b, interferon alpha-2a, and interferon alphacon-1 (pegylated and unpegylated), ribavirin, lamivudine (3TC), entecavir, tenofovir, telbivudine (LdT), adefovir, or other emerging anti HBV agents such as HBV RNA replication inhibitor, HBsAg secretion inhibitors, HBV capsid inhibitors, antisense oligomer, siRNA, HBV therapeutic vaccine, HBV prophylactic vaccine, HBV antibody therapy (monoclonal or polyclonal) and TLR 2, 3, 7, 8 and 9 agonists for the treatment or prophylaxis of HBV.

BRIEF DESCRIPTION OF THE FIGURES

FIG. 1. X-ray structure of (6S)-6-ethyl-9,10-dimethoxy-2-oxo-6,7-dihydrobenzo[a]quinolizine-3-carboxylic acid [the (S)-enantiomer intermediate of step 6 in Example 31]

EXAMPLES

The invention will be more fully understood by reference to the following examples. They should not, however, be construed as limiting the scope of the invention.

Abbreviations used herein are as follows:
μL: microliter
μm: micrometer
μM: micromoles per liter
AcOH: acetic acid
Ar: argon
BSA: bovine serum albumin
$CHC_3$: trichloromethane
conc. concentrated
DCM or $CH_2Cl_2$: dichloromethane
DIPEA: N,N-diisopropylethylamine
DME: 1,2-dimethoxyethane
DMF: dimethylformamide
DMSO-d6: deuterated dimethylsulfoxide
EtOAc: ethyl acetate
EtOH: ethanol
$Et_2O$: diethyl ether
$Et_3N$ or TEA: triethylamine
g: gram
h or hr: hour
hrs: hours
$IC_{50}$: the half maximal inhibitory concentration
HATU: O-(7-aza-1H-benzotriazole-1-yl)-N,N,N',N'-tetramethyluronium hexafluorophosphate
HCl: hydrochloric acid HOAc acetic acid
H$_2$SO$_4$: sulfuric acid
HPLC: high performance liquid chromatography
K$_2$CO$_3$: potassium carbonate
LC/MS: Liquid chromatography/mass spectrometry
MeOH or CH$_3$OH: methanol
METHANOL-d$_4$: perdeuteromethanol
M: molarity
mg: milligram
MHz: megahertz
min: minute
mins: minutes
mL: milliliter
mM: millimoles per liter
mm: millimeter
mmol: millimole
MS (ESI): mass spectroscopy (electron spray ionization)
NaOH: sodium hydroxide
Na$_2$SO$_4$: sodium sulfate
NaBH$_3$CN: sodium cyanotrihydroborate
NaHCO$_3$: sodium hydrogen carbonate
nM: nanomoles per liter
nm: nanometer
NMR: nuclear magnetic resonance
N$_2$: nitrogen
obsd. observed
rt: room temperature
Pd/C: palladium on activated carbon
Pd(PPh$_3$)$_4$: tetrakis(triphenylphosphine)palladium(0)
Pd(PPh$_3$)$_2$Cl$_2$: bis(triphenylphosphine)palladium(II) chloride
Pd(dppf)Cl$_2$: [1,1'-bis(diphenylphosphino)ferrocene]dichloropalladium(II)
prep-HPLC: preparative high performance liquid chromatography
POCl$_3$: phosphorus oxychloride
sat. Saturated
t-BuONa: sodium tert-butoxide
TEA: triethylamine
THF: tetrahydrofuran
TLC: thin layer chromatography
δ: chemical shift
Xantphos: 4,5-bis(diphenylphosphino)-9,9-dimethylxanthene General Experimental Conditions Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd., pore: 200-300 or 300-400, Intermediates and final compounds were purified by preparative HPLC on reversed phase column using X Bridge™ Perp C$_{18}$ (5 μm, OBD™ 30×100 mm) column or SunFire™ Perp C$_{18}$ (5 μm, OBD™ 30×100 mm) column.

LC/MS spectra were obtained using an Acquity Ultra Performance LC-3100 Mass Detector or Acquity Ultra Performance LC-SQ Detector. Standard LC/MS conditions were as follows (running time 3 minutes):

Acidic condition: A: 0.1% formic acid in H$_2$O; B: 0.1% formic acid in acetonitrile;

Basic condition: A: 0.05% NH$_3$H$_2$O in H$_2$O; B: acetonitrile;

Neutral condition: A: H$_2$O; B: acetonitrile.

Mass spectra (MS): generally only ions which indicate the parent mass are reported, and unless otherwise stated the mass ion quoted is the positive mass ion (M+H)$^+$.

The microwave assisted reactions were carried out in a Biotaae Initiator Sixty or CEM Discover.

NMR Spectra were obtained using Bruker Avance 400 MHz.

A single crystal was mounted in a loop and cooled to 160 K in a nitrogen stream. Data were collected on a Gemini R Ultra diffractometer (Oxford Diffraction, UK) with Cu—K-alpha-radiation (1.54178 Å) and processed with the Crysalis-package. Structure solution and refinement was performed using the ShelXTL software (Bruker AXS, Karlsruhe).

All reactions involving air-sensitive reagents were performed under an argon atmosphere. Reagents were used as received from commercial suppliers without further purification unless otherwise noted.

PREPARATIVE EXAMPLES

Example 1: N-benzyl-9-benzyloxy-6-ethyl-10-methoxy-2-oxo-6,7-dihydrobenzo[a]quinolizine-3-carboxamide

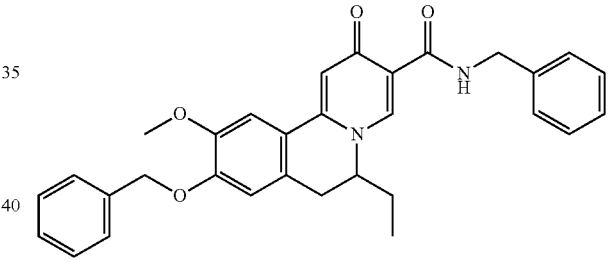

Step 1: Preparation of 3-benzyloxy-4-methoxy-benzaldehyde

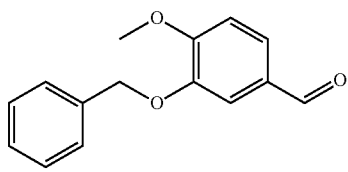 [SMILES: COc1ccc(C=O)cc1OCc1ccccc1]

A 5 L round-bottomed flask was charged with 3-hydroxy-4-methoxy-benzaldehyde (304 g, 2 mol), bromomethylbenzene (445 g, 2.6 mol, TCI), K$_2$CO$_3$ (608 g, 4.4 mol) and acetone (3 L). The resultant mixture was stirred at 20° C. for 16 hours, and then filtered and concentrated to give a yellow oil which was stood for 16 hours at room temperature. Then petroleum ether (1 L) was added and the mixture was stirred for 30 minutes and then filtered. The filter cake was dried to give 3-benzyloxy-4-methoxy-benzaldehyde (400 g).

Step 2: Preparation of 2-benzyloxy-1-methoxy-4-[2-nitrobut-1-enyl]benzene

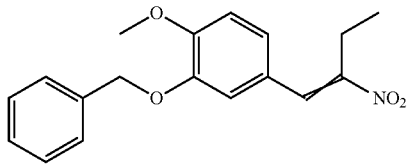 [SMILES: CCC(=Cc1ccc(OC)c(OCc2ccccc2)c1)[N+](=O)[O-]]

A mixture of 3-benzyloxy-4-methoxy-benzaldehyde (300 g, 1.24 mol) and ammonium acetate (95 g, 1.24 mol) in toluene (4 L) was refluxed with a Dean-Stark trap for 2 hours. Then nitropropane (552 g, 6.19 mol, TCI) was added and the resultant mixture was refluxed for additional 36 hours. The mixture was concentrated under reduced pressure, and then the residue was dissolved in ethyl acetate (2 L). The resultant solution was washed with water (1 L), dried over anhydrous $Na_2SO_4$ and concentrated. The residue was purified by column chromatography to give 2-benzyloxy-1-methoxy-4-[2-nitrobut-1-enyl]benzene (270 g).

Step 3: Preparation of 1-(3-benzyloxy-4-methoxy-phenyl)butan-2-amine

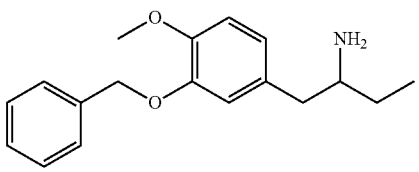 [SMILES: CCC(N)Cc1ccc(OC)c(OCc2ccccc2)c1]

To a mixture of $LiAlH_4$ (101 g, 2.67 mol) in THF (1500 mL) cooled with an ice-water bath was added a solution of 2-benzyloxy-1-methoxy-4-[2-nitrobut-1-enyl]benzene (270 g, 862 mmol) in THF (1000 mL) dropwise. After addition, the mixture was refluxed for 6 hours and then stirred at room temperature for additional 16 hours. Water (101 g) was added dropwise to the mixture at 0° C., and then followed by addition of 15% NaOH aqueous solution (101 mL) and water (303 mL). The resultant mixture was filtered, and the filtrate was concentrated to afford crude 1-(3-benzyloxy-4-methoxy-phenyl)butan-2-amine (224 g) which was used in the next step without further purification.

Step 4: Preparation of N-[1-[(3-benzyloxy-4-methoxy-phenyl)methyl]propyl]formamide

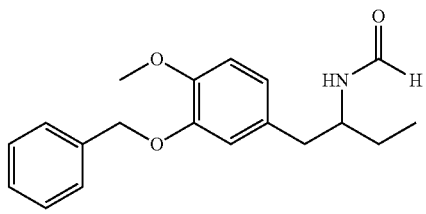 [SMILES: CCC(Cc1ccc(OC)c(OCc2ccccc2)c1)NC=O]

A mixture of 1-(3-benzyloxy-4-methoxy-phenyl)butan-2-amine (224 g, 785 mmol) and formic acid (145 g, 3.14 mol, Aldrich) in dioxane (2 L) was refluxed for 16 hours and then concentrated under reduced pressure to afford the crude N-[1-[(3-benzyloxy-4-methoxy-phenyl)methyl]propyl]formamide (230 g), which was used in the next step without purification.

Step 5: Preparation of 6-benzyloxy-3-ethyl-7-methoxy-3,4-dihydroisoquinoline

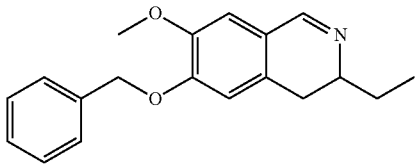 [SMILES: CCC1Cc2cc(OCc3ccccc3)c(OC)cc2C=N1]

To a solution of N-[1-[(3-benzyloxy-4-methoxy-phenyl)methyl]propyl]formamide (230 g, 734 mmol) in acetonitrile (2000 mL) was added $POCl_3$ (189.16 g, 1.23 mol) dropwise at 0-5° C. The resultant mixture was refluxed for 4 hours and then concentrated. Ethyl acetate (3 L) was added to the mixture, and then followed by addition of ammonia to adjust the pH of the aqueous solution to around 11. The aqueous layer was extracted with ethyl acetate (2 L×3). The organic layers were combined and then concentrated. The residue was purified by column chromatography to give 6-benzyloxy-3-ethyl-7-methoxy-3,4-dihydroisoquinoline (90 g).

Step 6: Preparation of ethyl 9-benzyloxy-6-ethyl-10-methoxy-2-oxo-1,6,7,11b-tetrahydrobenzo[a]quinolizine-3-carboxylate

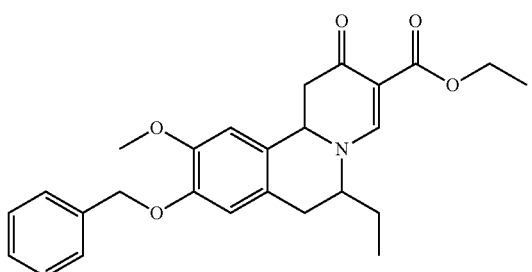

A mixture of 6-benzyloxy-3-ethyl-7-methoxy-3,4-dihydroisoquinoline (10 g, 34 mmol) and ethyl 2-(ethoxymethylene)-3-oxo-butanoate (6.9 g, 37.4 mmol, General Material Company Limited) in EtOH (150 mL) was refluxed overnight. The mixture was concentrated to give crude ethyl 9-benzyloxy-6-ethyl-10-methoxy-2-oxo-1,6,7,11b-tetrahydrobenzo[a]quinolizine-3-carboxylate as a dark brown oil which was used in the next step without purification.

Step 7: Preparation of ethyl 9-benzyloxy-6-ethyl-10-methoxy-2-oxo-6,7-dihydrobenzo[a]quinolizine-3-carboxylate

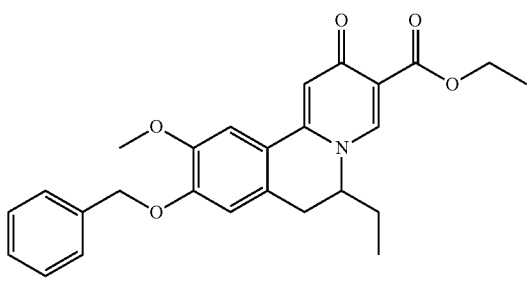 [SMILES: CCOC(=O)C1=CN2C(CC)Cc3cc(OCc4ccccc4)c(OC)cc3C2CC1=O]

A mixture of crude ethyl 9-benzyloxy-6-ethyl-10-methoxy-2-oxo-1,6,7,11b-tetrahydrobenzo[a]quinolizine-3-carboxylate from Step 6 and p-chloranil (4.97 g, 20.4 mmol, TCI) in DME (40 mL) was refluxed for 2 hours. After being cooled to room temperature, the suspension was filtered with suction. The filter cake was washed with cold DME and then dried under vacuum to give ethyl 9-benzyloxy-6-ethyl-10-methoxy-2-oxo-6,7-dihydrobenzo[a]quinolizine-3-carboxylate as a yellow solid (5.2 g).

Step 8: Preparation of 9-benzyloxy-6-ethyl-10-methoxy-2-oxo-6,7-dihydrobenzo[a]quinolizine-3-carboxylic Acid

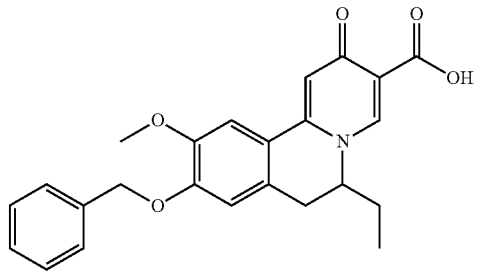 [SMILES: CCC1Cc2cc(OCc3ccccc3)c(OC)cc2-c2cc(=O)c(C(=O)O)cn21]

To a solution of ethyl 9-benzyloxy-6-ethyl-10-methoxy-2-oxo-6,7-dihydrobenzo[a]quinolizine-3-carboxylate (2 g, 4.6 mmol) in THF (20 mL) was added 10% NaOH aqueous solution dropwise at room temperature. The resultant mixture was stirred for 2 hours, and then acidified to pH 1-2 with 2 M hydrochloric acid. The mixture was extracted with DCM (20 mL×2), and the combined organic layers were washed with brine, dried over anhydrous $Na_2SO_4$ and concentrated. The residue was purified by prep-HPLC to give 9-benzyloxy-6-ethyl-10-methoxy-2-oxo-6,7-dihydrobenzo[a]quinolizine-3-carboxylic acid (1.5 g) as a light yellow solid.

Step 9: Preparation of N-benzyl-9-benzyloxy-6-ethyl-10-methoxy-2-oxo-6,7-dihydrobenzo[a]quinolizine-3-carboxamide

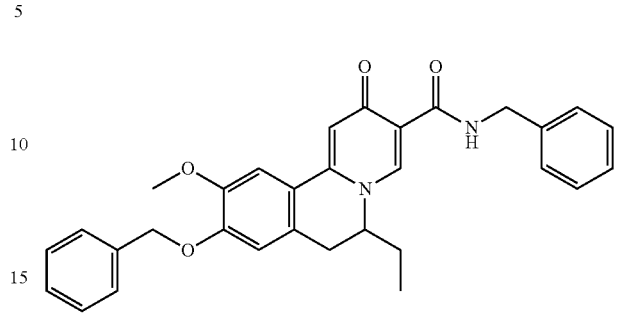

To a solution of 9-benzyloxy-6-ethyl-10-methoxy-2-oxo-6,7-dihydrobenzo[a]quinolizine-3-carboxylic acid (81 mg, 0.2 mmol) in DMF (10 mL) was added HATU (114 mg, 0.3 mmol), triethylamine (100 μL) and phenylmethanamine (32 mg, 0.3 mmol, Acros Organics). The resultant solution was stirred at room temperature for 3 h and then purified by preparative HPLC to afford N-benzyl-9-benzyloxy-6-ethyl-10-methoxy-2-oxo-6,7-dihydrobenzo[a]quinolizine-3-carboxamide (23 mg). $^1$H NMR (400 MHz, $CDCl_3$): δ 8.53 (s, 1H), 7.39 (m, 11H), 6.96 (s, 1H), 6.76 (s, 1H), 5.21 (s, 2H), 4.68 (d, 2H), 4.18 (m, 1H), 3.95 (s, 3H), 3.33 (m, 1H), 2.82 (m, 1H), 1.63 (m, 2H), 0.90 (t, 3H). MS obsd. ($ESI^+$) [$(M+H)^+$]: 495.

Example 2: 9-benzyloxy-6-ethyl-10-methoxy-N-methyl-2-oxo-6,7-dihydrobenzo[a]quinolizine-3-carboxamide

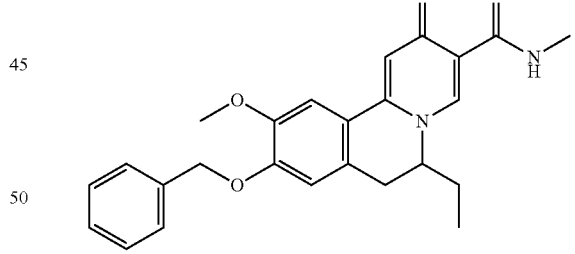

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 μL) and methylamine hydrochloride (150 mg, 2.2 mmol). The resultant solution was stirred at room temperature for 3 h and then purified by preparative HPLC to afford 9-benzyloxy-6-ethyl-10-methoxy-3-(4-methylpiperazine-1-carbonyl)-6,7-dihydrobenzo[a]quinolizin-2-one (21 mg). $^1$HNMR (400 MHz, MeOD): δ 8.60 (s, 1H), 7.41 (m, 6H), 7.04 (s, 2H), 5.22 (s, 2H), 4.48 (m, 1H), 3.96 (s, 3H), 3.34 (m, 1H), 3.03 (m, 2H), 2.98 (s, 3H), 2.61 (m, 2H), 1.63 (m, 2H), 0.90 (t, 3H). MS obsd. ($ESI^-$) [$(M+H)^+$]: 419.

Example 3: 9-benzyloxy-6-ethyl-10-methoxy-N-(2-methoxy-1-methyl-ethyl)-2-oxo-6,7-dihydrobenzo[a]quinolizine-3-carboxamide

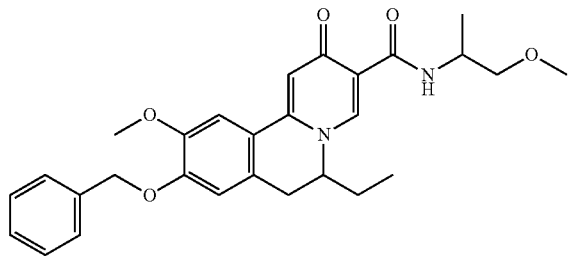 [SMILES: CCC1Cc2cc(OCc3ccccc3)c(OC)cc2-c2cc(=O)c(C(=O)NC(C)COC)cn21]

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 μL) and 1-methoxy-2-propanamine (350 mg, Aldrich). The resultant solution was stirred at room temperature for 3 h and then purified by preparative HPLC to afford 9-benzyloxy-6-ethyl-10-methoxy-N-(2-methoxy-1-methyl-ethyl)-2-oxo-6,7-dihydrobenzo[a]quinolizine-3-carboxamide (21 mg). $^1$H NMR (400 MHz, MeOD): δ 8.57 (s, 1H), 7.40 (m, 6H), 7.03 (s, 2H), 5.20 (s, 2H), 4.48 (m, 2H), 4.27 (m, 2H), 3.95 (s, 3H), 3.49 (s, 3H), 3.02 (m, 2H), 1.59 (m, 2H), 1.28 (d, 3H), 0.88 (t, 3H). MS obsd. (ESI$^+$) [(M+H)$^+$]: 477.

Example 4: 9-benzyloxy-6-ethyl-10-methoxy-N-methylsulfonyl-2-oxo-6,7-dihydrobenzo[a]quinolizine-3-carboxamide

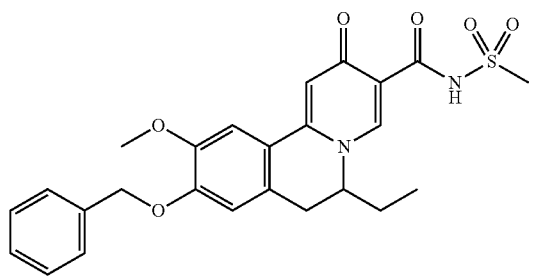 [SMILES: CCC1Cc2cc(OCc3ccccc3)c(OC)cc2-c2cc(=O)c(C(=O)NS(C)(=O)=O)cn21]

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 μL) and methyanesulfonamide (285 mg, Alfa Aesar). The resultant solution was stirred at room temperature for 3 h and then purified by preparative HPLC to afford 9-benzyloxy-6-ethyl-10-methoxy-N-methylsulfonyl-2-oxo-6,7-dihydrobenzo[a]quinolizine-3-carboxamide (5 mg). $^1$HNMR (400 MHz, MeOD): δ 8.63 (s, 1H), 7.42 (m, 6H), 7.05 (s, 2H), 5.20 (s, 2H), 4.47 (m, 1H), 3.95 (s, 3H), 3.33 (m, 1H), 3.01 (m, 2H), 2.96 (s, 3H), 2.63 (m, 2H), 1.64 (m, 2H), 0.92 (t, 3H). MS obsd. (ESI$^+$) [(M+H)$^+$]: 483.

Example 5: 9-benzyloxy-6-ethyl-10-methoxy-2-oxo-N-propyl-6,7-dihydrobenzo[a]quinolizine-3-carboxamide

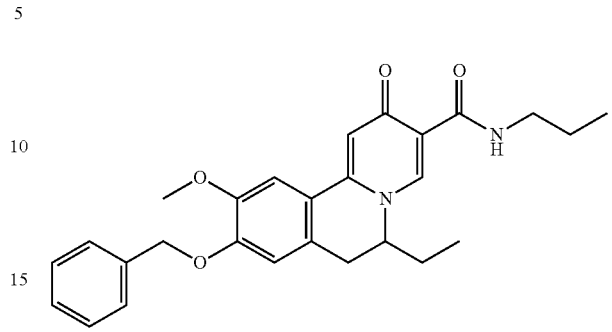

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 μL) and propylamine (180 mg, Alfa Aesar). The resultant solution was stirred at room temperature for 3 h and then purified by prep-HPLC to afford 9-benzyloxy-6-ethyl-10-methoxy-2-oxo-N-propyl-6,7-dihydrobenzo[a]quinolizine-3-carboxamide (14 mg). $^1$HNMR (400 MHz, MeOD): δ 8.59 (s, 1H), 7.40 (m, 6H), 7.03 (s, 2H), 5.21 (s, 2H), 4.47 (m, 2H), 3.95 (s, 3H), 3.75 (m, 2H), 3.54 (m, 2H), 3.33 (m, 1H), 3.01 (m, 2H), 2.99 (d, 1H), 1.57 (m, 2H), 0.89 (t, 3H). MS obsd. (ESI$^+$) [(M+H)$^+$]: 447.

Example 6: 9-benzyloxy-6-ethyl-N-(2-hydroxyethyl)-10-methoxy-2-oxo-6,7-dihydrobenzo[a]quinolizine-3-carboxamide

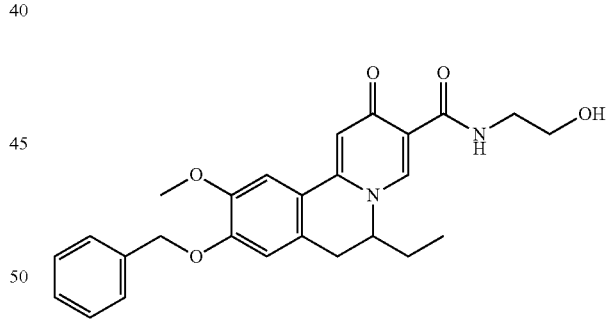

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 μL) and 2-aminoethyanol (180 mg, TCI). The resultant solution was stirred at room temperature for 3 h and then purified by preparative HPLC to afford 9-benzyloxy-6-ethyl-N-(2-hydroxyethyl)-10-methoxy-2-oxo-6,7-dihydrobenzo[a]quinolizine-3-carboxamide (11 mg). $^1$HNMR (400 MHz, MeOD): δ 8.59 (s, 1H), 7.41 (m, 6H), 7.05 (s, 2H), 5.22 (s, 2H), 4.48 (m, 2H), 3.96 (s, 3H), 3.40 (m, 2H), 3.01 (m, 2H), 2.99 (d, 1H), 1.65 (m, 2H), 0.87 (t, 3H). MS obsd. (ESI$^+$) [(M+H)$^+$]: 449.

Example 7: 9-benzyloxy-6-ethyl-N-(2-hydroxy-1-methyl-ethyl)-10-methoxy-2-oxo-6,7-dihydrobenzo[a]quinolizine-3-carboxamide

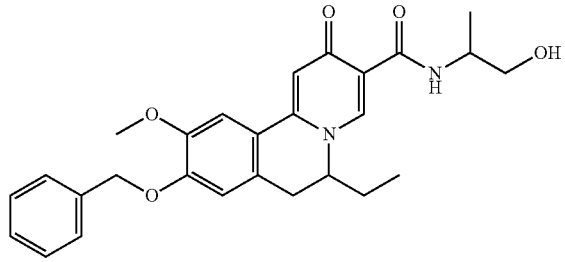 [SMILES: CCC1Cc2cc(OCc3ccccc3)c(OC)cc2-c2cc(=O)c(C(=O)NC(C)CO)cn21]

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 µL) and 2-aminopropan-1-ol (220 mg, Aldrich). The resulting solution was stirred at room temperature for 3 h and then purified by preparative HPLC to afford 9-benzyloxy-6-ethyl-N-(2-hydroxy-1-methyl-ethyl)-10-methoxy-2-oxo-6,7-dihydrobenzo[a]quinolizine-3-carboxamide (1.5 mg). $^1$HNMR (400 MHz, MeOD): δ8.67 (s, 1H), 7.50 (m, 6H), 7.14 (s, 1H), 7.06 (s, 1H), 5.21 (s, 2H), 4.47 (m, 1H), 4.18 (m, 1H), 3.98 (s, 3H), 3.61 (m, 1H), 3.45 (m, 2H), 3.33 (m, 1H), 3.02 (d, 1H), 1.62 (m, 3H), 1.29 (m, 3H), 0.92 (t, 3H). MS obsd. (ESI$^+$) [(M+H)$^+$]: 463.

Example 8: 9-benzyloxy-N-[2-(dimethylamino)-1-methyl-ethyl]-6-ethyl-10-methoxy-2-oxo-6,7-dihydrobenzo[a]quinolizine-3-carboxamide

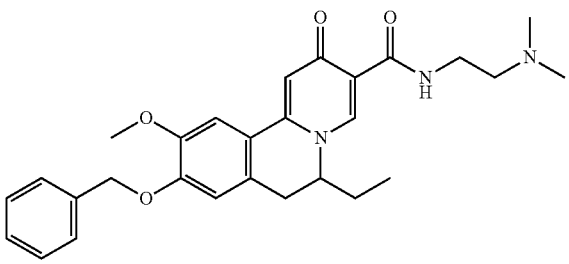 [SMILES: CCC1Cc2cc(OCc3ccccc3)c(OC)cc2-c2cc(=O)c(C(=O)NCCN(C)C)cn21]

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 µL) and N,N-dimethylethane-1,2-diamine (270 mg, TCI). The resultant solution was stirred at room temperature for 3 h and then purified by preparative HPLC to afford 9-benzyloxy-N-[2-(dimethylamino)-1-methyl-ethyl]-6-ethyl-10-methoxy-2-oxo-6,7-dihydrobenzo[a]quinolizine-3-carboxamide (27 mg). $^1$HNMR (400 MHz, MeOD): δ8.65 (s, 1H), 7.40 (m, 6H), 7.08 (d, 2H), 5.22 (s, 2H), 4.49 (m, 1H), 3.96 (s, 3H), 3.85 (m, 3H), 3.42 (m, 2H), 3.33 (m, 1H), 3.02 (d, 1H), 3.01 (s, 6H), 1.60 (m, 1H), 0.92 (t, 3H). MS obsd. (ESI$^+$) [(M+H)$^+$]: 476.

Example 9: 9-benzyloxy-6-ethyl-10-methoxy-2-oxo-N-sec-butyl-6,7-dihydrobenzo[a]quinolizine-3-carboxamide

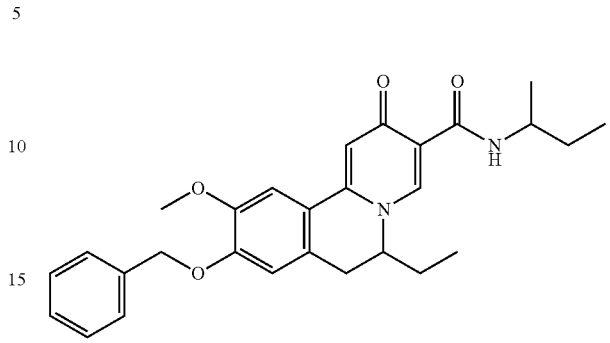

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 µL) and butan-2-amine (220 mg, Aldrich). The resultant solution was stirred at room temperature for 3 h and then purified by prep-HPLC to afford 9-benzyloxy-6-ethyl-10-methoxy-2-oxo-N-sec-butyl-6,7-dihydrobenzo[a]quinolizine-3-carboxamide (16 mg). $^1$HNMR (400 MHz, MeOD): δ8.59 (s, 1H), 7.40 (m, 6H), 7.05 (d, 2H), 5.22 (s, 2H), 4.49 (m, 1H), 4.01 (m, 1H), 3.96 (s, 3H), 3.33 (m, 1H), 3.02 (d, 1H), 1.63 (m, 4H), 1.26 (m, 3H), 1.02 (t, 3H), 0.92 (t, 3H). MS obsd. (ESI$^+$) [(M+H)$^+$]: 461.

Example 10: 9-benzyloxy-6-ethyl-10-methoxy-2-oxo-6,7-dihydrobenzo[a]quinolizine-3-carbohydroxamic Acid

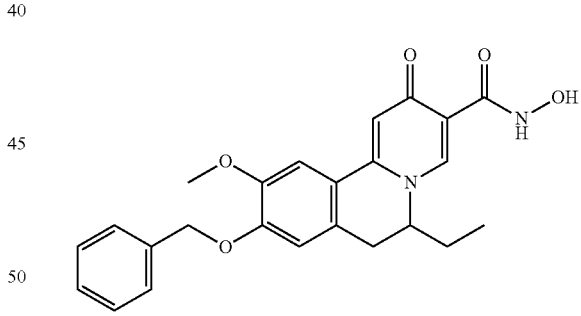

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 µL) and hydroxylamine hydrochloride (210 mg, Sinopharm Chemical reagent Co., Ltd). The resultant solution was stirred at room temperature for 3 h. The final product was purified by prep-HPLC to afford 9-benzyloxy-6-ethyl-10-methoxy-2-oxo-6,7-dihydrobenzo[a]quinolizine-3-carbohydroxamic acid (6 mg). $^1$HNMR (400 MHz, MeOD): δ8.59 (s, 2H), 7.40 (m, 6H), 7.04 (d, 2H), 5.21 (s, 2H), 4.60 (m, 1H), 4.49 (m, 1H), 3.96 (s, 3H), 3.33 (m, 1H), 3.03 (d, 1H), 1.59 (m, 2H), 0.89 (t, 3H). MS obsd. (ESI$^+$) [(M+H)$^+$]: 421.

Example 11: 9-benzyloxy-N-[2-(dimethylamino)-1-methyl-ethyl]-6-ethyl-10-methoxy-2-oxo-6,7-dihydrobenzo[a]quinolizine-3-carboxamide

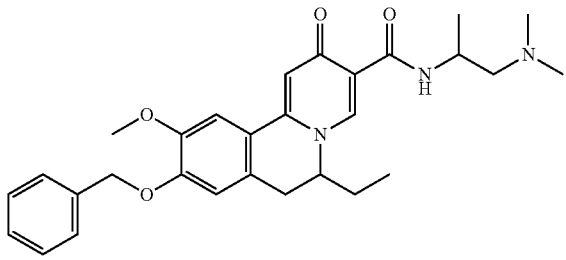 [SMILES: CCC1Cc2cc(OCc3ccccc3)c(OC)cc2-c2cc(=O)c(C(=O)NC(C)CN(C)C)cn21]

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL, 0.2 mmol) was added HATU (114 mg, 0.3 mmol), triethylamine (100 μL) and N1,N1-dimethylpropane-1,2-diamine (306 mg, Sigma Chemical). The resultant solution was stirred at room temperature for 3 h and then purified by prep-HPLC to afford 9-benzyloxy-N-[2-(dimethylamino)-1-methyl-ethyl]-6-ethyl-10-methoxy-2-oxo-6,7-dihydrobenzo[a]quinolizine-3-carboxamide (22 mg). $^1$HNMR (400 MHz, CDCl3): δ8.47 (s, 1H), 7.41 (m, 5H), 7.21 (s, 1H), 6.97 (s, 1H), 6.78 (s, 1H), 5.21 (s, 2H), 4.31 (m, 1H), 4.19 (m, 1H), 3.96 (s, 3H), 3.33 (m, 1H), 3.03 (d, 1H), 2.81 (d, 2H), 2.53 (m, 1H), 2.20 (s, 6H), 1.62 (m, 1H), 1.31 (m, 3H), 0.89 (t, 3H). MS obsd. (ESI$^+$) [(M+H)$^+$]: 490.

Example 12: 9-benzyloxy-6-ethyl-10-methoxy-N-(2-methoxyethyl)-2-oxo-6,7-dihydrobenzo[a]quinolizine-3-carboxamide

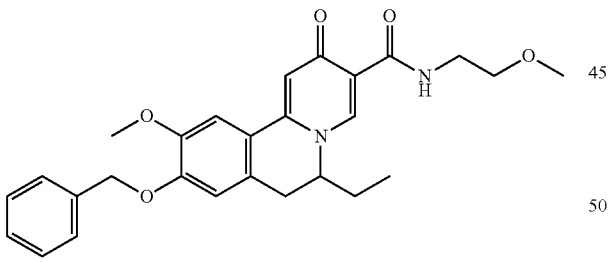

To a solution of 9-benzyloxy-6-ethyl-10-methoxy-2-oxo-6,7-dihydrobenzo[a]quinolizine-3-carboxylic acid (81 mg, 0.2 mmol, example 1, step 8) in DMF (10 mL) was added HATU (114 mg, 0.3 mmol), triethylamine (100 μL) and 2-methoxyethanamine (215 mg, TCI). The resulting solution was stirred at room temperature for 3 h and then purified by prep-HPLC without work-up to afford 9-benzyloxy-6-ethyl-10-methoxy-N-(2-methoxy-ethyl)-2-oxo-6,7-dihydrobenzo[a]quinolizine-3-carboxamide (17 mg). $^1$HNMR (400 MHz, CDCl3): δ8.48 (s, 1H), 7.26 (m, 6H), 7.22 (s, 1H), 6.96 (s, 1H), 6.76 (s, 1H), 5.21 (s, 2H), 4.19 (m, 1H), 3.96 (s, 3H), 3.68 (m, 4H), 3.43 (s, 3H), 3.30 (m, 1H), 2.81 (d, 1H), 1.56 (m, 1H), 0.89 (t, 3H). MS obsd. (ESI$^+$) [(M+H)$^+$]: 463.

Example 13: 4-[6-ethyl-10-methoxy-9-(3-methoxypropoxy)-2-oxo-6,7-dihydrobenzo[a]quinolizine-3-carbonyl]morpholine-2-carboxylic Acid

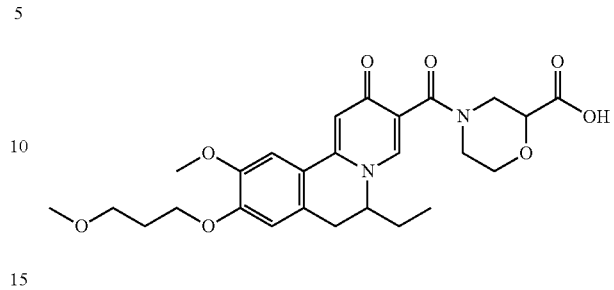

Step 1: Preparation of ethyl 6-ethyl-9-hydroxy-10-methoxy-2-oxo-6,7-dihydrobenzo[a]quinolizine-3-carboxylate

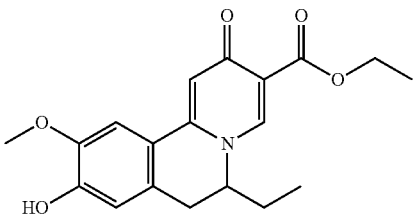 [SMILES: CCOC(=O)c1cn2c(cc1=O)-c1cc(OC)c(O)cc1CC2CC]

A mixture of ethyl-9-benzyloxy-6-ethyl-10-methoxy-2-oxo-6,7-dihydrobenzo[a]quinolizine-3-carboxylate (4.3 g, example 1, step 7) and 10% palladium on carbon (300 mg) in THF/MeOH (1/1, 40 mL) was stirred under a balloon of hydrogen atmosphere for 12 h. The mixture was filtered through celite, and the filtrate was concentrated under reduced pressure to afford ethyl 6-ethyl-9-hydroxy-10-methoxy-2-oxo-6,7-dihydrobenzo[a]quinolizine-3-carboxylate (4.0 g).

Step 2 Preparation of ethyl 6-ethyl-10-methoxy-9-(3-methoxypropoxy)-2-oxo-6,7-dihydrobenzo[a]quinolizine-3-carboxylate

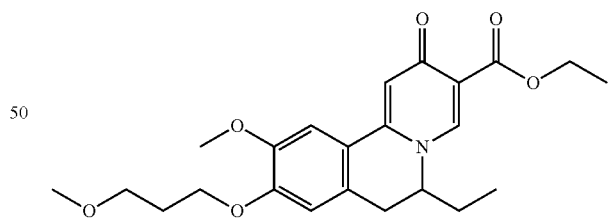

To a solution of ethyl 6-ethyl-9-hydroxy-10-methoxy-2-oxo-6,7-dihydrobenzo[a]quinolizine-3-carboxylate (3.4 g, 10 mmol) in DMF (30 mL) was added potassium carbonate (2.76 g, 20 mmol) and 1-bromo-3-methoxy-propane (3.04 g, 20 mmol, TCI). The resultant mixture was stirred at room temperature for 12 h and then poured into water (50 mL). The aqueous solution was extracted with EtOAc (50 mL×2). The organic layers were combined and washed with brine, dried over anhydrous Na$_2$SO$_4$, and concentrated under reduced pressure to give crude ethyl-6-ethyl-10-methoxy-9-(3-methoxypropoxy)-2-oxo-6,7-dihydrobenzo[a]quinolizine-3-carboxylate (3.92 g).

Step 3: Preparation of 6-ethyl-10-methoxy-9-(3-methoxypropoxy)-2-oxo-6,7-dihydrobenzo[a]quinolizine-3-carboxylic Acid

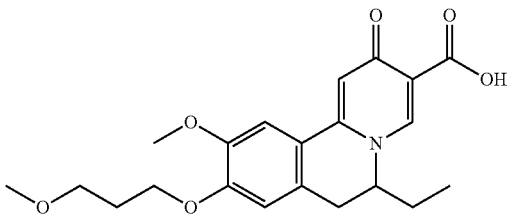 [SMILES: CCC1Cc2cc(OCCCOC)c(OC)cc2-c2cc(=O)c(C(=O)O)cn21]

To a solution of ethyl-6-ethyl-10-methoxy-9-(3-methoxypropoxy)-2-oxo-6,7-dihydrobenzo[a]quinolizine-3-carboxylate (2 g, 5 mmol) in THF (50 mL), was added 10% NaOH aqueous solution drop wise at rt. The resultant mixture was stirred for 2 h, and then acidified to pH=1-2 with 2M hydrochloric acid. The mixture was extracted with DCM (200 mL×2), and the combined organic layers were washed with brine, dried over anhydrous $Na_2SO_4$ and concentrated to afford 6-ethyl-10-methoxy-9-(3-methoxypropoxy)-2-oxo-6,7-dihydrobenzo[a]quinolizine-3-carboxylic acid (1.8 g).

Step 4: Preparation of methyl 4-[6-ethyl-10-methoxy-9-(3-methoxypropoxy)-2-oxo-6,7-dihydrobenzo[a]quinolizine-3-carbonyl]morpholine-2-carboxylate

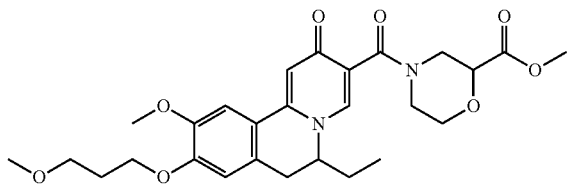

To a solution of 6-ethyl-10-methoxy-9-(3-methoxypropoxy)-2-oxo-6,7-dihydrobenzo[a]quinolizine-3-carboxylic acid (387 mg, 1 mmol) in DMF (10 mL) was added HATU (760 mg, 2 mmol), triethylamine (1 mL) and methyl morpholine-3-carboxylate (290 mg). The resulting solution was stirred at room temperature for 3 h. The mixture was extracted with DCM (30 mL×2). The combined organic layers were washed with brine, and concentrated to give a brown oil which was used to next step without purification.

Step 5: Preparation of 4-[6-ethyl-10-methoxy-9-(3-methoxypropoxy)-2-oxo-6,7-dihydrobenzo[a]quinolizine-3-carbonyl]morpholine-3-carboxylic Acid

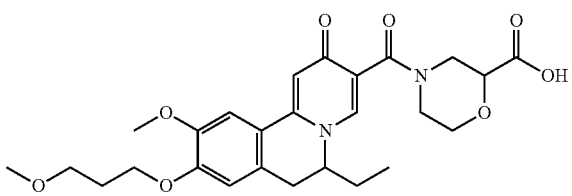 [SMILES: CCC1Cc2cc(OCCCOC)c(OC)cc2-c2cc(=O)c(C(=O)N3CCOC(C(=O)O)C3)cn21]

To a solution of crude methyl 4-[6-ethyl-10-methoxy-9-(3-methoxypropoxy)-2-oxo-6,7-dihydrobenzo[a]quinolizine-3-carbonyl]morpholine-2-carboxylate (514 mg) in THF (15 mL) was added 10% NaOH aqueous solution drop wise at rt. The resultant mixture was stirred for 2 h, and then acidified to pH=1-2 with 2M hydrochloric acid. The mixture was extracted with DCM (20 mL×3), and the combined organic layers were concentrated to give brown solid which was purified with prep-HPLC to afford 4-[6-ethyl-10-methoxy-9-(3-methoxypropoxy)-2-oxo-6,7-dihydrobenzo[a]quinolizine-3-carbonyl]morpholine-3-carboxylic acid (7 mg). $^1$H NMR (400 MHz, MeOD): δ8.11 (s, 1H), 7.39 (s, 1H), 6.98 (d, 2H), 4.32 (m, 2H), 4.21 (m, 3H), 3.94 (m, 3H), 3.86 (m, 2H), 3.63 (m, 6H), 3.33 (s, 3H), 3.02 (m, 1H), 2.11 (m, 2H), 1.59 (m, 2H), 0.92 (t, 3H). MS obsd. (ESI$^+$) [(M+H)$^+$]: 501.

Example 14: 6-ethyl-10-methoxy-9-(3-methoxypropoxy)-2-oxo-N-(1H-tetrazol-5-yl)-6,7-dihydrobenzo[a]quinolizine-3-carboxamide

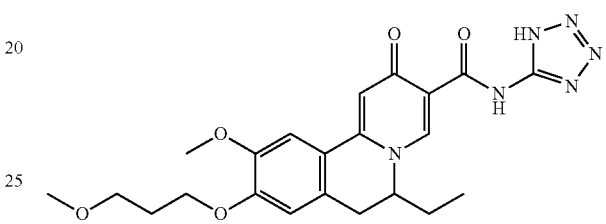

To a solution of 6-ethyl-10-methoxy-9-(3-methoxypropoxy)-2-oxo-6,7-dihydrobenzo[a]quinolizine-3-carboxylic acid (77 mg, 0.2 mmol, example 13, step 3) in DMF (10 mL) was added HATU (114 mg, 0.3 mmol, GL Biochem), triethylamine (100 μL, Aldrich) and 1H-tetrazol-5-amine (85 mg, Accela). The resulting solution was stirred at room temperature for 3 h and then purified by prep-HPLC to afford 6-ethyl-10-methoxy-9-(3-methoxypropoxy)-2-oxo-N-(1H-tetrazol-5-yl)-6,7-dihydrobenzo[a]quinolizine-3-carboxamide (12 mg). $^1$H NMR (400 MHz, MeOD): δ8.83 (s, 1H), 7.43 (m, 1H), 7.17 (s, 1H), 7.00 (s, 1H), 4.56 (m, 2H), 4.18 (m, 2H), 3.96 (s, 3H), 3.61 (t, 2H), 3.33 (m, 4H), 3.02 (d, 1H), 2.11 (m, 2H), 1.65 (m, 2H), 0.92 (t, 3H). MS obsd. (ESI$^+$) [(M+H)$^+$]: 455.

Example 15: N-benzyl-6-ethyl-10-methoxy-9-(3-methoxypropoxy)-2-oxo-6,7-dihydrobenzo[a]quinolizine-3-carboxamide

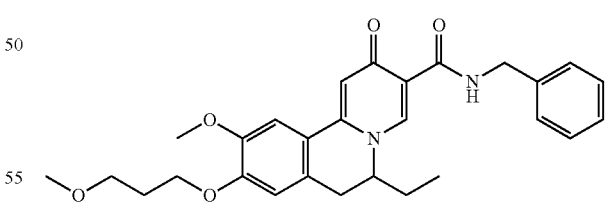

To a solution of 6-ethyl-10-methoxy-9-(3-methoxypropoxy)-2-oxo-6,7-dihydrobenzo[a]quinolizine-3-carboxylic acid (77 mg, 0.2 mmol, example 13, step 3) in DMF (10 mL) was added HATU (114 mg, 0.3 mmol), triethylamine (100 μL) and benzylamine (107 mg). The resulting solution was stirred at room temperature for 3 h and then purified by prep-HPLC to afford N-benzyl-6-ethyl-10-methoxy-9-(3-methoxypropoxy)-2-oxo-6,7-dihydrobenzo[a]quinolizine-3-carboxamide (16 mg). $^1$H NMR (400 MHz, MeOD): δ8.64 (s, 1H), 7.35 (m, 7H), 6.99 (s, 1H), 4.65 (m, 1H), 4.50 (m, 2H), 4.18 (m, 2H), 3.96 (s, 3H), 3.61 (t, 2H), 3.33 (m, 4H), 3.02 (d, 1H), 2.11 (m, 2H), 1.65 (m, 2H), 0.92 (t, 3H). MS obsd. (ESI⁺) [(M+H)⁺]: 477.

Example 16: 6-ethyl-10-methoxy-N-(2-methoxy-1-methyl-ethyl)-9-(3-methoxypropoxy)-2-oxo-6,7-dihydrobenzo[a]quinolizine-3-carboxamide

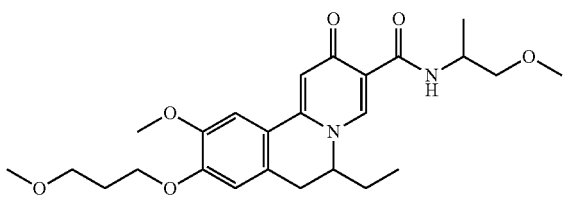

To a solution of 6-ethyl-10-methoxy-9-(3-methoxypropoxy)-2-oxo-6,7-dihydrobenzo[a]quinolizine-3-carboxylic acid (77 mg, 0.2 mmol, example 13, step 3) in DMF (10 mL) was added HATU (114 mg, 0.3 mmol), triethylamine (100 μL) and 1-methoxypropan-2-amine (50 mg). The resulting solution was stirred at room temperature for 3 h and then purified by prep-HPLC to afford 6-ethyl-10-methoxy-N-(2-methoxy-1-methyl-ethyl)-9-(3-methoxypropoxy)-2-oxo-6,7-dihydrobenzo[a]quinolizine-3-carboxamide (21 mg). ¹H NMR (400 MHz, MeOD): δ8.66 (s, 1H), 7.40 (s, 1H), 7.12 (s, 1H), 7.00 (s, 1H), 4.52 (m, 1H), 4.30 (m, 1H), 4.19 (m, 2H), 3.96 (s, 3H), 3.61 (t, 2H), 3.37 (m, 2H), 3.35 (m, 2H), 3.33 (m, 6H), 3.02 (d, 1H), 2.11 (m, 2H), 1.62 (m, 2H), 1.28 (m, 2H), 0.92 (t, 3H). MS obsd. (ESI⁺) [(M+H)⁺]: 459.

Example 17: 9-ethoxy-6-ethyl-10-methoxy-N-(2-methoxy-1-methyl-ethyl)-2-oxo-6,7-dihydrobenzo[a]quinolizine-3-carboxamide

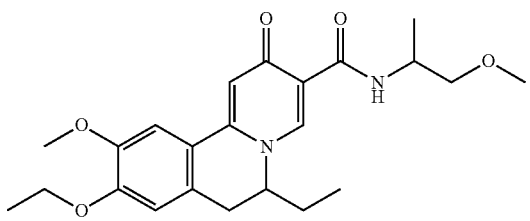 [SMILES: CCOc1cc2c(cc1OC)-c1cc(=O)c(C(=O)NC(C)COC)cn1C(CC)C2]

Step 1: Preparation of ethyl 9-ethoxy-6-ethyl-10-methoxy-2-oxo-6,7-dihydrobenzo[a]quinolizine-3-carboxylate

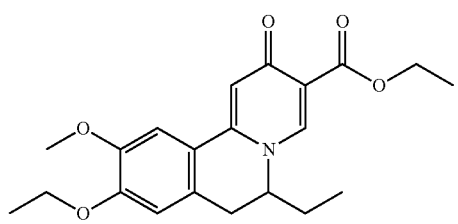 [SMILES: CCOC(=O)c1cn2c(cc1=O)-c1cc(OC)c(OCC)cc1CC2CC]

To a solution of ethyl 6-ethyl-9-hydroxy-10-methoxy-2-oxo-6,7-dihydrobenzo[a]quinolizine-3-carboxylate (170 mg, 0.5 mmol) in DMF (10 mL) was added potassium carbonate (138 mg, 1 mmol) and 1-bromethane (214 mg, 2 mmol). The resultant mixture was stirred at room temperature for 12 h. The mixture was poured into water (20 mL) and the aqueous solution was extracted with EtOAc (20 mL×2). The organic layers were combined and washed with brine, dried over anhydrous Na₂SO₄, and concentrated under reduced pressure to give crude ethyl 9-ethoxy-6-ethyl-10-methoxy-2-oxo-6,7-dihydrobenzo[a]quinolizine-3-carboxylate (180 mg)

Step 2: Preparation of 9-ethoxy-6-ethyl-10-methoxy-2-oxo-6,7-dihydrobenzo[a]quinolizine-3-carboxylic Acid

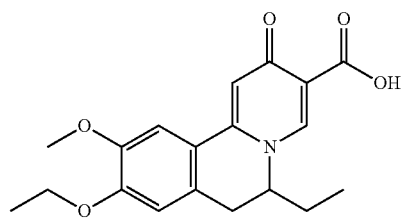 [SMILES: CCOc1cc2c(cc1OC)-c1cc(=O)c(C(=O)O)cn1C(CC)C2]

To a solution of 9-ethoxy-6-ethyl-10-methoxy-2-oxo-6,7-dihydrobenzo[a]quinolizine-3-carboxylic acid (180 mg) in THF (10 mL) was added 10% NaOH aqueous solution drop wise at rt. The resultant mixture was stirred for 2 h, and then acidified to pH=1-2 with 2M hydrochloric acid. The mixture was extracted with DCM (20 mL×2), and the combined organic layers were washed with brine, dried over anhydrous Na₂SO₄ and concentrated to give a light yellow solid, to afford 9-ethoxy-6-ethyl-10-methoxy-2-oxo-6,7-dihydrobenzo[a]quinolizine-3-carboxylic acid (142 mg).

Step 3: Preparation of 9-ethoxy-6-ethyl-10-methoxy-N-(2-methoxy-1-methyl-ethyl)-2-oxo-6,7-dihydrobenzo[a]quinolizine-3-carboxamide

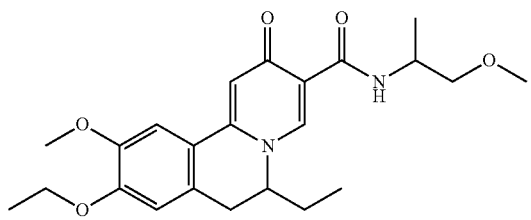 [SMILES: CCOc1cc2c(cc1OC)-c1cc(=O)c(C(=O)NC(C)COC)cn1C(CC)C2]

To a solution of 9-ethoxy-6-ethyl-10-methoxy-2-oxo-6,7-dihydrobenzo[a]quinolizine-3-carboxylic (140 mg, 0.41 mmol) in DMF (10 mL) was added HATU (300 mg, 0.79 mmol), triethylamine (100 μL) and 1-methoxypropan-2-amine (150 mg). The resulting solution was stirred at room temperature for 3 h and then purified by prep-HPLC to afford 9-ethoxy-6-ethyl-10-methoxy-N-(2-methoxy-1-methyl-ethyl)-2-oxo-6,7-dihydrobenzo[a]quinolizine-3-carboxamide (33 mg). ¹HNMR (400 MHz, MeOD): δ8.59 (s, 1H), 7.38 (s, 1H), 7.03 (s, 2H), 4.60 (m, 2H), 4.47 (m, 2H), 3.95 (s, 3H), 3.42 (m, 3H), 3.29 (m, 1H), 3.01 (d, 1H), 2.05

(s, 2H), 1.62 (m, 2H), 1.47 (t, 2H), 1.29 (m, 2H), 0.92 (t, 3H), 0.86 (t, 2H). MS obsd. (ESI+) [(M+H)+]: 415.

Example 18: 6-ethyl-9-isobutoxy-10-methoxy-N-(2-methoxy-1-methyl-ethyl)-2-oxo-6,7-dihydrobenzo[a]quinolizine-3-carboxamide

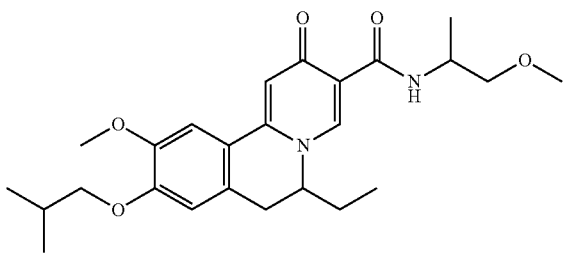 [SMILES: CCC1Cc2cc(OCC(C)C)c(OC)cc2-c2cc(=O)c(C(=O)NC(C)COC)cn21]

Step 1: Preparation of ethyl 6-ethyl-9-isobutoxy-10-methoxy-2-oxo-6,7-dihydrobenzo[a]quinolizine-3-carboxylate

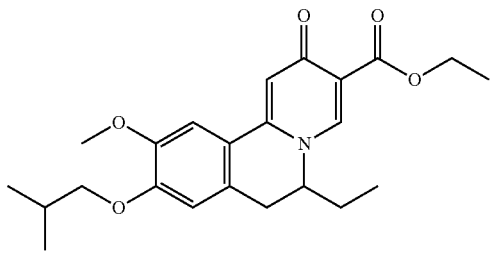 [SMILES: CCOC(=O)c1cn2c(cc1=O)-c1cc(OC)c(OCC(C)C)cc1CC2CC]

To a solution of ethyl 6-ethyl-9-hydroxy-10-methoxy-2-oxo-6,7-dihydrobenzo[a]quinolizine-3-carboxylate (170 mg, 0.5 mmol) in DMF (10 mL) was added potassium carbonate (138 mg, 1 mmol) and 1-bromo-2-methyl-propane (270 mg, 2 mmol, TCI). The resultant mixture was stirred at room temperature for 12 h. The mixture was poured into water (20 mL) and the aqueous solution was extracted with EtOAc (20 mL×2). The organic layers were combined and washed with brine, dried over anhydrous Na$_2$SO$_4$, and concentrated under reduced pressure to give crude 6-ethyl-9-isobutoxy-10-methoxy-N-(2-methoxy-1-methyl-ethyl)-2-oxo-6,7-dihydrobenzo[a]quinolizine-3-carboxamide (192 mg)

Step 2: Preparation of 6-ethyl-9-isobutoxy-10-methoxy-2-oxo-6,7-dihydrobenzo[a]quinolizine-3-carboxylic Acid

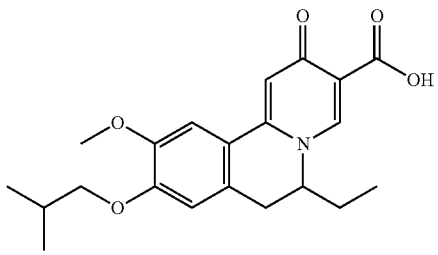 [SMILES: CCC1Cc2cc(OCC(C)C)c(OC)cc2-c2cc(=O)c(C(=O)O)cn21]

To a solution of 6-ethyl-9-isobutoxy-10-methoxy-N-(2-methoxy-1-methyl-ethyl)-2-oxo-6,7-dihydrobenzo[a]quinolizine-3-carboxamide (192 mg) in THF (10 mL) was added 10% NaOH aqueous solution drop wise at rt. The resultant mixture was stirred for 2 h, and then acidified to pH=1-2 with 2M hydrochloric acid. The mixture was extracted with DCM (20 mL×2), and the combined organic layers were washed with brine, dried over anhydrous Na$_2$SO$_4$ and concentrated to afford 6-ethyl-9-isobutoxy-10-methoxy-2-oxo-6,7-dihydrobenzo[a]quinolizine-3-carboxylic acid (132 mg).

Step 3: Preparation of 6-ethyl-9-isobutoxy-10-methoxy-N-(2-methoxy-1-methyl-ethyl)-2-oxo-6,7-dihydrobenzo[a]quinolizine-3-carboxamide

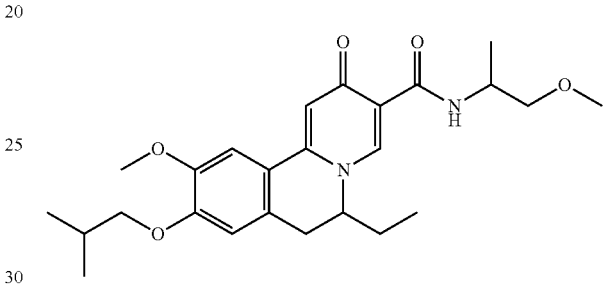

To a solution of 6-ethyl-9-isobutoxy-10-methoxy-2-oxo-6,7-dihydrobenzo[a]quinolizine-3-carboxylic acid (132 mg, 0.36 mmol) in DMF (10 mL) was added HATU (300 mg, 0.79 mmol), triethylamine (100 µL) and 1-methoxypropan-2-amine (150 mg). The resulting solution was stirred at room temperature for 3 h and then purified by prep-HPLC to afford 6-ethyl-9-isobutoxy-10-methoxy-N-(2-methoxy-1-methyl-ethyl)-2-oxo-6,7-dihydrobenzo[a]quinolizine-3-carboxamide (28 mg). $^1$HNMR (400 MHz, MeOD): δ8.60 (s, 1H), 7.35 (s, 1H), 7.06 (s, 1H), 6.97 (s, 1H), 4.47 (m, 1H), 4.28 (m, 1H), 3.97 (s, 3H), 3.84 (m, 2H), 3.45 (m, 2H), 3.39 (s, 3H), 3.01 (d, 1H), 2.15 (s, 1H), 1.62 (m, 2H), 1.29 (m, 3H), 0.92 (d, 2H), 0.88 (t, 3H). MS obsd. (ESI+) [(M+H)+]: 443.

Example 19: 9-(cyclopropylmethoxy)-6-ethyl-10-methoxy-N-(2-methoxy-1-methyl-ethyl)-2-oxo-6,7-dihydrobenzo[a]quinolizine-3-carboxamide

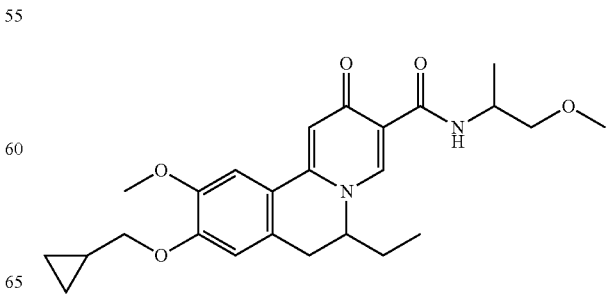

Step 1: Preparation of ethyl 9-(cyclopropyl-methoxy)-6-ethyl-10-methoxy-2-oxo-6,7-dihydrobenzo[a]quinolizine-3-carboxylate

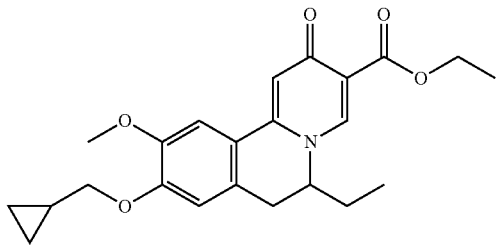 [SMILES: CCOC(=O)c1cn2c(cc1=O)-c1cc(OC)c(OCC3CC3)cc1CC2CC]

To a solution of ethyl 6-ethyl-9-hydroxy-10-methoxy-2-oxo-6,7-dihydrobenzo[a]quinolizine-3-carboxylate (170 mg, 0.5 mmol) in DMF (10 mL) was added potassium carbonate (138 mg, 1 mmol) and bromomethylcyclopropane (260 mg, 2 mmol, J&K). The resultant mixture was stirred at room temperature for 12 h. The mixture was poured into water (20 mL) and the aqueous solution was extracted with EtOAc (20 mL×2). The organic layers were combined and washed with brine, dried over anhydrous $Na_2SO_4$, and concentrated under reduced pressure to give crude ethyl 9-(cyclopropylmethoxy)-6-ethyl-10-methoxy-2-oxo-6,7-dihydrobenzo[a]quinolizine-3-carboxylate (194 mg).

Step 2: Preparation of 9-(cyclopropylmethoxy)-6-ethyl-10-methoxy-2-oxo-6,7-dihydrobenzo[a]quinolizine-3-carboxylic Acid

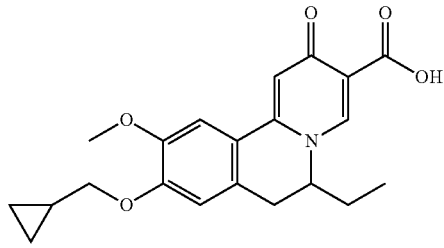 [SMILES: CCC1Cc2cc(OCC3CC3)c(OC)cc2-c2cc(=O)c(C(=O)O)cn21]

To a solution of ethyl 9-(cyclopropylmethoxy)-6-ethyl-10-methoxy-2-oxo-6,7-dihydrobenzo[a]quinolizine-3-carboxylate (194 mg) in THF (10 mL) was added 10% NaOH aqueous solution drop wise at rt. The resultant mixture was stirred for 2 h, and then acidified to pH=1-2 with 2M hydrochloric acid. The mixture was extracted with DCM (20 mL×2), and the combined organic layers were washed with brine, dried over anhydrous $Na_2SO_4$ and concentrated to afford 9-(cyclopropylmethoxy)-6-ethyl-10-methoxy-2-oxo-6,7-dihydrobenzo[a]quinolizine-3-carboxylic acid (122 mg).

Step 3: Preparation of 9-(cyclopropylmethoxy)-6-ethyl-10-methoxy-N-(2-methoxy-1-methyl-ethyl)-2-oxo-6,7-dihydrobenzo[a]quinolizine-3-carboxamide

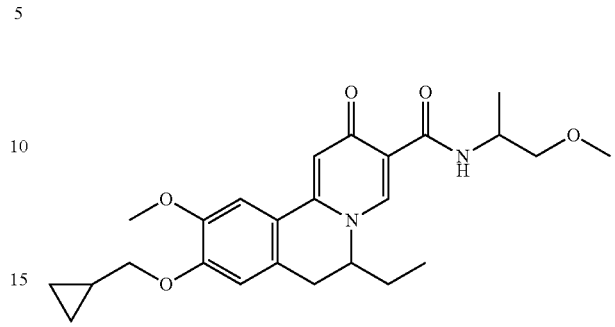

To a solution of 9-(cyclopropylmethoxy)-6-ethyl-10-methoxy-2-oxo-6,7-dihydrobenzo[a]quinolizine-3-carboxylic acid (122 mg, 0.33 mmol) in DMF (10 mL) was added HATU (300 mg, 0.79 mmol), triethylamine (100 µL) and 1-methoxypropan-2-amine (150 mg). The resulting solution was stirred at room temperature for 3 h and then purified by prep-HPLC to afford 9-(cyclopropylmethoxy)-6-ethyl-10-methoxy-N-(2-methoxy-1-methyl-ethyl)-2-oxo-6,7-dihydrobenzo[a]quinolizine-3-carboxamide (19 mg). $^1$HNMR (400 MHz, MeOD): δ8.61 (s, 1H), 7.39 (s, 1H), 7.06 (s, 1H), 6.95 (s, 1H), 4.47 (m, 1H), 4.28 (m, 1H), 3.98 (s, 3H), 3.45 (m, 2H), 3.40 (s, 3H), 3.02 (d, 1H), 1.62 (m, 2H), 1.29 (m, 3H), 0.92 (t, 3H), 0.66 (m, 2H), 0.41 (m, 2H). MS obsd. (ESI$^+$) [(M+H)$^+$]: 441.

Example 20: 6-ethyl-3-(hydroxymethyl)-10-methoxy-9-(3-methoxy-propoxy)-6,7-dihydrobenzo[a]quinolizin-2-one

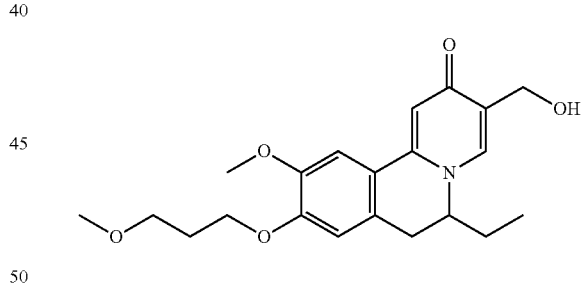

To a solution of ethyl-6-ethyl-10-methoxy-9-(3-methoxy-propoxy)-2-oxo-6,7-dihydrobenzo[a]quinolizine-3-carboxylate (3.92 g, 9.4 mmol) in THF (30 mL) was added 1M DIBAL-H solution in toluene (20 mL, 20 mmol, Aldrich). The resultant mixture was stirred at room temperature for 2 h. The reaction was quenched with methanol and acidified with 1M aqueous HCl (10 mL). The aqueous solution was extracted with ethyl acetate (2×30 mL). The organic layers were combined and washed with brine, dried over anhydrous $Na_2SO_4$ and filtered. The filtrate was concentrated to give 6-ethyl-3-(hydroxymethyl)-10-methoxy-9-(3-methoxy-propoxy)-6,7-dihydrobenzo[a]quinolizin-2-one (2.8 g). $^1$H NMR (400 MHz, MeOD): 7.58 (s, 1H), 7.33 (s, 1H), 6.95 (d, 2H), 4.25 (m, 1H), 4.17 (m, 2H), 3.94 (s, 3H), 3.60 (t, 3H), 3.33 (m, 4H), 3.01 (d, 1H), 2.11 (s, 2H), 1.56 (m, 3H), 0.98 (t, 3H). MS obsd. (ESI$^+$) [(M+H)$^+$]: 374.

Example 21: 4-[[6-ethyl-10-methoxy-9-(3-methoxypropoxy)-2-oxo-6,7-dihydrobenzo[a]quinolizin-3-yl]methyl]morpholine-3-carboxylic Acid

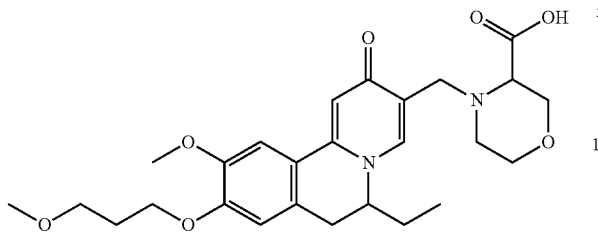

Step 1: Preparation of 3-(chloromethyl)-6-ethyl-10-methoxy-9-(3-methoxypropoxy)-6,7-dihydrobenzo[a]quinolizin-2-one

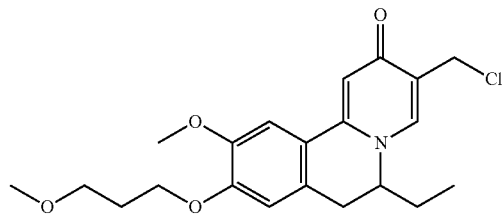 [SMILES: CCC1Cc2cc(OCCCOC)c(OC)cc2-c2cc(=O)c(CCl)cn21]

To a solution of 6-ethyl-3-(hydroxymethyl)-10-methoxy-9-(3-methoxy-propoxy)-6,7-dihydrobenzo[a]quinolizin-2-one (2.8 g) in dichloromethane (30 mL) was added thionyl chloride (5 mL) at room temperature for 3 h. The mixture was concentrated in vacuo to give 3-(chloromethyl)-6-ethyl-10-methoxy-9-(3-methoxypropoxy)-6,7-dihydrobenzo[a]quinolizin-2-one as a brown oil which was used in next step without purification.

Step 2: Preparation of methyl 4-[[6-ethyl-10-methoxy-9-(3-methoxypropoxy)-2-oxo-6,7-dihydrobenzo[a]quinolizin-3-yl]methyl]morpholine-3-carboxylate

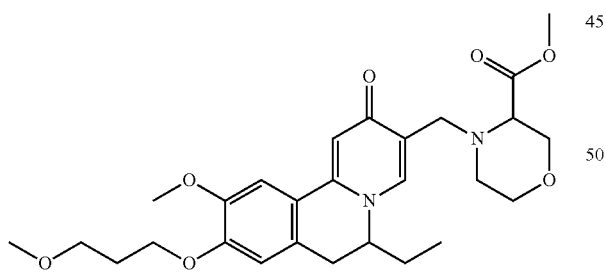

To a solution of 3-(chloromethyl)-6-ethyl-10-methoxy-9-(3-methoxypropoxy)-6,7-dihydrobenzo[a]quinolizin-2-one (78 mg) in dichloromethane (10 mL) was added methyl morpholine-3-carboxylate (43 mg) and triethylamine (150 μL). The resulting solution was stirred at room temperature overnight and then quenched with water (20 mL). The aqueous solution was extracted with dichloromethane (2×15 mL). The organic layers were combined and concentrated to give methyl 4-[[6-ethyl-10-methoxy-9-(3-methoxypropoxy)-2-oxo-6,7-dihydrobenzo[a]quinolizin-3-yl]methyl]morpholine-3-carboxylate (100 mg).

Step 3: Preparation of 4-[[6-ethyl-10-methoxy-9-(3-methoxypropoxy)-2-oxo-6,7-dihydrobenzo[a]quinolizin-3-yl]methyl]morpholine-3-carboxylic Acid

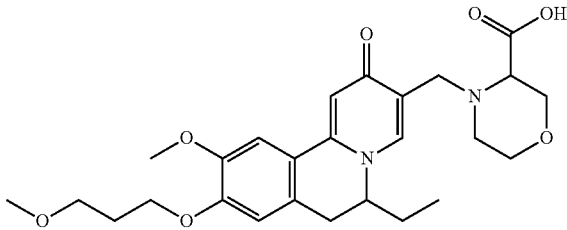

To a solution of crude methyl 4-[[6-ethyl-10-methoxy-9-(3-methoxypropoxy)-2-oxo-6,7-dihydrobenzo[a]quinolizin-3-yl]methyl]morpholine-3-carboxylate (100 mg) in THF (10 mL) was added 10% NaOH aqueous solution drop wise at rt. The resultant mixture was stirred for 2 h, and then acidified to pH=1-2 with 2M hydrochloric acid. The mixture was extracted with DCM (20 mL×2), and the combined organic layers were washed with brine, dried over anhydrous Na$_2$SO$_4$ and concentrated. The residue was purified by prep-HPLC to afford 4-[[6-ethyl-10-methoxy-9-(3-methoxypropoxy)-2-oxo-6,7-dihydrobenzo[a]quinolizin-3-yl]methyl]morpholine-3-carboxylic acid (7 mg). $^1$H NMR (400 MHz, MeOD): δ8.12 (d, 1H), 7.38 (s, 1H), 6.98 (d, 2H), 4.35 (m, 2H), 4.19 (m, 4H), 3.95 (m, 3H), 3.86 (m, 2H), 3.74 (m, 2H), 3.63 (m, 3H), 3.43 (m, 1H), 3.33 (m, 3H), 3.05 (m, 2H), 2.11 (m, 2H), 1.62 (m, 2H), 0.92 (t, 3H). MS obsd. (ESI$^+$) [(M+H)$^+$]: 487.

Example 22: 1-[[6-ethyl-10-methoxy-9-(3-methoxypropoxy)-2-oxo-6,7-dihydrobenzo[a]quinolizin-3-yl]methyl]piperidine-2-carboxylic Acid

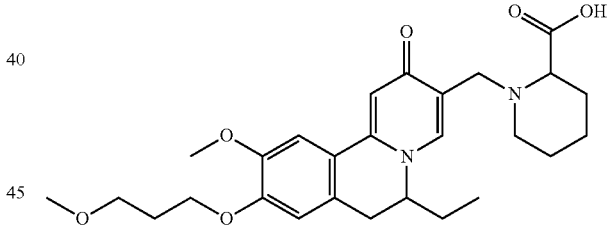

Step 1: Preparation of methyl 1-[[6-ethyl-10-methoxy-9-(3-methoxypropoxy)-2-oxo-6,7-dihydrobenzo[a]quinolizin-3-yl]methyl]piperidine-2-carboxylate

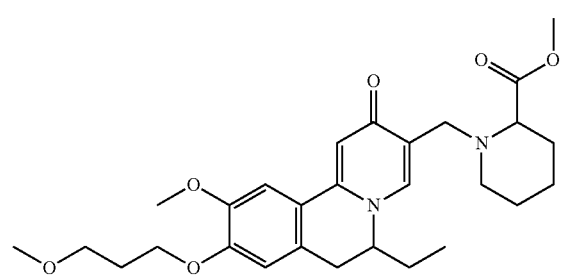

To a solution of 3-(chloromethyl)-6-ethyl-10-methoxy-9-(3-methoxypropoxy)-6,7-dihydrobenzo[a]quinolizin-2-one (78 mg) in dichloromethane (10 mL) was methyl piperidine-2-carboxylate (42 mg) and triethylamine (150 μL). The resulting solution was stirred at room temperature overnight and then quenched with water (20 mL). The aqueous solution was extracted with dichloromethane (2×15 mL). The organic layers were combined and concentrated to give methyl 1-[[6-ethyl-10-methoxy-9-(3-methoxypropoxy)-2-oxo-6,7-dihydrobenzo[a]quinolizin-3-yl]methyl]piperidine-2-carboxylate (98 mg).

Step 2: Preparation of 1-[[6-ethyl-10-methoxy-9-(3-methoxypropoxy)-2-oxo-6,7-dihydrobenzo[a]quinolizin-3-yl]methyl]piperidine-2-carboxylic Acid

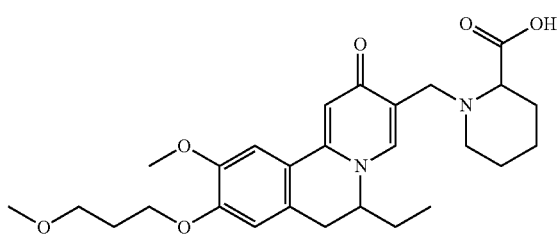 [SMILES: CCC1Cc2cc(OCCCOC)c(OC)cc2-c2cc(=O)c(CN3CCCCC3C(=O)O)cn21]

To a solution of crude methyl 4-[[6-ethyl-10-methoxy-9-(3-methoxypropoxy)-2-oxo-6,7-dihydrobenzo[a]quinolizin-3-yl]methyl]piperidine-3-carboxylate (98 mg) in THF (10 mL) was added 10% NaOH aqueous solution drop wise at rt. The resultant mixture was stirred for 2 h, and then acidified to pH=1-2 with 2M hydrochloric acid. The mixture was extracted with DCM (20 mL×2), and the combined organic layers were washed with brine, dried over anhydrous Na$_2$SO$_4$ and concentrated to give an oil which was purified by prep-HPLC to afford 4-[[6-ethyl-10-methoxy-9-(3-methoxypropoxy)-2-oxo-6,7-dihydrobenzo[a]quinolizin-3-yl]methyl]piperidine-3-carboxylic acid (5 mg). $^1$H NMR (400 MHz, MeOD): δ 8.11 (s, 1H), 7.35 (s, 1H), 6.95 (d, 2H), 4.36 (m, 3H), 4.19 (m, 2H), 3.95 (s, 3H), 3.63 (m, 4H), 3.33 (m, 3H), 3.10 (m, 2H), 2.11 (m, 3H), 1.97 (m, 4H), 1.62 (m, 4H), 0.92 (t, 3H). MS obsd. (ESI$^+$) [(M+H)$^+$]: 485.

Example 23: 1-[[6-ethyl-10-methoxy-9-(3-methoxypropoxy)-2-oxo-6,7-dihydrobenzo[a]quinolizin-3-yl]methyl]pyrrolidine-2-carboxylic Acid

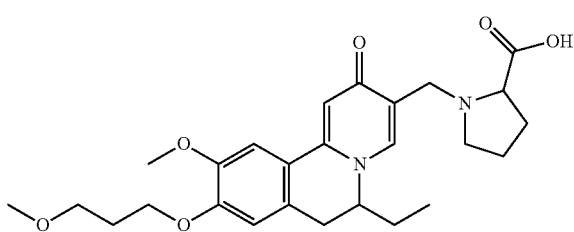 [SMILES: CCC1Cc2cc(OCCCOC)c(OC)cc2-c2cc(=O)c(CN3CCCC3C(=O)O)cn21]

Step 1: Preparation of methyl 1-[[6-ethyl-10-methoxy-9-(3-methoxypropoxy)-2-oxo-6,7-dihydrobenzo[a]quinolizin-3-yl]methyl]pyrrolidine-2-carboxylate

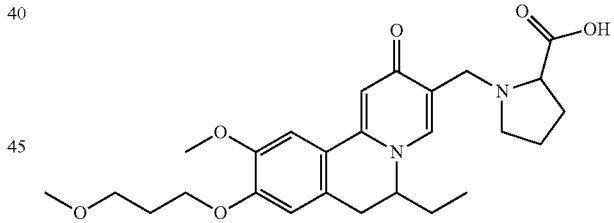

To a solution of 3-(chloromethyl)-6-ethyl-10-methoxy-9-(3-methoxypropoxy)-6,7-dihydrobenzo[a]quinolizin-2-one (78 mg) in dichloromethane (10 mL) was added methyl pyrrolidine-2-carboxylate (38 mg) and triethylamine (150 μL). The resulting solution was stirred at room temperature overnight and then quenched with water (20 mL). The aqueous solution was extracted with dichloromethane (2×15 mL). The organic layers were combined and concentrated to give methyl 1-[[6-ethyl-10-methoxy-9-(3-methoxypropoxy)-2-oxo-6,7-dihydrobenzo[a]quinolizin-3-yl]methyl]pyrrolidine-2-carboxylate (97 mg).

Step 2: Preparation of 1-[[6-ethyl-10-methoxy-9-(3-methoxypropoxy)-2-oxo-6,7-dihydrobenzo[a]quinolizin-3-yl]methyl]pyrrolidine-2-carboxylic Acid To a solution of crude methyl 1-[[6-ethyl-10-methoxy-9-(3-methoxypropoxy)-2-oxo-6,7-dihydrobenzo[a]quinolizin-3-yl]methyl]pyrrolidine-2-carboxylate (97 mg) in THF (10 mL) was added 10% NaOH aqueous solution drop wise at rt. The resultant mixture was stirred for 2 h, and then acidified to pH=1-2 with 2M hydrochloric acid. The mixture was extracted with DCM (20 mL×2), and the combined organic layers were washed with brine, dried over anhydrous Na$_2$SO$_4$ and concentrated to give an oil which was purified by prep-HPLC to afford 1-[[6-ethyl-10-methoxy-9-(3-methoxypropoxy)-2-oxo-6,7-dihydrobenzo[a]quinolizin-3-yl]methyl]pyrrolidine-2-carboxylic acid (14 mg). $^1$H NMR (400 MHz, MeOD): δ8.10 (s, 1H), 7.34 (s, 1H), 6.93 (d, 2H), 4.31 (m, 5H), 4.16 (m, 1H), 3.94 (s, 3H), 3.75 (m, 1H), 3.61 (t, 2H), 3.33 (m, 3H), 3.03 (m, 2H), 2.45 (m, 1H), 2.24 (m, 1H), 2.11 (s, 3H), 1.97 (m, 1H), 1.58 (m, 2H), 0.92 (t, 3H). MS obsd. (ESI$^+$) [(M+H)$^+$]: 471.

Example 24: 6-ethyl-10-methoxy-9-(3-methoxypropoxy)-3-(1-piperidylmethyl)-6,7-dihydrobenzo[a]quinolizin-2-one

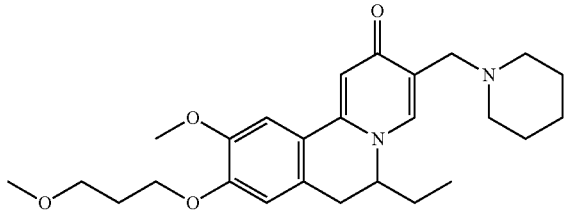 [SMILES: CCC1Cc2cc(OCCCOC)c(OC)cc2-c2cc(=O)c(CN3CCCCC3)cn21]

To a solution of 3-(chloromethyl)-6-ethyl-10-methoxy-9-(3-methoxypropoxy)-6,7-dihydrobenzo[a]quinolizin-2-one (78 mg) in dichloromethane (10 mL) was added piperidine (30 mg) and triethylamine (150 μL). The resulting solution was stirred at room temperature overnight and then quenched with water (20 mL). The aqueous solution was extracted with dichloromethane (2×15 mL). The organic layers were combined and concentrated to give an oil which was purified by prep-HPLC to afford 6-ethyl-10-methoxy-9-(3-methoxypropoxy)-3-(1-piperidylmethyl)-6,7-dihydrobenzo[a]quinolizin-2-one (25 mg). $^1$H NMR (400 MHz, MeOD): δ 7.90 (s, 1H), 7.36 (s, 1H), 6.95 (s, 1H), 6.89 (s, 1H), 4.34 (m, 1H), 4.17 (m, 2H), 3.94 (s, 3H), 3.59 (m, 2H), 3.49 (m, 2H), 3.33 (m, 3H), 3.02 (d, 1H), 2.55 (m, 4H), 2.09 (m, 2H), 1.64 (m, 9H), 0.92 (t, 3H). MS obsd. (ESI$^+$) [(M+H)$^+$]: 441.

Example 25: 6-ethyl-10-methoxy-9-(3-methoxypropoxy)-3-(pyrrolidin-1-ylmethyl)-6,7-dihydrobenzo[a]quinolizin-2-one

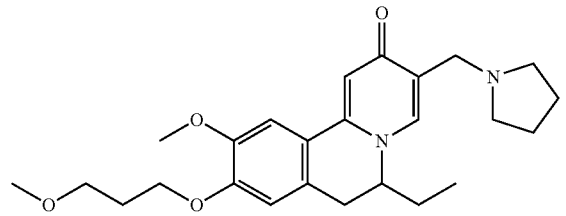 [SMILES: CCC1Cc2cc(OCCCOC)c(OC)cc2-c2cc(=O)c(CN3CCCC3)cn21]

To a solution of 3-(chloromethyl)-6-ethyl-10-methoxy-9-(3-methoxypropoxy)-6,7-dihydrobenzo[a]quinolizin-2-one (78 mg) in dichloromethane (10 mL) was added pyrrolidine (28 mg) and triethylamine (150 μL). The resulting solution was stirred at room temperature overnight and then quenched with water (20 mL). The aqueous solution was extracted with dichloromethane (2×15 mL). The organic layers were combined and concentrated to give an oil which was purified by prep-HPLC to afford 6-ethyl-10-methoxy-9-(3-methoxypropoxy)-3-(pyrrolidin-1-ylmethyl)-6,7-dihydrobenzo[a]quinolizin-2-one (26 mg). $^1$H NMR (400 MHz, MeOD): δ 7.89 (s, 1H), 7.36 (s, 1H), 6.96 (s, 1H), 6.91 (s, 1H), 4.34 (m, 1H), 4.18 (m, 2H), 3.94 (s, 3H), 3.63 (m, 4H), 3.33 (s, 3H), 3.02 (d, 1H), 2.72 (m, 4H), 2.09 (m, 2H), 1.88 (m, 4H), 1.64 (m, 2H), 0.97 (t, 3H). MS obsd. (ESI$^+$) [(M+H)$^+$]: 427.

Example 26: 6-ethyl-10-methoxy-9-(3-methoxypropoxy)-3-(morpholinomethyl)-6,7-dihydrobenzo[a]quinolizin-2-one

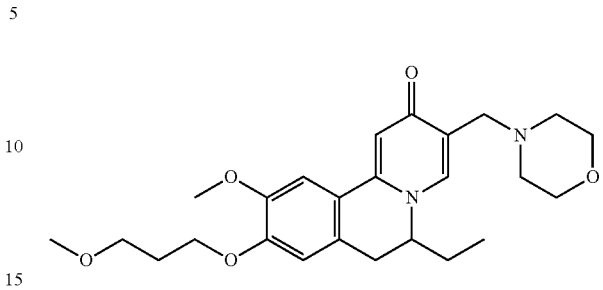

To a solution of 3-(chloromethyl)-6-ethyl-10-methoxy-9-(3-methoxypropoxy)-6,7-dihydrobenzo[a]quinolizin-2-one (78 mg) in dichloromethane (10 mL) was added morpholine (32 mg) and triethylamine (150 μL). The resulting solution was stirred at room temperature overnight and then quenched with water (20 mL). The aqueous solution was extracted with dichloromethane (2×15 mL). The organic layers were combined and concentrated to give an oil which was purified by prep-HPLC to afford 6-ethyl-10-methoxy-9-(3-methoxypropoxy)-3-(morpholinomethyl)-6,7-dihydrobenzo[a]quinolizin-2-one (25 mg). $^1$H NMR (400 MHz, MeOD): δ 7.91 (s, 1H), 7.36 (m, 1H), 6.94 (d, 2H), 4.36 (m, 1H), 4.17 (m, 2H), 3.94 (s, 3H), 3.74 (m, 4H) 3.61 (t, 2H), 3.42 (m, 2H), 3.33 (m, 4H), 3.02 (d, 1H), 2.56 (m, 4H), 2.11 (m, 2H), 1.65 (m, 2H), 0.92 (t, 3H). MS obsd. (ESI$^+$) [(M+H)$^+$]: 443.

Example 27: 6-ethyl-10-methoxy-9-(3-methoxypropoxy)-3-(methylaminomethyl)-6,7-dihydrobenzo[a]quinolizin-2-one

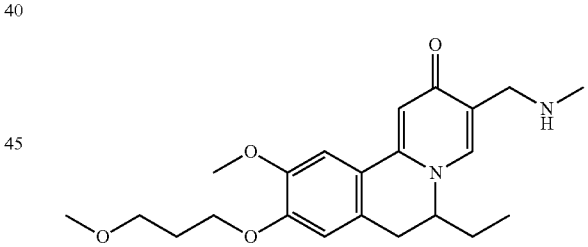

To a solution of 3-(chloromethyl)-6-ethyl-10-methoxy-9-(3-methoxypropoxy)-6,7-dihydrobenzo[a]quinolizin-2-one (78 mg) in dichloromethane (10 mL) was added methylamine hydrochloride (67 mg) and triethylamine (150 μL). The resulting solution was stirred at room temperature overnight and then quenched with water (20 mL). The aqueous solution was extracted with dichloromethane (2×15 mL). The organic layers were combined and concentrated to give an oil which was purified by prep-HPLC to afford 6-ethyl-10-methoxy-9-(3-methoxypropoxy)-3-(methylaminomethyl)-6,7-dihydrobenzo[a]quinolizin-2-one (5.3 mg). $^1$H NMR (400 MHz, MeOD): δ 7.92 (s, 1H), 7.37 (s, 1H), 6.95 (d, 2H), 4.31 (m, 1H), 4.17 (m, 2H), 3.94 (s, 3H), 3.61 (m, 4H), 3.74 (s, 2H), 3.61 (t, 3H), 3.33 (m, 4H), 3.02 (d, 1H), 2.50 (s, 3H), 2.11 (m, 2H), 1.60 (m, 2H), 0.92 (t, 3H). MS obsd. (ESI$^+$) [(M+H)$^+$]: 387.

Example 28: 3-[(dimethylamino)methyl]-6-ethyl-10-methoxy-9-(3-methoxypropoxy)-6,7-dihydrobenzo[a]quinolizin-2-one

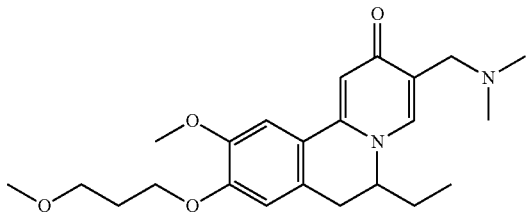

To a solution of 3-(chloromethyl)-6-ethyl-10-methoxy-9-(3-methoxypropoxy)-6,7-dihydrobenzo[a]quinolizin-2-one (78 mg) in dichloromethane (10 mL) was added N,N-dimethylamine hydrochloride (81 mg) and triethylamine (150 µL). The resulting solution was stirred at room temperature overnight and then quenched with water (20 mL). The aqueous solution was extracted with dichloromethane (2×15 mL). The organic layers were combined and concentrated to give an oil which was purified by prep-HPLC to afford 3-[(dimethylamino)methyl]-6-ethyl-10-methoxy-9-(3-methoxypropoxy)-6,7-dihydrobenzo[a]quinolizin-2-one (12 mg). $^1$H NMR (400 MHz, MeOD): δ 7.93 (s, 1H), 7.38 (s, 1H), 6.95 (d, 2H), 4.33 (m, 1H), 4.19 (m, 2H), 3.94 (s, 3H), 3.61 (m, 4H), 3.33 (m, 4H), 3.02 (d, 1H), 2.84 (s, 6H), 2.11 (m, 2H), 1.63 (m, 2H), 0.92 (t, 3H). MS obsd. (ESI$^+$) [(M+H)$^+$]: 401.

Example 29: 6-ethyl-10-methoxy-3-(methoxymethyl)-9-(3-methoxypropoxy)-6,7-dihydrobenzo[a]quinolizin-2-one

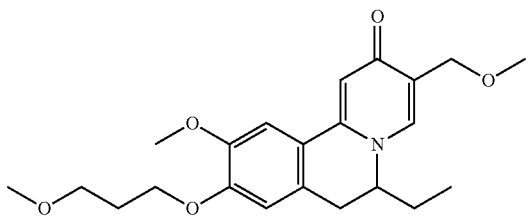

To a solution of 3-(chloromethyl)-6-ethyl-10-methoxy-9-(3-methoxypropoxy)-6,7-dihydrobenzo[a]quinolizin-2-one (78 mg) in methanol (10 mL) was added triethylamine (150 µL). The resulting solution was stirred at room temperature overnight and then quenched with water (20 mL). The aqueous solution was extracted with dichloromethane (2×15 mL). The organic layers were combined and concentrated to give an oil which was purified by prep-HPLC to afford 6-ethyl-10-methoxy-3-(methoxymethyl)-9-(3-methoxypropoxy)-6,7-dihydrobenzo[a]quinolizin-2-one (11 mg). $^1$H NMR (400 MHz, MeOD): δ8.05 (s, 1H), 7.39 (s, 1H), 6.99 (d, 2H), 4.43 (m, 3H), 4.17 (m, 2H), 3.95 (s, 3H), 3.61 (t, 3H), 3.43 (s, 3H), 3.33 (s, 3H), 3.06 (d, 1H), 2.11 (m, 2H), 1.64 (m, 2H), 0.93 (t, 3H). MS obsd. (ESI$^+$) [(M+H)$^+$]: 388.

Example 30: 2-[[6-ethyl-10-methoxy-9-(3-methoxypropoxy)-2-oxo-6,7-dihydrobenzo[a]quinolizin-3-yl]methyl-methyl-amino]acetic Acid

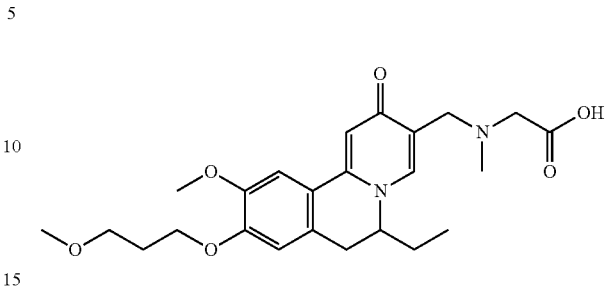

Step 1: Preparation of methyl 2-[[6-ethyl-10-methoxy-9-(3-methoxypropoxy)-2-oxo-6,7-dihydrobenzo[a]quinolizin-3-yl]methyl-methyl-amino]acetate

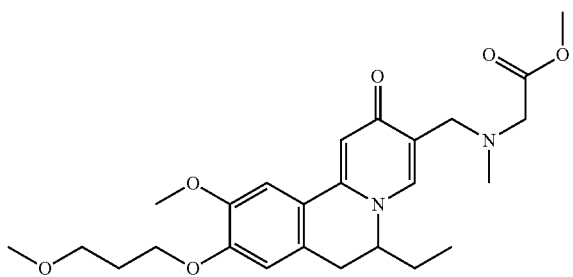

To a solution of 3-(chloromethyl)-6-ethyl-10-methoxy-9-(3-methoxypropoxy)-6,7-dihydrobenzo[a]quinolizin-2-one (78 mg) in dichloromethane (10 mL) was added methyl 2-(methylamino)acetate (31 mg) and triethylamine (150 µL). The resulting solution was stirred at room temperature overnight and then quenched with water (20 mL). The aqueous solution was extracted with dichloromethane (2×15 mL). The organic layers were combined and concentrated to give methyl 2-[[6-ethyl-10-methoxy-9-(3-methoxypropoxy)-2-oxo-6,7-dihydrobenzo[a]quinolizin-3-yl]methyl-methyl-amino]acetate (92 mg).

Step 2: Preparation of 2-[[6-ethyl-10-methoxy-9-(3-methoxypropoxy)-2-oxo-6,7-dihydrobenzo[a]quinolizin-3-yl]methyl-methyl-amino]acetic Acid

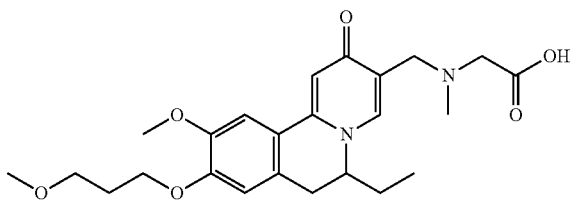 [SMILES: CCC1Cc2cc(OCCCOC)c(OC)cc2-c2cc(=O)c(CN(C)CC(=O)O)cn21]

To a solution of crude methyl 2-[[6-ethyl-10-methoxy-9-(3-methoxypropoxy)-2-oxo-6,7-dihydrobenzo[a]quinolizin-3-yl]methyl-methyl-amino]acetate (92 mg) in THF (10 mL) was added 10% NaOH aqueous solution drop wise at rt. The resultant mixture was stirred for 2 h, and then acidified to pH=1-2 with 2M hydrochloric acid. The mixture was extracted with DCM (20 mL×2), and the combined organic layers were washed with brine, dried over anhydrous Na$_2$SO$_4$ and concentrated to give an oil which was purified by prep-HPLC to afford 2-[[6-ethyl-10-methoxy-9-(3-methoxypropoxy)-2-oxo-6,7-dihydrobenzo[a]quinolizin-3-yl]methyl-methyl-amino]acetic acid (11 mg). $^1$H NMR (400 MHz, MeOD): δ8.08 (s, 1H), 7.37 (s, 1H), 6.96 (d, 2H), 4.36 (m, 3H), 4.19 (m, 2H), 3.94 (s, 3H), 3.63 (m, 4H), 3.33 (m, 3H), 3.03 (m, 2H), 2.97 (s, 3H), 2.11 (m, 2H), 1.62 (m, 2H), 0.92 (t, 3H). MS obsd. (ESI$^+$) [(M+H)$^+$]: 445.

Example 31: (6R)-6-ethyl-9,10-dimethoxy-2-oxo-N-(1H-tetrazol-5-yl)-6,7-dihydrobenzo[a]quinolizine-3-carboxamide

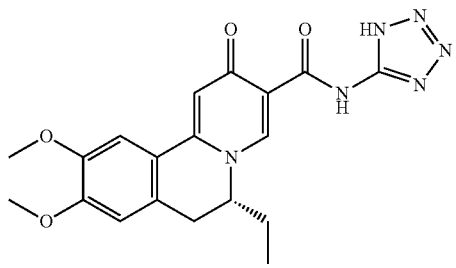 [SMILES: CC[C@@H]1Cc2cc(OC)c(OC)cc2-c2cc(=O)c(C(=O)Nc3nnn[nH]3)cn21]

Step 1: Preparation of 1,2-dimethoxy-4-[2-nitrobut-1-enyl]benzene

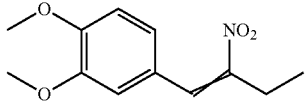 [SMILES: CCC(=Cc1ccc(OC)c(OC)c1)[N+](=O)[O-]]

A mixture of 3,4-dimethoxybenzaldehyde (112.5 g, 677 mmol), nitropropane (122 g, 1.37 mol), dimethylamine HCl (164 g, 2.33 mol) and potassium fluoride (39.1 g, 677 mmol) in toluene (1500 mL) was refluxed with a Dean-Stark trap for 20 hours. Then the reaction mixture was diluted with ethyl acetate (800 mL) and then quenched with 10% hydrochloric acid (250 mL). The organic layer was separated, and then washed with water (250 mL) and brine (250 mL), then dried over anhydrous Na$_2$SO$_4$ and concentrated under reduced pressure. The residue was purified by column chromatography to give 1,2-dimethoxy-4-[2-nitrobut-1-enyl]benzene (120 g) as a yellow solid.

Step 2: Preparation of 1-(3,4-dimethoxyphenyl)butan-2-amine

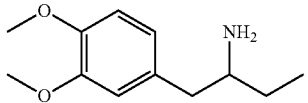

To a solution of 1,2-dimethoxy-4-[2-nitrobut-1-enyl]benzene (108 g, 454 mmol) in methanol (500 mL) was added Pd/C (10.0 g). The mixture was stirred at 50° C. under 50 psi of H$_2$ atmosphere for 60 hours, and then filtered through a celite pad. The filtrate was concentrated to give 1-(3,4-dimethoxyphenyl)butan-2-amine (54.0 g) as a white solid.

Step 3: Preparation of N-[1-[(3,4-dimethoxyphenyl)methyl]propyl]formamide

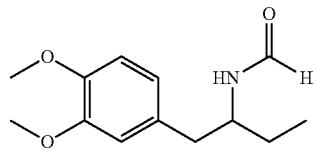 [SMILES: CCC(Cc1ccc(OC)c(OC)c1)NC=O]

1-(3,4-Dimethoxyphenyl)butan-2-amine (54 g, 258 mmol) was dissolved in ethanol (250 mL) under nitrogen atmosphere. Ethyl formate (300 mL) and triethylamine (20 mL) was added dropwise successively. The resultant mixture was refluxed for 2 days. The mixture was concentrated in vacuo to give N-[1-[(3,4-dimethoxyphenyl)methyl]propyl]formamide (50.0 g).

Step 4: Preparation of 3-ethyl-6,7-dimethoxy-3,4-dihydroisoquinoline

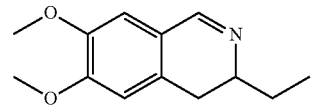 [SMILES: CCC1Cc2cc(OC)c(OC)cc2C=N1]

To a solution of N-[1-[(3,4-dimethoxyphenyl)methyl]propyl]formamide (50.0 g, 211 mmol) in acetonitrile (100 mL) was added POCl$_3$ (48.4 g, 316.4 mmol) dropwise. The resultant mixture was refluxed for 1 hour. The resultant mixture was basified to pH>10 with ammonia and then extracted with ethyl acetate. The organic layer was concentrated in vacuo and the residue was purified by column chromatography to give 3-ethyl-6,7-dimethoxy-3,4-dihydroisoquinoline.

Step 5: Preparation of 6-ethyl-9,10-dimethoxy-2-oxo-6,7-dihydrobenzo[a]quinolizine-3-carboxylic Acid

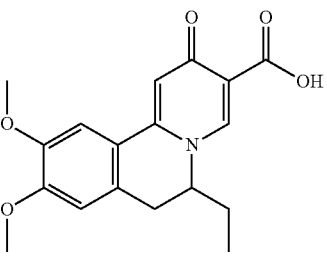 [SMILES: CCC1Cc2cc(OC)c(OC)cc2-c2cc(=O)c(C(=O)O)cn21]

A mixture of 3-ethyl-6,7-dimethoxy-3,4-dihydroisoquinoline (4 g, 18 mmol), hydrochloric acid in dioxane (5 M, 2 mL, 10 mmol) and ethyl 2-(dimethylaminomethylene)-3-oxo-butanoate (4, 21.6 mmol) in DMSO (20 mL) was heated under microwave irradiation at 125° C. for 1 hour. To this mixture was added MnO$_2$ (4.7 g, 54 mmol), and then the mixture was heated at 120° C. for 5 hours. Then additional MnO$_2$ (1.6 g, 18 mmol) was added and the mixture was heated for additional 2 hours. The mixture was partitioned between DCM and water, and the aqueous layer was acidified by hydrochloric acid to pH=1. The organic layer was washed with brine, and then dried over anhydrous Na$_2$SO$_4$ and concentrated. The residue was purified by column chromatography and then recrystallized in ethanol to give 6-ethyl-9,10-dimethoxy-2-oxo-6,7-dihydrobenzo[a]quinolizine-3-carboxylic acid as a white solid (1.8 g).

Step 6: Preparation of (6R)-6-ethyl-9,10-dimethoxy-2-oxo-6,7-dihydrobenzo[a]quinolizine-3-carboxylic acid and (6S)-6-ethyl-9,10-dimethoxy-2-oxo-6,7-dihydrobenzo[a]quinolizine-3-carboxylic Acid

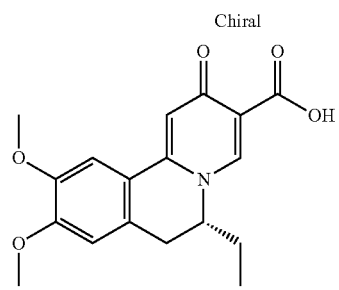

(6R)-enantiomer

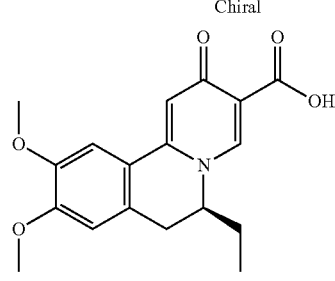

(6S)-enantiomer

Separation of the racemic 6-ethyl-9,10-dimethoxy-2-oxo-6,7-dihydrobenzo[a]quinolizine-3-carboxylic acid (50 mg) by chiral HPLC afforded (6R)-6-ethyl-9,10-dimethoxy-2-oxo-6,7-dihydrobenzo[a]quinolizine-3-carboxylic acid (10 mg) and (6S)-6-ethyl-9,10-dimethoxy-2-oxo-6,7-dihydrobenzo[a]quinolizine-3-carboxylic acid (10 mg).

(6R)-6-ethyl-9,10-dimethoxy-2-oxo-6,7-dihydrobenzo[a]quinolizine-3-carboxylic acid: $[\alpha]_D^{20}$=+121.21 (0.165%, CH$_3$CN), the absolute stereochemistry was determined by the X-ray diffraction study of its (6S)-enantiomer.

(6S)-6-ethyl-9,10-dimethoxy-2-oxo-6,7-dihydrobenzo[a]quinolizine-3-carboxylic acid: the absolute stereochemistry was determined by X-ray diffraction study (FIG. 1).

Step 7: Preparation of (6R)-6-ethyl-9,10-dimethoxy-2-oxo-N-(1H-tetrazol-5-yl)-6,7-dihydrobenzo[a]quinolizine-3-carboxamide

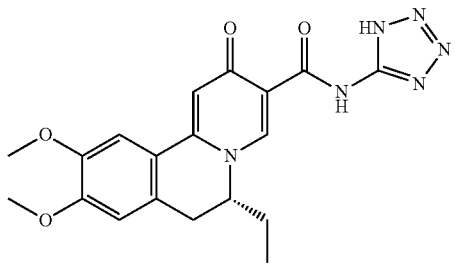 [SMILES: CC[C@@H]1Cc2cc(OC)c(OC)cc2-c2cc(=O)c(C(=O)Nc3nnn[nH]3)cn21]

To a solution of (6R)-6-ethyl-9,10-dimethoxy-2-oxo-6,7-dihydrobenzo[a]quinolizine-3-carboxylic acid (30 mg, 0.091 mmol) in DMF (2 mL) was added HATU (51.9 mg, 0.14 mmol) and Et$_3$N (25.6 µL, 0.18 mmol). The mixture was stirred for 5 minutes at room temperature, then 1H-tetrazol-5-amine (15.5 mg, 0.18 mmol) was added. The reaction mixture was stirred for 4 hours and purified by preparative HPLC to give (6R)-6-ethyl-9,10-dimethoxy-2-oxo-N-(1H-tetrazol-5-yl)-6,7-dihydrobenzo[a]quinolizine-3-carboxamide (10 mg). $^1$H NMR (400 MHz, DMSO) δ8.82 (s, 1H), 7.51 (s, 1H), 7.36 (s, 1H), 7.04 (s, 1H), 4.73-4.72 (m, 1H), 3.89 (s, 3H), 3.85 (s, 3H), 3.38-3.36 (m, 1H), 3.09-3.04 (m, 1H), 1.54-1.43 (m, 2H), 0.83 (t, J=7.2 Hz, 3H). MS obsd. (ESI$^+$) [(M+H)$^+$]: 397.

Example 32: 6-tert-butyl-10-methoxy-9-(3-methoxypropoxy)-2-oxo-N-(1H-tetrazol-5-yl)-6,7-dihydrobenzo[a]quinolizine-3-carboxamide Step 1: Preparation of 1-[4-methoxy-3-(3-methoxypropoxy)phenyl]-3,3-dimethyl-butan-2-one

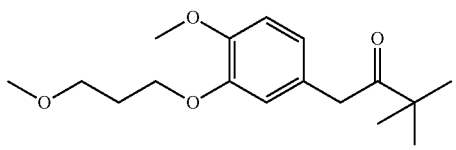 [SMILES: COCCCOc1cc(CC(=O)C(C)(C)C)ccc1OC]

To a solution of 4-bromo-1-methoxy-2-(3-methoxypropoxy)benzene (27.5 g, 0.1 mol) in THF (300 mL) was added 3,3-dimethyl-2-butanone (30 g, 0.3 mol, Accela), Pd$_2$(dba)$_3$ (1.37 g, 1.5 mmol), Xantphos (1.74 g, 3.0 mmol) and sodium tert-butoxide (31.7 g, 0.33 mol). The resultant mixture was stirred for 8 h at 60° C. under argon atmosphere. After being cooled to room temperature, the suspension was filtered with suction, the filter cake was poured into water and acidified to PH=3 with 2N hydrochloride acid. The mixture was extracted with ethyl acetate (400 mL×2) and the combined organic layers were washed with water (200 mL) and brine, dried over anhydrous Na$_2$SO$_4$ and concentrated to give 1-[4-methoxy-3-(3-methoxypropoxy)phenyl]-3,3-dimethyl-butan-2-one (23 g) as a yellow oil.

Step 2: Preparation of 1-[4-methoxy-3-(3-methoxypropoxy)phenyl]-3,3-dimethyl-butan-2-amine

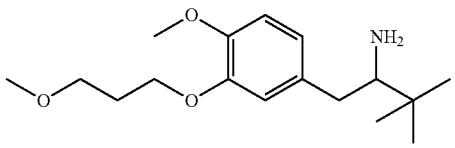 [SMILES: COCCCOc1cc(CC(N)C(C)(C)C)ccc1OC]

To a solution of 1-[4-methoxy-3-(3-methoxypropoxy)phenyl]-3,3-dimethyl-butan-2-one (23 g, 78 mmol) in methanol (230 mL) was added ammonium acetate (90 g, 1.17 mol) and NaBH$_3$CN (9.8 g, 156 mmol). The resultant mixture was stirred for 12 h at room temperature.

The reaction was quenched with water, and then 2.0 M NaOH aqueous solution (150 mL) was added. The resultant mixture was stirred for 1 h and then extracted with ethyl acetate (450 mL). The organic layer was washed with water (200 mL×2) and brine, dried over anhydrous Na$_2$SO$_4$ and concentrated to give 1-[4-methoxy-3-(3-methoxypropoxy)phenyl]-3,3-dimethyl-butan-2-amine (20 g) which was used directly in next step without further purification.

Step 3: Preparation of N-[1-[[4-methoxy-3-(3-methoxypropoxy)phenyl]methyl]-2,2-dimethyl-propyl]formamide

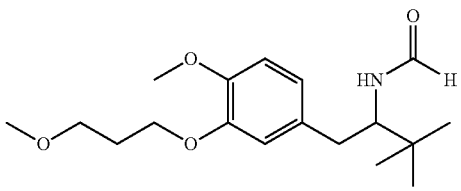 [SMILES: COCCCOc1cc(CC(NC=O)C(C)(C)C)ccc1OC]

A mixture of 1-[4-methoxy-3-(3-methoxypropoxy)phenyl]-3,3-dimethyl-butan-2-amine (20 g, 67.8 mmol) and formic acid (9.3 g, 203 mmol) in 1,4-dioxane (200 mL) was refluxed for 12 h and then concentrated under reduced pressure. The residue was dissolved in ethyl acetate (300 mL) and then washed with water (100 mL×2) and brine, dried over anhydrous Na$_2$SO$_4$ and concentrated to give N-[1-[[4-methoxy-3-(3-methoxypropoxy)phenyl]methyl]-2,2-dimethyl-propyl]formamide (20.6 g).

Step 4: Preparation of 3-tert-butyl-7-methoxy-6-(3-methoxypropoxy)-3,4-dihydroisoquinoline

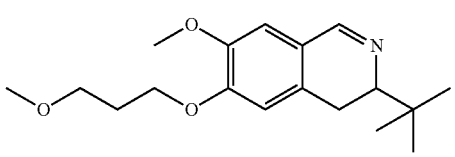 [SMILES: COCCCOc1cc2c(cc1OC)C=NC(C(C)(C)C)C2]

To a solution of N-[1-[[4-methoxy-3-(3-methoxypropoxy)phenyl]methyl]-2,2-dimethyl-propyl]formamide (20.6 g, 62 mmol) in acetonitrile (100 mL) was added POCl$_3$ (14.2 g, 93 mol) dropwise at 0-5° C., the resultant mixture was refluxed for 3 h. After cooling to room temperature, the solvent was removed and then ethyl acetate (100 mL) was added, followed by addition of ammonia water to adjust the pH of the aqueous solution to around 11. The mixture was extracted with ethyl acetate (200 mL×2), and the organic layers were combined and concentrated. The residue was purified by column chromatography to give 3-tert-butyl-7-methoxy-6-(3-methoxypropoxy)-3,4-dihydroisoquinoline (18 g).

Step 5: Preparation of ethyl 6-tert-butyl-10-methoxy-9-(3-methoxypropoxy)-2-oxo-1,6,7,11b-tetrahydrobenzo[a]quinolizine-3-carboxylate

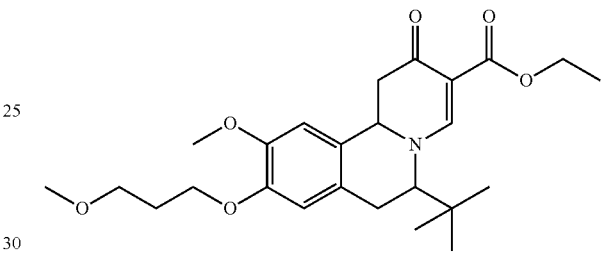

A mixture of 3-tert-butyl-7-methoxy-6-(3-methoxypropoxy)-3,4-dihydroisoquinoline (18 g, 60 mmol) and ethyl 2-(ethoxymethylene)-3-oxo-butanoate (33.5 g, 180 mmol) in ethanol (200 mL) was refluxed overnight. The mixture was concentrated to give crude ethyl 6-tert-butyl-10-methoxy-9-(3-methoxypropoxy)-2-oxo-1,6,7,11b-tetrahydrobenzo[a]quinolizine-3-carboxylate (26.7 g) as a dark brown oil which was used in next step without purification.

Step 6: Preparation of ethyl 6-tert-butyl-10-methoxy-9-(3-methoxypropoxy)-2-oxo-6,7-dihydrobenzo[a]quinolizine-3-carboxylate

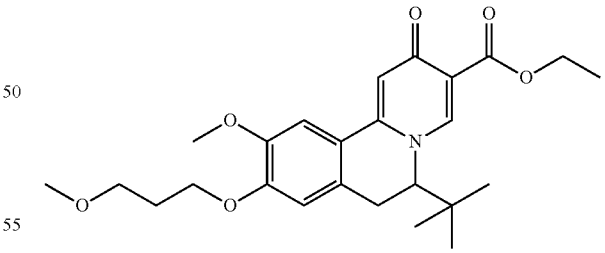

A mixture of crude ethyl 6-tert-butyl-10-methoxy-9-(3-methoxypropoxy)-2-oxo-1,6,7,11b-tetrahydrobenzo[a]quinolizine-3-carboxylate (26.7 g, 60 mmol) from step 5 and p-chloranil (11 g, 45 mmol) in DME (85 mL) was refluxed for 2 h. After being cooled to room temperature, the suspension was filtered with suction. The filter cake was washed with cold DME and dried under vacuum to give ethyl 6-tert-butyl-10-methoxy-9-(3-methoxypropoxy)-2-oxo-6,7-dihydrobenzo[a]quinolizine-3-carboxylate as a yellow solid (15.5 g)

Step 7: Preparation of 6-tert-butyl-10-methoxy-9-(3-methoxypropoxy)-2-oxo-6,7-dihydrobenzo[a]quinolizine-3-carboxylic Acid

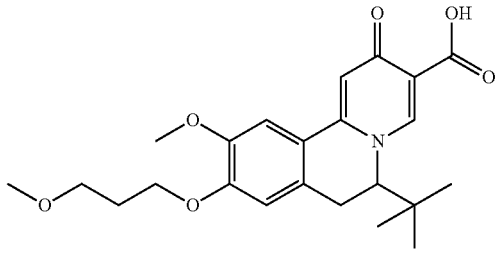 [SMILES: COCCCOc1cc2c(cc1OC)-c1cc(=O)c(C(=O)O)cn1C(C(C)(C)C)C2]

To a solution of ethyl 6-tert-butyl-10-methoxy-9-(3-methoxypropoxy)-2-oxo-6,7-dihydrobenzo[a]quinolizine-3-carboxylate (15.5 g, 35 mmol) in THF (30 mL) and methanol (150 mL) was added 2.0 M LiOH (70 mL) aqueous solution at rt. The resultant mixture was stirred for 4 h, and then acidified to pH=1-2 with 2M hydrochloric acid. The mixture was extracted with DCM (200 mL×2). The combined organic layers were washed with water and brine, dried over anhydrous $Na_2SO_4$ and concentrated to give a yellow solid, which was purified by column chromatography to give 6-tert-butyl-10-methoxy-9-(3-methoxypropoxy)-2-oxo-6,7-dihydrobenzo[a]quinolizine-3-carboxylic acid (8.5 g).

Step 8: Preparation of 6-tert-butyl-10-methoxy-9-(3-methoxypropoxy)-2-oxo-N-(1H-tetrazol-5-yl)-6,7-dihydrobenzo[a]quinolizine-3-carboxamide

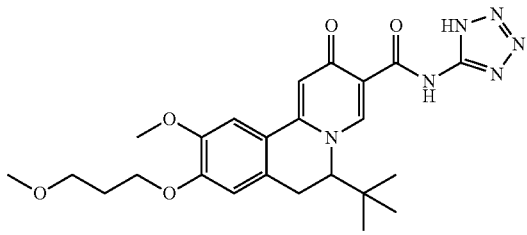 [SMILES: COCCCOc1cc2c(cc1OC)-c1cc(=O)c(C(=O)Nc3nnn[nH]3)cn1C(C(C)(C)C)C2]

To a solution of 6-tert-butyl-10-methoxy-9-(3-methoxypropoxy)-2-oxo-6,7-dihydrobenzo[a]quinolizine-3-carboxylic acid (30 mg, 0.072 mmol) in DMF (2 mL) was added HATU (41.2 mg, 0.11 mmol) and $Et_3N$ (20.3 μL, 0.14 mmol). The reaction was stirred for 5 minutes at room temperature, then 1H-tetrazol-5-amine (12.3 mg, 0.14 mmol) was added. The reaction mixture was stirred for 4 hours and purified by preparative HPLC to give 6-tert-butyl-10-methoxy-9-(3-methoxypropoxy)-2-oxo-N-(1H-tetrazol-5-yl)-6,7-dihydrobenzo[a]quinolizine-3-carboxamide (6 mg). $^1H$ NMR (400 MHz, DMSO) δ8.74 (s, 1H), 7.46 (s, 1H), 7.33 (s, 1H), 7.07 (s, 1H), 4.59-4.51 (m, 1H), 4.19-4.05 (m, 2H), 3.87 (s, 3H), 3.50-3.47 (m, 3H), 3.29-3.26 (m, 4H), 2.01-1.98 (m, 2H), 0.75 (s, 9H). MS obsd. (ESI$^+$) [(M+H)$^+$]: 483.

Example 33: 6-cyclobutyl-10-methoxy-9-(3-methoxypropoxy)-2-oxo-N-(1H-tetrazol-5-yl)-6,7-dihydrobenzo[a]quinolizine-3-carboxamide

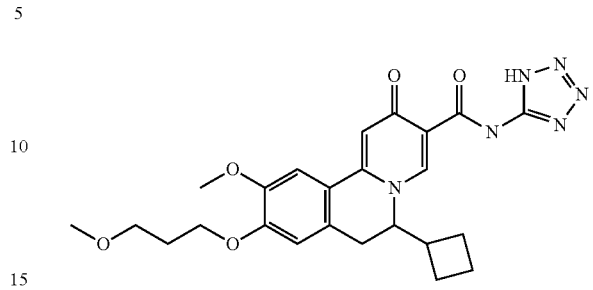

Step 1: Preparation of 1-cyclobutyl-2-[4-methoxy-3-(3-methoxypropoxy)phenyl]ethanone

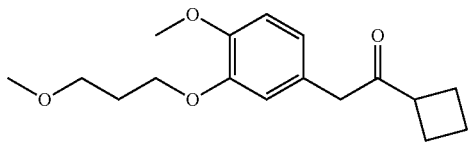 [SMILES: COCCCOc1cc(CC(=O)C2CCC2)ccc1OC]

To a mixture of 4-bromo-1-methoxy-2-(3-methoxypropoxy)benzene (2.74 g, 10 mmol), tris(dibenzylideneacetone)dipalladium(0) (92 mg, 0.1 mmol), 9,9-Dimethyl-4,5-bis(diphenylphosphino)xanthene (116 mg, 0.2 mmol) and t-BuONa (2.02 g, 22 mmol) in THF (20 mL) was added acetylcyclobutane (1.96 g, 20 mmol, Alfa Aesar). The resulting mixture was heated to 50° C. for 7 h under argon. After cooling to room temperature, the mixture was diluted with water and EtOAc. The aqueous solution was extracted with EtOAc (50 mL×2). The combined organic layers were filtered. The filtrate was washed with brine, dried over anhydrous $Na_2SO_4$ and concentrated under reduced pressure to give crude 1-cyclobutyl-2-[4-methoxy-3-(3-methoxypropoxy)phenyl]ethanone (3.47 g) as a yellow oil which was directly used for next step without purification.

Step 2: Preparation of 1-cyclobutyl-2-[4-methoxy-3-(3-methoxypropoxy)phenyl]ethanamine

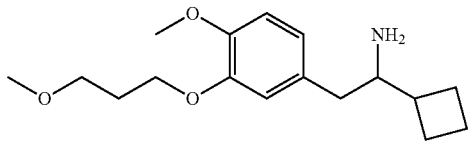 [SMILES: COCCCOc1cc(CC(N)C2CCC2)ccc1OC]

To a mixture of crude 1-cyclobutyl-2-[4-methoxy-3-(3-methoxypropoxy)phenyl]ethanone (3.47 g, 10 mmol) and ammonium acetate (11.55 g, 150 mmol) in $CH_3OH$ (20 mL) was added $NaBH_3CN$ (605 mg, 9.6 mmol). The resulting mixture was stirred at room temperature for 40 h, basified by 2N NaOH to PH=12~14, and then extracted with $CH_2Cl_2$ (30 mL×3). The combined organic layers were concentrated under reduced pressure. The residue was dissolved in $CH_2Cl_2$ (20 mL) and then washed with 1N HCl (30 mL×3). The separated aqueous layer was basified by 2N NaOH to PH=12~14, and then extracted with CH₂Cl₂ (40 mL×3). The combined organic layers were washed with brine, dried over anhydrous Na₂SO₄ and concentrated to give crude 1-cyclobutyl-2-[4-methoxy-3-(3-methoxypropoxy)phenyl]ethanamine (1.13 g) as a yellow oil.

Step 3: Preparation of N-[1-cyclobutyl-2-[4-methoxy-3-(3-methoxypropoxy)phenyl]ethyl]formamide

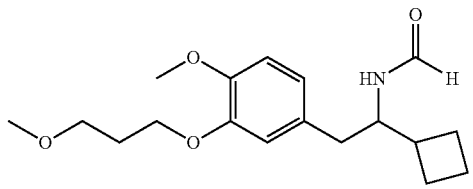 [SMILES: COCCCOc1cc(CC(NC=O)C2CCC2)ccc1OC]

A solution of 1-cyclobutyl-2-[4-methoxy-3-(3-methoxypropoxy)phenyl]ethanamine (1.13 g, 3.86 mmol) and formic acid (0.2 mL) in ethyl formate (20 mL) was heated to 90° C. overnight. The solvent was removed under reduced pressure to give crude N-[1-cyclobutyl-2-[4-methoxy-3-(3-methoxypropoxy)phenyl]ethyl]formamide (1.24 g) as a yellow oil which was directly used for next step without purification.

Step 4: Preparation of 3-cyclobutyl-7-methoxy-6-(3-methoxypropoxy)-3,4-dihydroisoquinoline

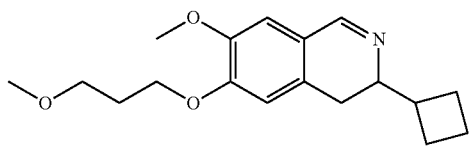 [SMILES: COCCCOc1cc2c(cc1OC)C=NC(C1CCC1)C2]

To a solution of N-[1-cyclobutyl-2-[4-methoxy-3-(3-methoxypropoxy)phenyl]ethyl]formamide (1.24 g, 3.86 mmol) in CH₃CN (10 mL) was added POCl₃ (708 mg, 4.63 mmol). The reaction mixture was heated to 60° C. for 2 h and concentrated. The residue was dissolved in CH₃CN (10 mL) and then basified by ammonium hydroxide to PH=10 at 0° C. The resulting mixture was extracted with CH₂Cl₂, and the organic layer was washed with brine, dried and concentrated under reduced pressure to give crude 3-cyclobutyl-7-methoxy-6-(3-methoxypropoxy)-3,4-dihydroisoquinoline (920 mg) as a yellow oil.

Step 5: Preparation of ethyl 6-cyclobutyl-10-methoxy-9-(3-methoxypropoxy)-2-oxo-1,6,7,11b-tetrahydrobenzo[a]quinolizine-3-carboxylate

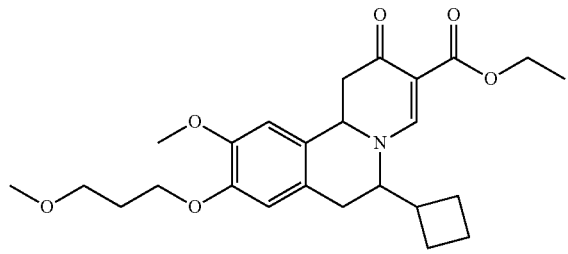 [SMILES: CCOC(=O)C1=CN2C(CC1=O)c1cc(OC)c(OCCCOC)cc1CC2C1CCC1]

A mixture of crude 3-cyclobutyl-7-methoxy-6-(3-methoxypropoxy)-3,4-dihydroisoquinoline (920 mg, 3 mmol) and ethyl 2-(ethoxymethylene)-3-oxo-butanoate (1.67 g, 9 mmol) in EtOH (10 mL) was heated to 100° C. for 16 h. The mixture was concentrated under reduced pressure to give crude ethyl 6-cyclobutyl-10-methoxy-9-(3-methoxypropoxy)-2-oxo-1,6,7,11b-tetrahydrobenzo[a]quinolizine-3-carboxylate (2.43 g) as a brown oil which was directly used in next step without purification.

Step 6: Preparation of ethyl 6-cyclobutyl-10-methoxy-9-(3-methoxypropoxy)-2-oxo-6,7-dihydrobenzo[a]quinolizine-3-carboxylate

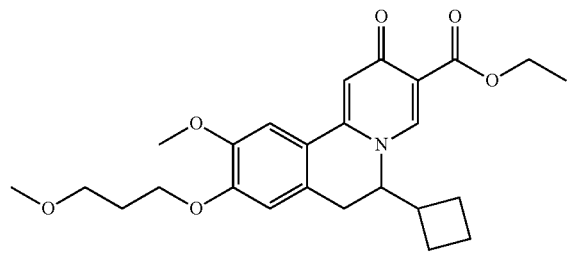 [SMILES: CCOC(=O)c1cn2c(cc1=O)-c1cc(OC)c(OCCCOC)cc1CC2C1CCC1]

A mixture of crude ethyl 6-cyclobutyl-10-methoxy-9-(3-methoxypropoxy)-2-oxo-1,6,7,11b-tetrahydrobenzo[a]quinolizine-3-carboxylate (2.43 g, 3 mmol) and p-chloranil (738 mg, 3 mmol) in DME (10 mL) was heated to 70° C. for 3 h under argon. After being cooled to room temperature, the mixture was diluted with CH₂Cl₂ and H₂O. The organic layer was washed with saturated NaHCO₃ aqueous solution, brine, dried over anhydrous Na₂SO₄ and concentrated to give crude ethyl 6-cyclobutyl-10-methoxy-9-(3-methoxypropoxy)-2-oxo-6,7-dihydrobenzo[a]quinolizine-3-carboxylate (2.62 g) as a brown oil.

Step 7: Preparation of 6-cyclobutyl-10-methoxy-9-(3-methoxypropoxy)-2-oxo-6,7-dihydrobenzo[a]quinolizine-3-carboxylic Acid

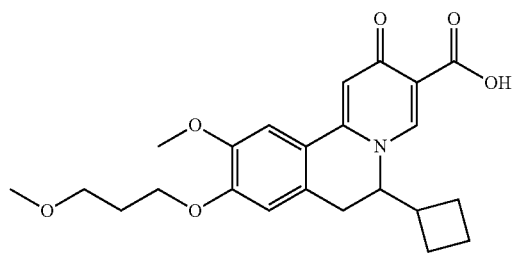 [SMILES: COCCCOc1cc2c(cc1OC)-c1cc(=O)c(C(=O)O)cn1C(C1CCC1)C2]

To a mixture of crude ethyl 6-cyclobutyl-10-methoxy-9-(3-methoxypropoxy)-2-oxo-6,7-dihydrobenzo[a]quinolizine-3-carboxylate (2.62 g, 3 mmol) in CH₃OH (12 mL) and H₂O (3 mL) was added LiOH.H₂O (492 mg, 12 mmol). The resulting mixture was stirred at room temperature for 16 h. The reaction mixture was acidified by 1N HCl to PH=2~3, then extracted with CH₂Cl₂ (50 mL×3). The combined organic layers were washed with brine, dried over anhydrous Na₂SO₄, and concentrated. The residue was precipitated from Et₂O/EtOH to afford 6-cyclobutyl-10-methoxy-9-(3- methoxypropoxy)-2-oxo-6,7-dihydrobenzo[a]quinolizine-3-carboxylic acid (500 mg) as a pale solid.

Step 8: Preparation of 6-cyclobutyl-10-methoxy-9-(3-methoxypropoxy)-2-oxo-N-(1H-tetrazol-5-yl)-6,7-dihydrobenzo[a]quinolizine-3-carboxamide

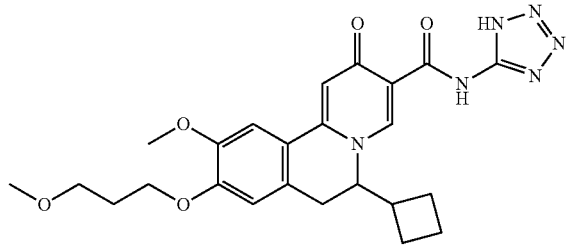 [SMILES: COCCCOc1cc2c(cc1OC)-c1cc(=O)c(C(=O)Nc3nnn[nH]3)cn1C(C1CCC1)C2]

To a solution of 6-cyclobutyl-10-methoxy-9-(3-methoxypropoxy)-2-oxo-6,7-dihydrobenzo[a]quinolizine-3-carboxylic acid (30 mg, 0.073 mmol) in DMF (2 mL) was added HATU (41.4 mg, 0.11 mmol) and Et$_3$N (20.4 µL, 0.15 mmol). The reaction was stirred for 5 minutes at room temperature, then 1H-tetrazol-5-amine (12.4 mg, 0.15 mmol) was added. The reaction mixture was stirred for 4 hours and purified by preparative HPLC to give 6-cyclobutyl-10-methoxy-9-(3-methoxypropoxy)-2-oxo-N-(1H-tetrazol-5-yl)-6,7-dihydrobenzo[a]quinolizine-3-carboxamide (6 mg). $^1$H NMR (400 MHz, DMSO) δ8.83 (s, 1H), 7.50 (s, 1H), 7.36 (s, 1H), 7.01 (s, 1H), 4.77-4.73 (m, 1H), 4.15-4.08 (m, 2H), 3.89 (s, 3H), 3.50-3.47 (m, 2H), 3.32-3.26 (m, 4H), 2.91-2.85 (m, 1H), 2.28-2.31 (m, 1H), 2.01-1.97 (m, 2H), 1.96-1.51 (m, 5H), 1.27-1.26 (m, 1H). MS obsd. (ESI$^+$) [(M+H)$^+$]: 481.

Example 34: 11-chloro-6-isopropyl-9-(2-methoxyethoxy)-2-oxo-N-(1H-tetrazol-5-yl)-6,7-dihydrobenzo[a]quinolizine-3-carboxamide

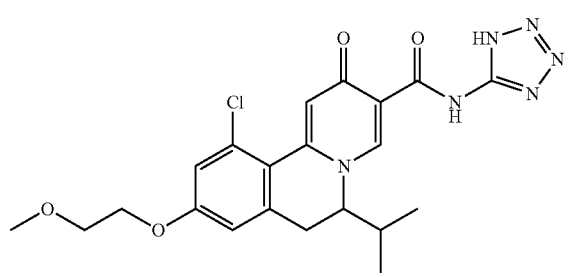 [SMILES: COCCOc1cc(Cl)c2c(c1)CC(C(C)C)n1cc(C(=O)Nc3nnn[nH]3)c(=O)cc1-2]

Step 1: Preparation of 1-bromo-3-chloro-5-(2-methoxyethoxy)benzene

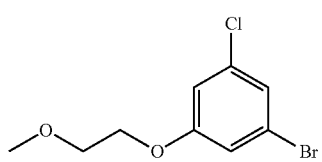

To a mixture of 3-bromo-5-chloro-phenol (14.0 g, 67.5 mmol, Accela) in MeCN (150 mL) was added 1-bromo-2-methoxy-ethane (12.6 g, 90.7 mmol) and Cs$_2$CO$_3$ (34.1 g, 105 mmol). The resultant mixture was heated at 80° C. for 12 hours, and then cooled to room temperature and then filtered. The filtrate was evaporated under reduced pressure, and the residue was purified by column chromatography to give 1-bromo-3-chloro-5-(2-methoxyethoxy)benzene (17.0 g) as a colorless oil.

Step 2: Preparation of 1-[3-chloro-5-(2-methoxyethoxy)phenyl]-3-methyl-butan-2-one

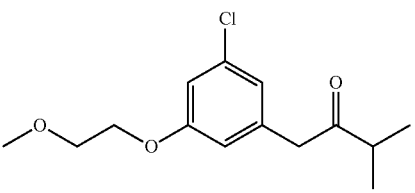 [SMILES: COCCOc1cc(Cl)cc(CC(=O)C(C)C)c1]

To a mixture of 1-bromo-3-chloro-5-(2-methoxyethoxy)benzene (14.8 g, 55.7 mmol), tris(dibenzylideneacetone)dipalladium(0) (1.02 g, 1.11 mmol), 9,9-dimethyl-4,5-bis(diphenylphosphino)xanthene (1.29 g, 2.22 mmol) and t-BuONa (9.62 g, 100 mmol) in THF (150 mL) was added 3-methylbutan-2-one (7.18 g, 83.4 mmol). The resultant mixture was heated at 50° C. for 12 hours under nitrogen atmosphere, and then cooled to room temperature and then filtered. The filtrate was concentrated under reduced pressure, and the residue was purified by column chromatography to afford 1-[3-chloro-5-(2-methoxyethoxy)phenyl]-3-methyl-butan-2-one (13.0 g) as a colorless oil which was directly used for the next step without further purification.

Step 3: Preparation of 1-[3-chloro-5-(2-methoxyethoxy)phenyl]-3-methyl-butan-2-amine

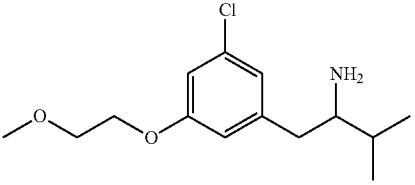 [SMILES: COCCOc1cc(Cl)cc(CC(N)C(C)C)c1]

A mixture of 1-[3-chloro-5-(2-methoxyethoxy)phenyl]-3-methyl-butan-2-one (15.2 g, 56.1 mmol) and ammonium acetate (30.3 g, 393 mmol) in CH$_3$OH (150 mL) was stirred at room temperature for 1 hour. NaBH$_3$CN (4.59 g, 73 mmol) was added at 0° C. The resultant mixture was stirred at room temperature for 12 hours and then concentrated. The residue was diluted with H$_2$O (20 mL) and then extracted with CH$_2$Cl$_2$ (500 mL). The organic layer was washed with brine (100 mL), and then dried over anhydrous Na$_2$SO$_4$ and then evaporated under reduced pressure to afford 1-[3-chloro-5-(2-methoxyethoxy)phenyl]-3-methyl-butan-2-amine (19.0 g, crude) as a light yellow oil which was directly used for the next step without purification.

Step 4: Preparation of N-[1-[[3-chloro-5-(2-methoxyethoxy)phenyl]methyl]-2-methyl-propyl]formamide

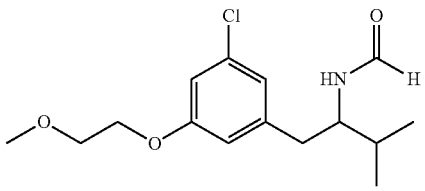 [SMILES: COCCOc1cc(Cl)cc(CC(NC=O)C(C)C)c1]

A solution of 1-[3-chloro-5-(2-methoxyethoxy)phenyl]-3-methyl-butan-2-amine (17.0 g, 62.6 mmol) and formic acid (11.5 g, 250 mmol) in 1,4-dioxane (200 mL) was heated to reflux for 12 hours. The reaction solution was diluted with $H_2O$ (200 mL) and then extracted with EtOAc (200 mL×2). The organic layer was dried over anhydrous $Na_2SO_4$ and then concentrated. The residue was purified by column chromatography to give N-[1-[[3-chloro-5-(2-methoxyethoxy)phenyl]methyl]-2-methyl-propyl]formamide (10.0 g) as a light yellow oil.

Step 5: Preparation of 8-chloro-3-isopropyl-6-(2-methoxyethoxy)-3,4-dihydroisoquinoline

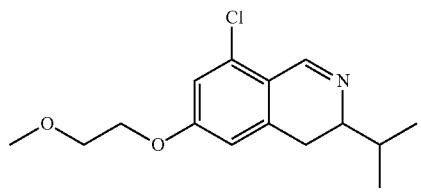 [SMILES: COCCOc1cc(Cl)c2c(c1)CC(C(C)C)N=C2]

A stirred solution of N-[1-[[3-chloro-5-(2-methoxyethoxy)phenyl]methyl]-2-methyl-propyl]formamide (9.0 g, 30.0 mmol) in $CH_2Cl_2$ (100 mL) was cooled to 0° C., and then $POCl_3$ (5.31 g, 34.5 mmol) was added slowly. Then the mixture was refluxed for 2 hours. After being cooled down, the mixture was poured into a solution of $NH_4OH$ (50 mL) in $H_2O$ (200 mL), and then stirred for 0.5 hour. The mixture was extracted with $CH_2Cl_2$ (500 mL). The organic layer was washed with brine (200 mL), and then dried over anhydrous $Na_2SO_4$ and then evaporated under reduced pressure. The residue was purified by column chromatography to give 8-chloro-3-isopropyl-6-(2-methoxyethoxy)-3,4-dihydroisoquinoline (2.02 g) as a yellow oil.

Step 6: Preparation of ethyl 11-chloro-6-isopropyl-9-(2-methoxyethoxy)-2-oxo-1,6,7,11b-tetrahydrobenzo[a]quinolizine-3-carboxylate

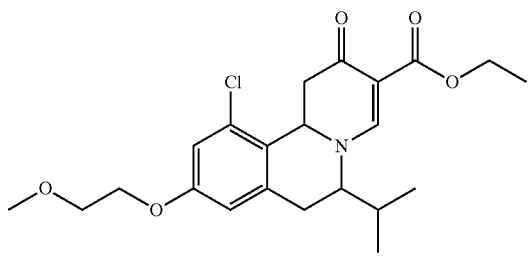 [SMILES: CCOC(=O)C1=CN2C(CC1=O)c1c(Cl)cc(OCCOC)cc1CC2C(C)C]

To a mixture of 8-chloro-3-isopropyl-6-(2-methoxyethoxy)-3,4-dihydroisoquinoline (843 mg, 3 mmol) and ethyl 2-(dimethylaminomethylene)-3-oxo-butanoate (851 mg, 6 mmol) in DMSO (5 mL) was added 4 M HCl in dioxane (0.15 mL, 0.6 mmol). The resultant mixture was heated at 130° C. for 8 hours under microwave, and then cooled to chromatography and diluted with EtOAc and $H_2O$. The separated aqueous layer was extracted with EtOAc. The combined organic layers were washed with brine, and then dried over anhydrous $Na_2SO_4$, and then concentrated to give crude ethyl 11-chloro-6-isopropyl-9-(2-methoxyethoxy)-2-oxo-1,6,7,11b-tetrahydrobenzo[a]quinolizine-3-carboxylate (1.35 g) as a yellow solid which was directly used in the next step without purification.

Step 7: Preparation of 11-chloro-6-isopropyl-9-(2-methoxyethoxy)-2-oxo-6,7-dihydrobenzo[a]quinolizine-3-carboxylic Acid

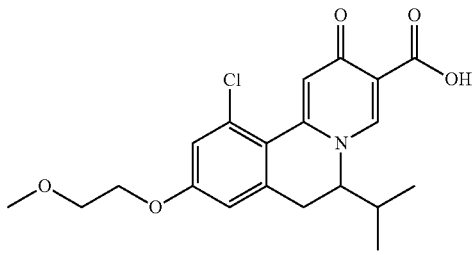 [SMILES: COCCOc1cc(Cl)c2c(c1)CC(C(C)C)n1cc(C(=O)O)c(=O)cc1-2]

A mixture of crude ethyl 11-chloro-6-isopropyl-9-(2-methoxyethoxy)-2-oxo-1,6,7,11b-tetrahydrobenzo[a]quinolizine-3-carboxylate (1.35 g, 3 mmol) and p-chloranil (590 mg, 2.4 mmol) in DME (10 mL) was heated at 70° C. for 3 hours, then heated at 100° C. for 16 hours, and then heated to 130° C. for 1 hour under microwave under argon atmosphere. After being cooled to room temperature, the resultant mixture was concentrated. The residue was purified by flash column chromatography and washed with $EtOH/Et_2O$ to afford 11-chloro-6-isopropyl-9-(2-methoxyethoxy)-2-oxo-6,7-dihydrobenzo[a]quinolizine-3-carboxylic acid (247 mg) as a yellow solid.

Step 8: Preparation of 11-chloro-6-isopropyl-9-(2-methoxyethoxy)-2-oxo-N-(1H-tetrazol-5-yl)-6,7-dihydrobenzo[a]quinolizine-3-carboxamide

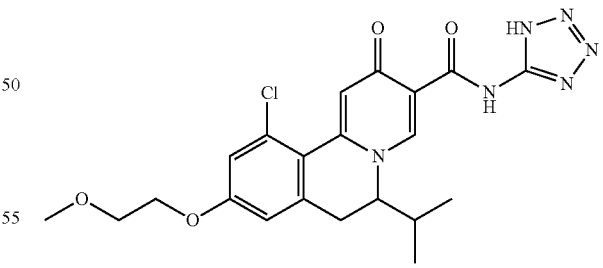

To a solution of 11-chloro-6-isopropyl-9-(2-methoxyethoxy)-2-oxo-6,7-dihydrobenzo[a]quinolizine-3-carboxylic acid (30 mg, 0.077 mmol) in DMF (2 mL) was added HATU (43.7 mg, 0.11 mmol) and $Et_3N$ (21.5 µL, 0.15 mmol). The reaction was stirred for 5 minutes at room temperature, then 1H-tetrazol-5-amine (13.0 mg, 0.15 mmol) was added. The reaction mixture was stirred for 4 hours and purified by preparative HPLC to give 11-chloro-6-isopropyl-9-(2-methoxyethoxy)-2-oxo-N-(1H-tetrazol-5-yl)-6,7-dihydrobenzo[a]quinolizine-3-carboxamide (6 mg).

¹H NMR (400 MHz, DMSO) δ 8.83 (s, 1H), 7.43 (s, 1H), 7.22-7.19 (m, 1H), 7.18-7.14 (m, 1H), 4.52-4.44 (m, 1H), 4.30-4.18 (m, 2H), 3.69 (t, 2H), 3.30-3.19 (m, 2H), 1.51-1.41 (m, 1H), 0.87 (d, 3H), 0.81 (d, 3H). MS obsd. (ESI⁺) [(M+H)⁺]: 459.

Example 35: 9,10-dimethoxy-2-oxo-N-(1H-tetrazol-5-yl)-6-(2,2,2-trifluoroethyl)-6,7-dihydrobenzo[a]quinolizine-3-carboxamide

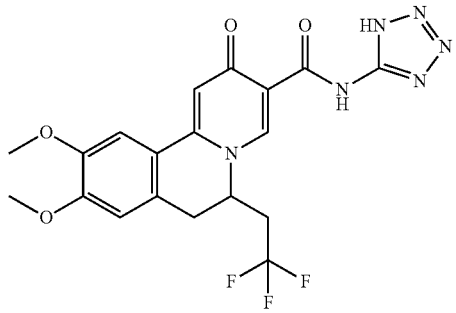 [SMILES: COc1cc2c(cc1OC)-c1cc(=O)c(C(=O)Nc3nnn[nH]3)cn1C(CC(F)(F)F)C2]

Step 1: Preparation of 1-(3,4-dimethoxyphenyl)-4,4,4-trifluoro-butane-1,3-dione

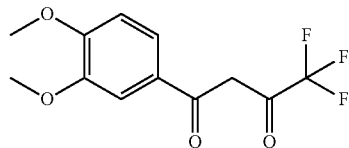 [SMILES: COc1ccc(C(=O)CC(=O)C(F)(F)F)cc1OC]

To a solution of 1-(3,4-dimethoxyphenyl)ethanone (5.4 g, 30 mmol) in DMF (30 mL) was added 60% NaH in mineral oil (1.56 g, 39 mmol) in portions at −5° C. to 0° C. After stirring at this temperature for 30 minutes, methyl 2,2,2-trifluoroacetate (5.0 g, 39 mmol, Aldrich) was added. The resulting mixture was allowed to warm to room temperature and stirred overnight, and then poured into ice-water, acidified with 2N HCl to PH=3. The aqueous solution was extracted with EtOAc, and the combined organic layers were washed with water, brine, dried and concentrated to give crude 1-(3,4-dimethoxyphenyl)-4,4,4-trifluoro-butane-1,3-dione (9.48 g) as an orange solid which was directly used for next step without purification.

Step 2: Preparation of 3-(3,4-dimethoxyphenyl)-5-(trifluoromethyl)-4H-isoxazol-5-ol

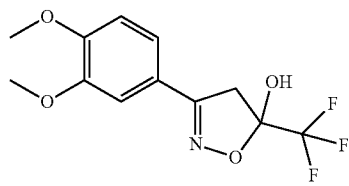 [SMILES: COc1ccc(C2=NOC(O)(C(F)(F)F)C2)cc1OC]

A mixture of hydroxylamine hydrochloride (1.38 g, 20 mmol) and sodium acetate (1.64 g, 20 mmol) in EtOH (100 mL) was heated to 90° C. for 15 minutes. Then 1-(3,4-dimethoxyphenyl)-4,4,4-trifluoro-butane-1,3-dione (6.32 g, 20 mmol) was added and stirred at 90° C. for 4 h. After removing the solvent under reduced pressure, the residue was extracted with CHCl₃. The combined organic layers were washed with brine, dried over anhydrous Na₂SO₄ and concentrated to give 3-(3,4-dimethoxyphenyl)-5-(trifluoromethyl)-4H-isoxazol-5-ol (5.95 g) as a yellow solid which was directly used for next step without purification.

Step 3: Preparation of 3-(3,4-dimethoxyphenyl)-5-(trifluoromethyl)isoxazole

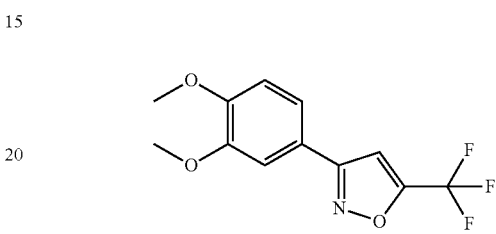

A mixture of 3-(3,4-dimethoxyphenyl)-5-(trifluoromethyl)-4H-isoxazol-5-ol (5.95 g, 20 mmol) in HOAc (60 mL) and conc. H₂SO₄ (0.4 mL) was heated to 115° C. overnight. After removing the solvent under reduced pressure, the residue was poured into water. The resulting mixture was stirred at room temperature for 15 minutes and then filtered. The filter cake was dissolved in CH₂Cl₂. The organic layer was washed with brine, dried over anhydrous Na₂SO₄ and concentrated. The residue was purified by flash column to afford 3-(3,4-dimethoxyphenyl)-5-(trifluoromethyl)isoxazole (4.43 g) as a yellow oil which was directly used for next step without purification.

Step 4: Preparation of 2-(3,4-dimethoxyphenyl)-3-(2,2,2-trifluoroethyl)aziridine

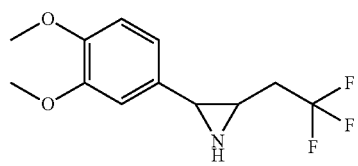 [SMILES: COc1ccc(C2NC2CC(F)(F)F)cc1OC]

To a solution of LiAlH₄ in THF (60 mL, 120 mmol) was added 3-(3,4-dimethoxyphenyl)-5-(trifluoromethyl)isoxazole (5.42 g, 20 mmol) in THF (40 mL). The resulting mixture was stirred at 65° C. for 2 h, and then additional LiAlH₄ in THF (20 mL, 40 mmol) was added. The mixture was stirred at 75° C. for 4 h, cooled to room temperature and quenched by H₂O at 0° C. After addition of potassium sodium tartrate tetrahydrate solution, the resultant mixture was stirred at room temperature for 2 h and then extracted with EtOAc (100 mL×5). The combined organic layers were washed with brine, dried over anhydrous Na₂SO₄ and concentrated. The residue was purified by flash chromatography to afford 2-(3,4-dimethoxyphenyl)-3-(2,2,2-trifluoroethyl)aziridine (1.90 g) as a yellow oil which was directly used for next step without further purification.

Step 5: Preparation of 1-(3,4-dimethoxyphenyl)-4,4,4-trifluoro-butan-2-amine

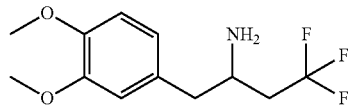 [SMILES: COc1ccc(CC(N)CC(F)(F)F)cc1OC]

A mixture of 2-(3,4-dimethoxyphenyl)-3-(2,2,2-trifluoroethyl)aziridine (783 mg, 3 mmol) and 10% palladium on carbon (78 mg) in CH₃OH (8 mL) was stirred at room temperature for 16 h. The reaction mixture was filtered, and the filtrate was concentrated under reduced pressure. The residue was dissolved in CH₂Cl₂ (30 mL), then acidified by 1N HCl to PH=2~3. The separated aqueous layer was basified by sat. NaHCO₃ to PH=8~9, then extracted with CH₂Cl₂ (30 mL×3). The combined organic layers were washed with brine, dried over anhydrous Na₂SO₄ and concentrated to afford 1-(3,4-dimethoxyphenyl)-4,4,4-trifluoro-butan-2-amine (573 mg) as a red oil which was directly used for next step without further purification.

Step 6: Preparation of N-[1-[(3,4-dimethoxyphenyl)methyl]-3,3,3-trifluoro-propyl]formamide

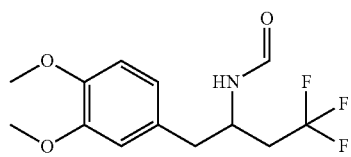 [SMILES: COc1ccc(CC(CC(F)(F)F)NC=O)cc1OC]

A solution of 1-(3,4-dimethoxyphenyl)-4,4,4-trifluoro-butan-2-amine (563 mg, 2.14 mmol) in ethyl formate (10 mL) and formic acid (0.1 mL) was heated to 90° C. overnight. After removing the excess solvent under reduced pressure, N-[1-[(3,4-dimethoxyphenyl)methyl]-3,3,3-trifluoro-propyl]formamide (663 mg) was obtained as a green oil which was directly used for next step without purification.

Step 7: Preparation of 6,7-dimethoxy-3-(2,2,2-trifluoroethyl)-3,4-dihydroisoquinoline

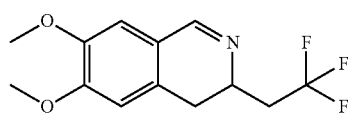 [SMILES: COc1cc2c(cc1OC)CC(CC(F)(F)F)N=C2]

To a solution of crude N-[1-[(3,4-dimethoxyphenyl)methyl]-3,3,3-trifluoro-propyl]formamide (663 mg, 2.14 mmol) in acetonitrile (6 mL) was added POCl₃ (393 mg, 2.57 mmol). The reaction mixture was heated to 60° C. for 2 h and then concentrated. The residue was dissolved in CH₂Cl₂ (20 mL) and then basified by ammonium hydroxide to PH=9~10 at 0° C. The resulting mixture was stirred at room temperature for 1 h and extracted with CH₂Cl₂ (30 mL×3). The combined organic layers were washed with brine, dried and concentrated under reduced pressure to afford crude 6,7-dimethoxy-3-(2,2,2-trifluoroethyl)-3,4-dihydroisoquinoline (577 mg) as a yellow oil which was directly used for next step without purification.

Step 8: Preparation of ethyl 9,10-dimethoxy-2-oxo-6-(2,2,2-trifluoroethyl)-1,6,7,11b-tetrahydrobenzo[a]quinolizine-3-carboxylate

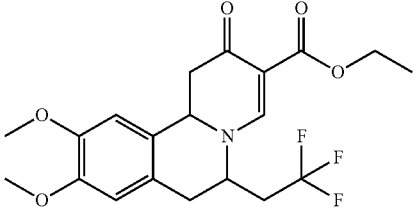 [SMILES: CCOC(=O)C1=CN2C(CC(F)(F)F)Cc3cc(OC)c(OC)cc3C2CC1=O]

A mixture of crude 6,7-dimethoxy-3-(2,2,2-trifluoroethyl)-3,4-dihydroisoquinoline (577 mg, 2.14 mmol) and ethyl 2-(dimethylaminomethylene)-3-oxo-butanoate (1.19 g, 6.42 mmol) in EtOH (6 mL) was heated to 100° C. for 16 h. The mixture was concentrated under reduced pressure. The residue was purified by recrystallization from diethyl ether/petroleum ether to afford ethyl 9,10-dimethoxy-2-oxo-6-(2,2,2-trifluoroethyl)-1,6,7,11b-tetrahydrobenzo[a]quinolizine-3-carboxylate (568 mg) as a yellow solid which was directly used in next step without further purification.

Step 9: Preparation of ethyl 9,10-dimethoxy-2-oxo-6-(2,2,2-trifluoroethyl)-6,7-dihydrobenzo[a]quinolizine-3-carboxylate

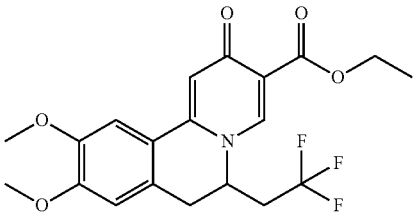 [SMILES: CCOC(=O)c1cn2c(cc1=O)-c1cc(OC)c(OC)cc1CC2CC(F)(F)F]

A mixture of ethyl 9,10-dimethoxy-2-oxo-6-(2,2,2-trifluoroethyl)-1,6,7,11b-tetrahydrobenzo[a]quinolizine-3-carboxylate (568 mg, 1.4 mmol) and p-chloranil (344 mg, 1.4 mmol) in DME (5 mL) was heated to 70° C. for 3 h under argon. After being cooled to room temperature, the resulting suspension was filtered. The filter cake was washed with DME, then dried to give ethyl 9,10-dimethoxy-2-oxo-6-(2,2,2-trifluoroethyl)-6,7-dihydrobenzo[a]quinolizine-3-carboxylate (375 mg) as a light-yellow solid.

Step 10: Preparation of 9,10-dimethoxy-2-oxo-6-(2,2,2-trifluoroethyl)-6,7-dihydrobenzo[a]quinolizine-3-carboxylic Acid

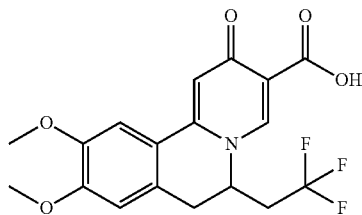 [SMILES: COc1cc2c(cc1OC)-c1cc(=O)c(C(=O)O)cn1C(CC(F)(F)F)C2]

To a solution of ethyl 9,10-dimethoxy-2-oxo-6-(2,2,2-trifluoroethyl)-6,7-dihydrobenzo[a]quinolizine-3-carboxylate (375 mg, 0.81 mmol) in CH$_3$OH (4 mL) and H$_2$O (1 mL) was added LiOH.H$_2$O (153 mg, 3.64 mmol). The resulting reaction mixture was stirred at room temperature for 2 h and then acidified by 1N HCl to PH=2~3. The resulting precipitate was filtered, and the filter cake was dried to afford 9,10-dimethoxy-2-oxo-6-(2,2,2-trifluoroethyl)-6,7-dihydrobenzo[a]quinolizine-3-carboxylic acid (285 mg) as a yellow solid.

Step 11: Preparation of 9,10-dimethoxy-2-oxo-N-(1H-tetrazol-5-yl)-6-(2,2,2-trifluoroethyl)-6,7-dihydrobenzo[a]quinolizine-3-carboxamide

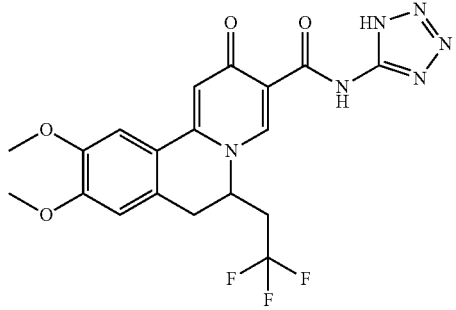 [SMILES: COc1cc2c(cc1OC)-c1cc(=O)c(C(=O)Nc3nnn[nH]3)cn1C(CC(F)(F)F)C2]

To a solution of 9,10-dimethoxy-2-oxo-6-(2,2,2-trifluoroethyl)-6,7-dihydrobenzo[a]quinolizine-3-carboxylic acid (30 mg, 0.078 mmol) in DMF (2 mL) was added HATU (44.7 mg, 0.12 mmol) and Et$_3$N (22.0 µL, 0.16 mmol), the reaction was stirred for 5 minutes at room temperature, then 1H-tetrazol-5-amine (13.3 mg, 0.16 mmol) was added to the solution. The reaction mixture was stirred for 4 hours and purified by preparative HPLC to give 9,10-dimethoxy-2-oxo-N-(1H-tetrazol-5-yl)-6-(2,2,2-trifluoroethyl)-6,7-dihydrobenzo[a]quinolizine-3-carboxamide (7 mg). $^1$H NMR (400 MHz, DMSO) δ=8.76 (s, 1H), 7.55 (s, 1H), 7.37 (s, 1H), 7.02 (s, 1H), 5.34-5.24 (m, 1H), 3.90 (s, 3H), 3.85 (s, 3H), 3.49-3.40 (m, 1H), 3.02 (m, 1H), 2.70-2.56 (m, 2H). MS obsd. (ESI$^+$) [(M+H)$^+$]: 451.

Example 36: 6-isopropyl-10-methoxy-9-(3-methoxypropoxy)-2-oxo-N-(1H-tetrazol-5-yl)-6,7-dihydrobenzo[a]quinolizine-3-carboxamide

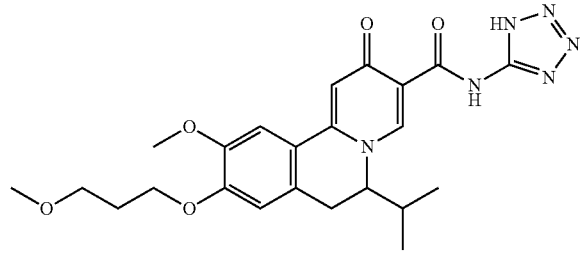 [SMILES: COCCCOc1cc2c(cc1OC)-c1cc(=O)c(C(=O)Nc3nnn[nH]3)cn1C(C(C)C)C2]

Step 1: Preparation of 4-bromo-1-methoxy-2-(3-methoxypropoxy)benzene

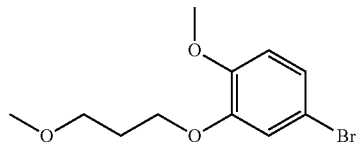

A 250 mL round-bottomed flask was charged with 5-bromo-2-methoxy-phenol (15.5 g, 76.4 mmol), 1-bromo-3-methoxy-propane (12.9 g, 84 mmol), K$_2$CO$_3$ (22 g, 2153 mmol) and DMF (50 mL). The resultant mixture was stirred at 50° C. for 3 hours, and then ethyl acetate and water was added. The organic phase was separated, and then dried over anhydrous Na$_2$SO$_4$ and then concentrated to give 4-bromo-1-methoxy-2-(3-methoxypropoxy)benzene (23 g).

Step 2: Preparation of 1-[4-methoxy-3-(3-methoxypropoxy)phenyl]-3-methyl-butan-2-one

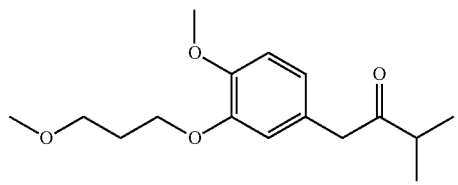 [SMILES: COCCCOc1cc(CC(=O)C(C)C)ccc1OC]

A mixture of 4-bromo-1-methoxy-2-(3-methoxypropoxy)benzene (20 g, 73 mmol), 3-methylbutan-2-one (19 g, 219 mmol, TCI), Pd$_2$(dba)$_3$ (1 g, 1.2 mmol), Xantphos (1.3 g, 2.4 mmol) and t-BuONa (23 g, 241 mol) in 500 mL of THF was stirred at 70° C. overnight. Then ethyl acetate and water were added. The separated organic phase was washed with brine, and then dried over anhydrous Na$_2$SO$_4$ and then concentrated. The residue was purified by column chromatography to give 1-[4-methoxy-3-(3-methoxypropoxy)phenyl]-3-methyl-butan-2-one (19 g).

Step 3: Preparation of 1-[4-methoxy-3-(3-methoxypropoxy)phenyl]-3-methyl-butan-2-amine

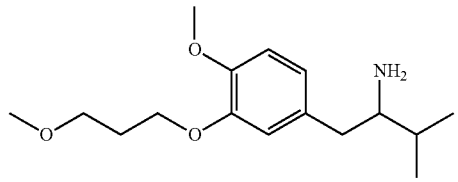 [SMILES: COCCCOc1cc(CC(N)C(C)C)ccc1OC]

1-[4-Methoxy-3-(3-methoxypropoxy)phenyl]-3-methyl-butan-2-one (19 g, 73 mmol) was dissolved in MeOH (150 mL). Then NH$_4$OAc (84 g, 1.1 mol) and NaBH$_3$CN (9.2 g, 146 mmol) were added. The mixture was stirred at room temperature overnight. 20% NaOH aqueous solution (100 mL) was added to the mixture. The reaction mixture was stirred for 20 minutes. The mixture was extracted with ethyl acetate, and the organic layer was dried over anhydrous Na$_2$SO$_4$ and then concentrated to afford 1-[4-methoxy-3-(3- methoxypropoxy)phenyl]-3-methyl-butan-2-amine (8 g) which was used in the next step without further purification.

Step 4: Preparation of N-[1-[[4-methoxy-3-(3-methoxypropoxy)phenyl]methyl]-2-methyl-propyl]formamide

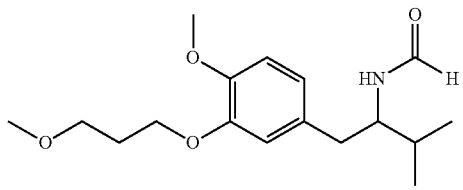 [SMILES: COCCCOc1cc(CC(NC=O)C(C)C)ccc1OC]

A mixture of 1-(4-methoxy-3-ethoxy-phenyl)butan-2-amine (73 mmol) and formic acid (40 mL) in dioxane (150 mL) was refluxed for 16 hours and then concentrated under reduced pressure to afford crude N-[1-[[4-methoxy-3-(3-methoxypropoxy)phenyl]methyl]-2-methyl-propyl]formamide which was used in the next step without purification.

Step 5: Preparation of 7-methoxy-3-isopropyl-6-(3-methoxypropoxy)-3,4-dihydroisoquinoline

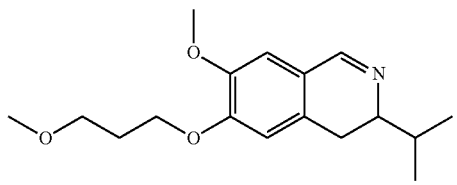 [SMILES: COCCCOc1cc2c(cc1OC)C=NC(C(C)C)C2]

To a solution of N-[1-[[4-methoxy-3-(3-methoxypropoxy)phenyl]methyl]-2-methyl-propyl]formamide (64.7 mmol) in acetonitrile (150 mL) was added POCl$_3$ (10.1 g, 64.7 mmol) dropwise at 0-5° C. The resultant mixture was refluxed for 4 hours and then concentrated. Ethyl acetate was added, followed by addition of ammonia water to adjust the pH of the aqueous solution to around 11. The aqueous layer was extracted with ethyl acetate. The organic layers were combined and then concentrated. The residue was purified by column chromatography to give 7-methoxy-3-isopropyl-6-(3-methoxypropoxy)-3,4-dihydroisoquinoline (16 g).

Step 6: Preparation of ethyl 10-methoxy-6-isopropyl-9-(3-methoxypropoxy)-2-oxo-1,6,7,11b-tetrahydrobenzo[a]quinolizine-3-carboxylate

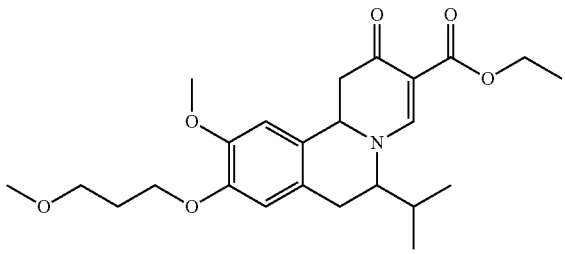 [SMILES: CCOC(=O)C1=CN2C(CC1=O)c1cc(OC)c(OCCCOC)cc1CC2C(C)C]

A mixture of 7-methoxy-3-isopropyl-6-(3-methoxypropoxy)-3,4-dihydroisoquinoline (16 g, 55 mmol) and ethyl 2-(ethoxymethylene)-3-oxo-butanoate (30 g, 165 mmol) in EtOH (150 mL) was stirred at 100° C. overnight. The mixture was concentrated to give crude ethyl 10-methoxy-6-isopropyl-9-(3-methoxypropoxy)-2-oxo-1,6,7,11b-tetrahydrobenzo[a]quinolizine-3-carboxylate as a dark brown oil which was used in the next step without purification.

Step 7: Preparation of ethyl 10-methoxy-6-isopropyl-9-(3-methoxypropoxy)-2-oxo-6,7-dihydrobenzo[a]quinolizine-3-carboxylate

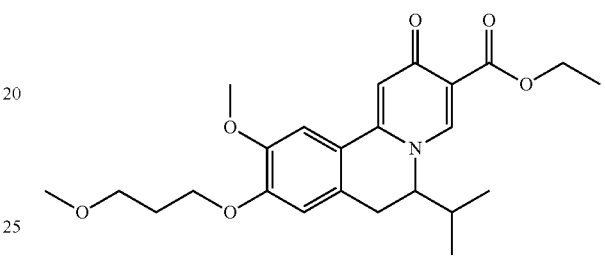

A mixture of crude ethyl 10-methoxy-6-isopropyl-9-(3-methoxypropoxy)-2-oxo-1,6,7,11b-tetrahydrobenzo[a]quinolizine-3-carboxylate (55 mmol) and p-chloranil (13.4 g, 55 mmol) in DME (100 mL) was refluxed for 2 hours. After being cooled to room temperature, the mixture was concentrated under vacuum to give crude ethyl 10-methoxy-6-isopropyl-9-(3-methoxypropoxy)-2-oxo-6,7-dihydrobenzo[a]quinolizine-3-carboxylate as a brown oil.

Step 8: Preparation of 10-methoxy-6-isopropyl-9-(3-methoxypropoxy)-2-oxo-6,7-dihydrobenzo[a]quinolizine-3-carboxylic Acid

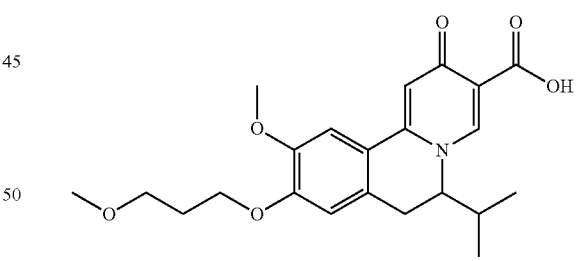

To a solution of crude ethyl 10-methoxy-6-isopropyl-9-(3-methoxypropoxy)-2-oxo-6,7-dihydrobenzo[a]quinolizine-3-carboxylate from Step 7 in EtOH (100 mL) was added 10% NaOH aqueous solution dropwise at room temperature. The resultant mixture was stirred for 2 hours, and then acidified to pH 1-2 with 2M hydrochloric acid. The mixture was extracted with DCM, and the combined organic layers were washed with brine, and then dried over anhydrous Na$_2$SO$_4$ and then concentrated. The residue was purified by column chromatography and recrystallization from EtOH/ethyl ether to afford 10-methoxy-6-isopropyl-9-(3-methoxypropoxy)-2-oxo-6,7-dihydrobenzo[a]quinolizine-3-carboxylic acid (8.7 g) as a white solid.

Step 9: Preparation of 6-isopropyl-10-methoxy-9-(3-methoxypropoxy)-2-oxo-N-(1H-tetrazol-5-yl)-6,7-dihydrobenzo[a]quinolizine-3-carboxamide

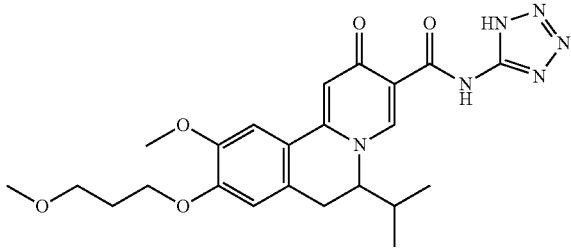 [SMILES: COCCCOc1cc2c(cc1OC)-c1cc(=O)c(C(=O)Nc3nnn[nH]3)cn1C(C(C)C)C2]

To a solution of 6-isopropyl-10-methoxy-9-(3-methoxypropoxy)-2-oxo-6,7-dihydrobenzo[a]quinolizine-3-carboxylic acid (30 mg, 0.075 mmol) in DMF (2 mL) was added HATU (42.6 mg, 0.11 mmol) and Et$_3$N (21.0 μL, 0.14 mmol), the reaction was stirred for 5 minutes at room temperature, then 1H-tetrazol-5-amine (12.3 mg, 0.15 mmol) was added to the solution. The reaction mixture was stirred for 4 hours and then purified by preparative HPLC to give 6-isopropyl-10-methoxy-9-(3-methoxypropoxy)-2-oxo-N-(1H-tetrazol-5-yl)-6,7-dihydrobenzo[a]quinolizine-3-carboxamide (7 mg). $^1$H NMR (400 MHz, DMSO) δ8.77 (s, 1H), 7.50 (s, 1H), 7.34 (s, 1H), 7.08 (s, 1H), 4.48-4.40 (m, 1H), 4.16-4.02 (m, 2H), 3.88 (s, 3H), 3.48 (t, J=6.3 Hz, 2H), 3.30-3.23 (m, 4H), 1.99 (quin, J=6.3 Hz, 2H), 1.69-1.57 (m, 1H), 0.89 (d, J=6.5 Hz, 3H), 0.72 (d, J=6.5 Hz, 3H). MS obsd. (ESI$^+$) [(M+H)$^+$]: 469.

Example 37: 10-chloro-6-isopropyl-9-(3-methoxypropoxy)-2-oxo-N-(1H-tetrazol-5-yl)-6,7-dihydrobenzo[a]quinolizine-3-carboxamide

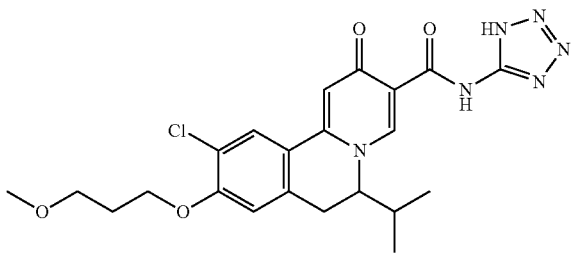 [SMILES: COCCCOc1cc2c(cc1Cl)-c1cc(=O)c(C(=O)Nc3nnn[nH]3)cn1C(C(C)C)C2]

Step 1: Preparation of 4-bromo-1-chloro-2-(3-methoxypropoxy)benzene

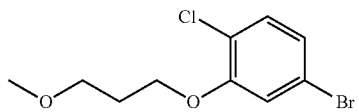

A 250 mL round-bottomed flask was charged with 5-bromo-2-chloro-phenol (22 g, 106 mmol, Bepharm Ltd), 1-bromo-3-methoxy-propane (19.5 g, 127 mmol), K$_2$CO$_3$ (30 g, 212 mmol) and DMF (50 mL). The resultant mixture was stirred at 50° C. for 3 hours, then ethyl acetate and water were added. The organic phase was separated, and then dried over anhydrous Na$_2$SO$_4$ and then concentrated to give 4-bromo-1-chloro-2-(3-methoxypropoxy)benzene (30 g).

Step 2: Preparation of 1-[4-chloro-3-(3-methoxypropoxy)phenyl]-3-methyl-butan-2-one

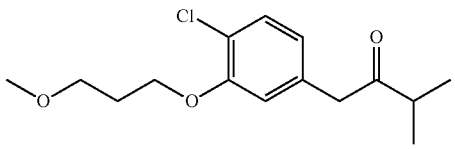 [SMILES: COCCCOc1cc(CC(=O)C(C)C)ccc1Cl]

A mixture of 4-bromo-1-chloro-2-(3-methoxypropoxy)benzene (28 g, 0.1 mol), 3-methylbutan-2-one (26 g, 0.3 mol), Pd$_2$(dba)$_3$ (1.4 g, 1.5 mmol), Xantphos (1.8 g, 3 mmol) and t-BuONa (32 g, 0.33 mol) in 500 mL of THF was stirred at 70° C. overnight. Then ethyl acetate and water were added. The separated organic phase was washed with brine, and then dried over anhydrous Na$_2$SO$_4$ and then concentrated. The residue was purified by column chromatography to give 1-[4-chloro-3-(3-methoxypropoxy)phenyl]-3-methyl-butan-2-one (19.6 g).

Step 3: Preparation of 1-[4-chloro-3-(3-methoxypropoxy)phenyl]-3-methyl-butan-2-amine

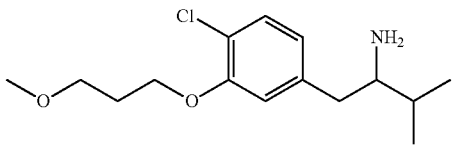 [SMILES: COCCCOc1cc(CC(N)C(C)C)ccc1Cl]

1-[4-Chloro-3-(3-methoxypropoxy)phenyl]-3-methyl-butan-2-one (10 g, 35 mmol) was dissolved in MeOH (100 mL). Then NH$_4$OAc (40 g, 525 mmol) and NaBH$_3$CN (4.4 g, 70 mmol) were added. The mixture was stirred at room temperature overnight. Then 20% NaOH aqueous solution (50 mL) was added, and the mixture was stirred for 20 minutes. The mixture was extracted with ethyl acetate, and the organic layer was dried over anhydrous Na$_2$SO$_4$ and then concentrated to afford 1-[4-chloro-3-(3-methoxypropoxy)phenyl]-3-methyl-butan-2-amine (8 g) which was used in the next step without further purification.

Step 4: Preparation of N-[1-[[4-chloro-3-(3-methoxypropoxy)phenyl]methyl]-2-methyl-propyl]formamide

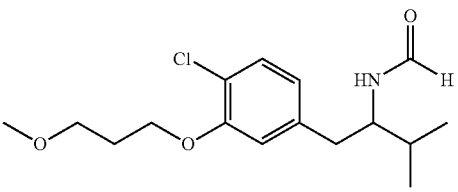 [SMILES: COCCCOc1cc(CC(NC=O)C(C)C)ccc1Cl]

A mixture of 1-(4-chloro-3-ethoxy-phenyl)butan-2-amine (35 mmol) and formic acid (20 mL) in dioxane (100 mL) was refluxed for 16 hours and then concentrated under reduced pressure to afford the crude N-[1-[[4-chloro-3-(3-methoxypropoxy)phenyl]methyl]-2-methyl-propyl]formamide which was used in the next step without purification.

Step 5: Preparation of 7-chloro-3-isopropyl-6-(3-methoxypropoxy)-3,4-dihydroisoquinoline

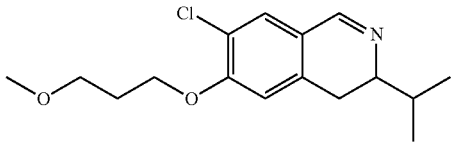 [SMILES: COCCCOc1cc2c(cc1Cl)C=NC(C(C)C)C2]

To a solution of N-[1-[[4-chloro-3-(3-methoxypropoxy)phenyl]methyl]-2-methyl-propyl]formamide (7.6 g, 24 mmol) in acetonitrile (100 mL) was added $POCl_3$ (3.8 g, 24 mmol) dropwise at 0-5° C. The resultant mixture was refluxed for 4 hours and then concentrated. Ethyl acetate was added, and then ammonia was added to the mixture to adjust the pH of the aqueous solution to around 11. The aqueous layer was extracted with ethyl acetate. The organic layers were combined and then concentrated. The residue was purified by column chromatography to give 7-chloro-3-isopropyl-6-(3-methoxypropoxy)-3,4-dihydroisoquinoline (4.6 g).

Step 6: Preparation of ethyl 10-chloro-6-isopropyl-9-(3-methoxypropoxy)-2-oxo-1,6,7,11b-tetrahydrobenzo[a]quinolizine-3-carboxylate

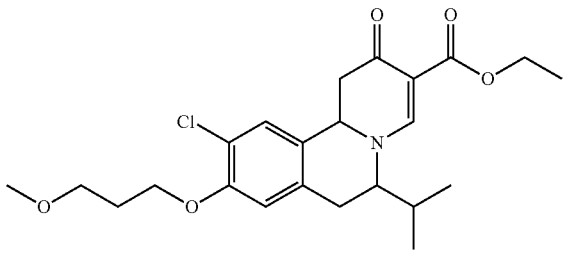 [SMILES: CCOC(=O)C1=CN2C(CC1=O)c1cc(Cl)c(OCCCOC)cc1CC2C(C)C]

A mixture of 7-chloro-3-isopropyl-6-(3-methoxypropoxy)-3,4-dihydroisoquinoline (4.6 g, 15 mmol) and ethyl 2-(ethoxymethylene)-3-oxo-butanoate (8.3 g, 45 mmol) in EtOH (20 mL) was stirred at 110° C. overnight. The mixture was concentrated to give crude ethyl 10-chloro-6-isopropyl-9-(3-methoxypropoxy)-2-oxo-1,6,7,11b-tetrahydrobenzo[a]quinolizine-3-carboxylate as a dark brown oil which was used in the next step without purification.

Step 7: Preparation of ethyl 10-chloro-6-isopropyl-9-(3-methoxypropoxy)-2-oxo-6,7-dihydrobenzo[a]quinolizine-3-carboxylate

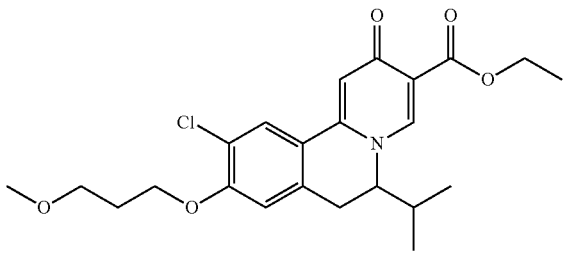 [SMILES: CCOC(=O)c1cn2c(cc1=O)-c1cc(Cl)c(OCCCOC)cc1CC2C(C)C]

A mixture of crude ethyl 10-chloro-6-isopropyl-9-(3-methoxypropoxy)-2-oxo-1,6,7,11b-tetrahydrobenzo[a]quinolizine-3-carboxylate (15 mmol) and p-chloranil (3.6 g, 15 mmol) in DME (20 mL) was refluxed for 2 hours. After being cooled to room temperature, the mixture was concentrated under vacuum to give crude ethyl 10-chloro-6-isopropyl-9-(3-methoxypropoxy)-2-oxo-6,7-dihydrobenzo[a]quinolizine-3-carboxylate as a brown oil.

Step 8: Preparation of 10-chloro-6-isopropyl-9-(3-methoxypropoxy)-2-oxo-6,7-dihydrobenzo[a]quinolizine-3-carboxylic Acid

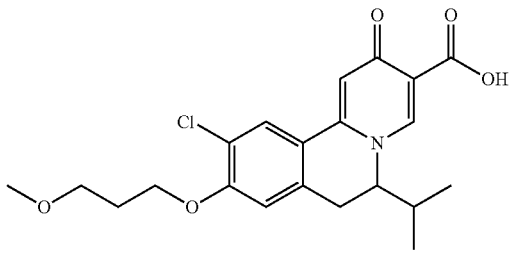 [SMILES: COCCCOc1cc2c(cc1Cl)-c1cc(=O)c(C(=O)O)cn1C(C(C)C)C2]

To a solution of crude ethyl 10-chloro-6-isopropyl-9-(3-methoxypropoxy)-2-oxo-6,7-dihydrobenzo[a]quinolizine-3-carboxylate from Step 7 in EtOH (50 mL) was added 10% NaOH aqueous solution dropwise at room temperature. The resultant mixture was stirred for 2 hours, and then acidified to pH 1-2 with 2M hydrochloric acid. The mixture was extracted with DCM, and the combined organic layers were washed with brine, and then dried over anhydrous $Na_2SO_4$ and then concentrated. The residue was purified by column chromatography and recrystallization from EtOH/ethyl ether to afford 10-chloro-6-isopropyl-9-(3-methoxypropoxy)-2-oxo-6,7-dihydrobenzo[a]quinolizine-3-carboxylic acid (1.7 g) as a white solid.

Step 9: Preparation of 10-chloro-6-isopropyl-9-(3-methoxypropoxy)-2-oxo-N-(1H-tetrazol-5-yl)-6,7-dihydrobenzo[a]quinolizine-3-carboxamide

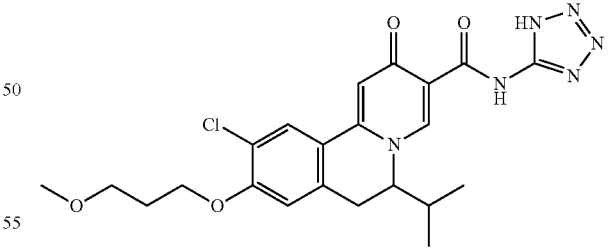

To a solution of 10-chloro-6-isopropyl-9-(3-methoxypropoxy)-2-oxo-6,7-dihydrobenzo[a]quinolizine-3-carboxylic acid (30 mg, 0.074 mmol) in DMF (2 mL) was added HATU (42.1 mg, 0.11 mmol) and $Et_3N$ (20.7 μL, 0.15 mmol). The reaction was stirred for 5 minutes at room temperature, then 1H-tetrazol-5-amine (12.6 mg, 0.15 mmol) was added. The reaction mixture was stirred for 4 hours and then purified by preparative HPLC to give 10-chloro-6-isopropyl-9-(3-methoxypropoxy)-2-oxo-N-(1H-tetrazol-5-yl)-6,7-dihydrobenzo[a]quinolizine-3-carboxamide (7 mg). ¹H NMR (400 MHz, DMSO) δ=8.80 (s, 1H), 8.17 (s, 1H), 7.32 (s, 1H), 7.31 (s, 1H), 4.54-4.47 (m, 1H), 4.29-4.14 (m, 2H), 3.52 (t, J=6.3 Hz, 2H), 3.40-3.34 (m, 1H), 3.28-3.23 (m, 4H), 2.03 (m, 2H), 1.67-1.55 (m, 1H), 0.90 (d, J=6.5 Hz, 3H), 0.74 (d, J=6.8 Hz, 3H). MS obsd. (ESI⁺) [(M+H)⁺]: 473.

Example 38: (+)-10-chloro-6-isopropyl-9-(3-methoxypropoxy)-2-oxo-N-(1H-tetrazol-5-yl)-6,7-dihydrobenzo[a]quinolizine-3-carboxamide

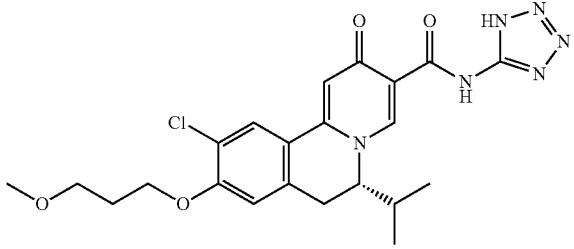 [SMILES: COCCCOc1cc2c(cc1Cl)-c1cc(=O)c(C(=O)Nc3nnn[nH]3)cn1[C@H](C(C)C)C2]

Step 1: (+)-10-chloro-6-isopropyl-9-(3-methoxy-propoxy)-2-oxo-6,7-dihydrobenzo[a]quinolizine-3-carboxylic Acid

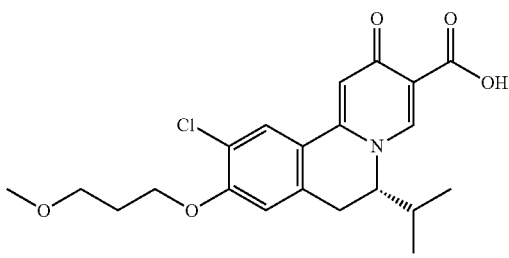 [SMILES: COCCCOc1cc2c(cc1Cl)-c1cc(=O)c(C(=O)O)cn1[C@H](C(C)C)C2]

Separation of the racemic 10-chloro-6-isopropyl-9-(3-methoxypropoxy)-2-oxo-6,7-dihydrobenzo[a]quinolizine-3-carboxylic acid (1.3 g) by chiral HPLC afforded (+)-10-chloro-6-isopropyl-9-(3-methoxypropoxy)-2-oxo-6,7-dihydrobenzo[a]quinolizine-3-carboxylic acid (465 mg). $[\alpha]_D^{20}$=+118.44° (0.103%, MeOH)

Step 2: Preparation of (+)-10-chloro-6-isopropyl-9-(3-methoxypropoxy)-2-oxo-N-(1H-tetrazol-5-yl)-6,7-dihydrobenzo[a]quinolizine-3-carboxamide

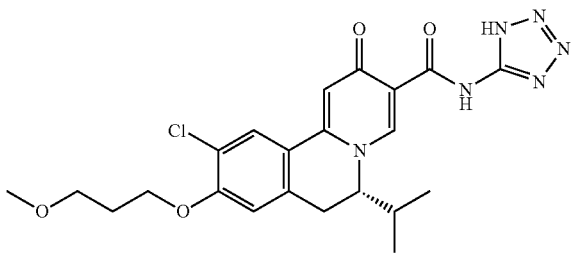 [SMILES: COCCCOc1cc2c(cc1Cl)-c1cc(=O)c(C(=O)Nc3nnn[nH]3)cn1[C@H](C(C)C)C2]

To a solution of (+)-10-chloro-6-isopropyl-9-(3-methoxypropoxy)-2-oxo-6,7-dihydrobenzo[a]quinolizine-3-carboxylic acid (30 mg, 0.074 mmol) in DMF (2 mL) was added HATU (42.1 mg, 0.11 mmol) and Et₃N (20.7 μL, 0.15 mmol). The reaction was stirred for 5 minutes at room temperature, then 1H-tetrazol-5-amine (12.6 mg, 0.15 mmol) was added. The reaction mixture was stirred for 4 hours and then purified by preparative HPLC to give (+)-10-chloro-6-isopropyl-9-(3-methoxypropoxy)-2-oxo-N-(1H-tetrazol-5-yl)-6,7-dihydrobenzo[a]quinolizine-3-carboxamide (7 mg). ¹H NMR (400 MHz, MeOD) δ=8.75 (s, 1H), 7.93 (s, 1H), 7.74 (s, 1H), 7.08 (s, 1H), 4.28-4.20 (m, 3H), 3.68-3.62 (m, 2H), 3.44-3.37 (m, 4H), 3.32-3.26 (m, 1H), 2.18-2.10 (m, 2H), 1.85-1.75 (m, 1H), 1.00 (d, J=6.5 Hz, 3H), 0.84 (d, J=6.8 Hz, 3H). MS obsd. (ESI⁺) [(M+H)⁺]: 473. $[\alpha]_D^{20}$=+87.20° (0.15%, DMSO).

BIOLOGICAL EXAMPLES

Example 39: Materials and Methods

HBV Cell Line

HepG2.2.15 cells (Acs et al. *Proc Natl Acad Sci USA*, 84, (1987), 4641-4), a constitutively HBV-expressing cell line were cultured in DMEM+Glutamax-I medium (Invitrogen, Carlsbad, Calif., USA), supplemented with 10% fetal bovine serum (Invitrogen) and G418 (Invitrogen) at a final concentration of 200 mg/L and maintained in 5% CO₂ at 37° C.

HBsAg Assay

HepG2.2.15 cells were seeded in duplicate into white, 96-well plates at 1.5×10⁴ cells/well. The cells were treated with a three-fold serial dilution series of the compounds in DMSO. The final DMSO concentration in all wells was 1% and DMSO was used as no drug control.

The HBsAg chemiluminescence immunoassay (CLIA) kit (Autobio Diagnostics Co., Zhengzhou, China, Catalog number: CL0310-2) was used to measure the levels of secreted HBV antigens semi-quantitatively. For the detection 50 μL/well culture supernatant was used and HBsAg was quantified using HBsAg chemiluminescence immunoassay (CLIA) kit (Autobio Diagnostics Co., Zhengzhou, China, Catalog number: CL0310-2), 50 μl of the supernatant was transferred to the CLIA assay plate and 50 μL of enzyme conjugate reagent was added into each well. The plates were sealed and gently agitated for 1 hour at room temperature. The supernatant-enzyme-mixture was discarded and wells were washed 6 times with 300 μL of PBS. The residual liquid was removed by plating the CLIA plate right side down on absorbent tissue paper. 25 μL of substrates A and B were added to each well. Luminance was measured using a luminometer (Mithras LB 940 Multimode Microplate Reader) after 10 minutes incubation. Dose-response curves were generated and the IC₅₀ value was extrapolated by using the E-WorkBook Suite (ID Business Solutions Ltd., Guildford, UK). The IC₅₀ was defined as the compound concentration (or conditioned media log dilution) at which HBsAg secretion was reduced by 50% compared to the no drug control.

The compounds of the present invention were tested for their capacity to inhibit HBsAg as described herein. The Examples were tested in the above assay and found to have IC₅₀ below 50.0 μM. Particular compounds of formula I were found to have IC₅₀ below 5.0 μM. Results of HBsAg assay are given in Table 1.

TABLE 1

Activity data of particular compounds

| Example No. | IC$_{50}$ (μM) |
|---|---|
| 1 | 26.2 |
| 2 | 19 |
| 3 | 31 |
| 4 | 0.92 |
| 5 | 5.6 |
| 6 | 43 |
| 7 | 7.8 |
| 8 | 33.7 |
| 9 | 5.4 |
| 10 | 20.3 |
| 11 | 23.9 |
| 12 | 12.8 |
| 13 | 36.6 |
| 14 | 1.1 |
| 15 | 26.7 |
| 16 | 18.4 |
| 17 | 2.2 |
| 18 | 4.9 |
| 19 | 8 |
| 20 | 22.3 |
| 21 | 19.4 |
| 22 | 43.2 |
| 23 | 17.3 |
| 24 | 12.6 |
| 25 | 16.4 |
| 26 | 16.2 |
| 27 | 15.8 |
| 28 | 3.7 |
| 29 | 1.5 |
| 30 | 16.9 |
| 31 | 44.1 |
| 32 | 0.38 |
| 33 | 1 |
| 34 | 18.3 |
| 35 | 12.9 |
| 36 | 5.5 |
| 37 | 5.9 |
| 38 | 2.3 |

The invention claimed is:
1. A compound of formula (I)

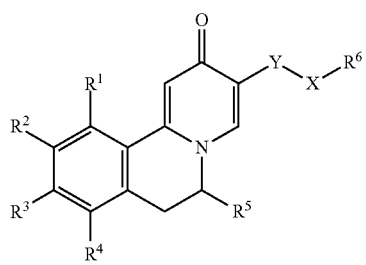

wherein
X is oxygen or N—R$^7$;
Y is CH$_2$ or C(O);
R$^1$ is hydrogen, halogen, C$_{1-6}$alkyl, or C$_{1-6}$alkoxy;
R$^2$ is hydrogen; halogen; C$_{1-6}$alkyl, which is unsubstituted or once or more times substituted by fluoro; or C$_{1-6}$alkoxy;
R$^3$ is C$_{1-6}$alkyl, which is unsubstituted or once or more times substituted by fluoro; cyano; morpholinyl; or R$^8$—O—, wherein R$^8$ is C$_{1-6}$alkyl, which is unsubstituted or substituted by one or more substituents each independently selected from fluoro, C$_{1-6}$alkoxy, C$_{1-6}$alkylsulfonyl, cyano, C$_{3-7}$cycloalkyl, C$_{1-6}$alkylamino, diC$_{1-6}$alkylamino, hydroxy, phenyl, pyrrolidinyl and tetrahydropyranyl;
R$^4$ is hydrogen, halogen or C$_{1-6}$alkyl;
R$^5$ is hydrogen; C$_{1-6}$alkyl, which is unsubstituted or once or more times substituted by fluoro; C$_{1-6}$alkoxy; C$_{3-7}$cycloalkyl; or C$_{3-7}$cycloalkyl-C$_xH_{2x}$—;
R$^6$ is hydrogen; C$_{1-6}$alkylsulfonyl; hydroxyl; 1H-tetrazol-5-yl; or C$_{1-6}$alkyl, which is unsubstituted or substituted by one or more substituents each independently selected from fluoro, C$_{3-7}$cycloalkyl, carboxyl-C$_xH_{2x}$—, phenyl, hydroxy, C$_{1-6}$alkoxy, amino, C$_{1-6}$alkylamino and diC$_{1-6}$alkylamino; and
R$^7$ is hydrogen or C$_{1-6}$alkyl;
or R$^6$ and R$^7$, together with the nitrogen to which they are attached, form pyrrolidinyl, piperidinyl, or morpholinyl, each of which is unsubstituted or once or two times substituted by carboxyl;
or a pharmaceutically acceptable salt, enantiomer or diastereomer thereof.

2. A compound of formula I according to claim 1, wherein
X is oxygen or N—R$^7$;
Y is CH$_2$ or C(O);
R$^1$ is hydrogen or halogen;
R$^2$ is hydrogen, halogen or C$_{1-6}$alkoxy;
R$^3$ is R$^8$—O—, wherein R$^8$ is C$_{1-6}$alkyl, which is unsubstituted or substituted by one or two substituents each independently selected from C$_{1-6}$alkoxy, C$_{3-7}$cycloalkyl and phenyl;
R$^4$ is hydrogen;
R$^5$ is C$_{1-6}$alkyl, which is unsubstituted or once or two times substituted by trifluoromethyl; or C$_{3-7}$cycloalkyl;
R$^6$ is hydrogen; C$_{1-6}$alkyl, which is unsubstituted or substituted by one or two substituents each independently selected from phenyl, hydroxy, C$_{1-6}$alkoxy, carboxy, and diC$_{1-6}$alkylamino; hydroxy; 1H-tetrazol-5-yl; or C$_{1-6}$alkylsulfonyl; and
R$^7$ is hydrogen or C$_{1-6}$alkyl;
or R$^6$ and R$^7$, together with the nitrogen to which they are attached, form pyrrolidinyl, piperidinyl, or morpholinyl, each of which is unsubstituted or once or two times substituted by carboxyl;
or a pharmaceutically acceptable salt, enantiomer or diastereomer thereof.

3. A compound of formula I according to claim 2, wherein
X is oxygen or N—R$^7$;
Y is CH$_2$ or C(O);
R$^1$ is hydrogen or chloro;
R$^2$ is hydrogen, methoxy or chloro;
R$^3$ is R$^8$—O—, wherein R$^8$ is methyl, ethyl, propyl or isobutyl, each of which is unsubstituted or substituted by one or two substituents each independently selected from methoxy, cyclopropyl and phenyl;
R$^4$ is hydrogen;
R$^5$ is ethyl, isopropyl, trifluoromethylmethyl, tert-butyl or cyclobutyl;
R$^6$ is hydrogen; methyl, ethyl, propyl, isopropyl or isobutyl, each of which is unsubstituted or substituted by one or two substituents each independently selected from phenyl, hydroxy, methoxy, carboxy, and dimethylamino; hydroxy; 1H-tetrazol-5-yl; or methylsulfonyl; and
R$^7$ is hydrogen or methyl;
or R$^6$ and R$^7$, together with the nitrogen to which they are attached, form pyrrolidinyl, piperidinyl, or morpholinyl, each of which is unsubstituted or once or two times substituted by carboxyl;

or a pharmaceutically acceptable salt, enantiomer or diastereomer thereof.

4. A compound of formula I according to claim 1, wherein $R^1$ is hydrogen; or a pharmaceutically acceptable salt, enantiomer or diastereomer thereof.

5. A compound of formula I according to claim 1, wherein $R^2$ is $C_{1-6}$alkoxy or halogen; or a pharmaceutically acceptable salt, enantiomer or diastereomer thereof.

6. A compound of formula I according to claim 1, wherein $R^2$ is methoxy or chloro; or a pharmaceutically acceptable salt, enantiomer or diastereomer thereof.

7. A compound of formula I according to claim 1, wherein $R^3$ is $R^8$—O—, wherein $R^8$ is $C_{1-6}$alkyl, which is unsubstituted or substituted by one or two substituents each independently selected from $C_{1-6}$alkoxy and phenyl; or a pharmaceutically acceptable salt, enantiomer or diastereomer thereof.

8. A compound of formula I according to claim 1, wherein $R^3$ is $R^8$—O—, wherein $R^8$ is methyl or propyl, each of which is unsubstituted or substituted by one or two substituents each independently selected from methoxy and phenyl; or a pharmaceutically acceptable salt, enantiomer or diastereomer thereof.

9. A compound of formula I according to claim 1, wherein $R^5$ is $C_{1-6}$alkyl, which is unsubstituted or once or two times substituted by fluoro; or $C_{3-7}$cycloalkyl; or a pharmaceutically acceptable salt, enantiomer or diastereomer thereof.

10. A compound of formula I according to claim 1, wherein $R^5$ is ethyl or isopropyl; or a pharmaceutically acceptable salt, enantiomer or diastereomer thereof.

11. A compound of formula I according to claim 1, wherein $R^6$ is hydrogen; methyl, ethyl, propyl, isopropyl or isobutyl, each of which is unsubstituted or substituted by one or two substituents each independently selected from phenyl, hydroxy, methoxy, carboxy, and dimethylamino; hydroxy; 1H-tetrazol-5-yl; or methylsulfonyl; or a pharmaceutically acceptable salt, enantiomer or diastereomer thereof.

12. A compound of formula I according to claim 1, wherein $R^6$ and $R^7$, together with the nitrogen to which they are attached, form pyrrolidinyl, piperidinyl, morpholinyl, each of which is unsubstituted or once or two times substituted by carboxyl; or a pharmaceutically acceptable salt, enantiomer or diastereomer thereof.

13. A compound according to claim 1, wherein
X is oxygen, NH or N($C_{1-6}$alkyl);
Y is $CH_2$ or C(O);
$R^1$ is hydrogen;
$R^2$ is $C_{1-6}$alkoxy or halogen;
$R^3$ is $R^8$—O—, wherein $R^8$ is $C_{1-6}$alkyl, which is unsubstituted or once substituted by phenyl or $C_{1-6}$alkoxy;
$R^4$ is hydrogen;
$R^5$ is $C_{1-6}$alkyl or $C_{3-7}$cycloalkyl;
$R^6$ is $C_{1-6}$alkylsulfonyl; 1H-tetrazol-5-yl; or $C_{1-6}$alkyl, which is unsubstituted or once substituted by $C_{1-6}$alkoxy;
or a pharmaceutically acceptable salt, enantiomer, or diastereomer thereof.

14. A compound according to claim 1, wherein
X is oxygen, NH or N($CH_3$);
Y is $CH_2$ or C(O);
$R^1$ is hydrogen;
$R^2$ is methoxy or chloro;
$R^3$ is $R^8$—O—, wherein $R^8$ is methyl, ethyl, propyl or isobutyl, each of which is unsubstituted or once substituted by phenyl or methoxy;
$R^4$ is hydrogen;

$R^5$ is ethyl, isopropyl, tert-butyl or cyclobutyl; and
$R^6$ is methylsulfonyl; 1H-tetrazol-5-yl; methyl; or isopropyl, which is once substituted by methoxy;
or a pharmaceutically acceptable salt, enantiomer, or diastereomer thereof.

15. A compound of formula I according to claim 1, selected from the group consisting of
N-benzyl-9-benzyloxy-6-ethyl-10-methoxy-2-oxo-6,7-dihydrobenzo[a]quinolizine-3-carboxamide;
9-benzyloxy-6-ethyl-10-methoxy-N-methyl-2-oxo-6,7-dihydrobenzo[a]quinolizine-3-carboxamide;
9-benzyloxy-6-ethyl-10-methoxy-N-(2-methoxy-1-methyl-ethyl)-2-oxo-6,7-dihydrobenzo[a]quinolizine-3-carboxamide;
9-benzyloxy-6-ethyl-10-methoxy-N-methylsulfonyl-2-oxo-6,7-dihydrobenzo[a]quinolizine-3-carboxamide;
9-benzyloxy-6-ethyl-10-methoxy-2-oxo-N-propyl-6,7-dihydrobenzo[a]quinolizine-3-carboxamide;
9-benzyloxy-6-ethyl-N-(2-hydroxyethyl)-10-methoxy-2-oxo-6,7-dihydrobenzo[a]quinolizine-3-carboxamide;
9-benzyloxy-6-ethyl-N-(2-hydroxy-1-methyl-ethyl)-10-methoxy-2-oxo-6,7-dihydrobenzo[a]quinolizine-3-carboxamide;
9-benzyloxy-N-[2-(dimethylamino)ethyl]-6-ethyl-10-methoxy-2-oxo-6,7-dihydrobenzo[a]quinolizine-3-carboxamide;
9-benzyloxy-6-ethyl-10-methoxy-2-oxo-N-sec-butyl-6,7-dihydrobenzo[a]quinolizine-3-carboxamide;
9-benzyloxy-6-ethyl-10-methoxy-2-oxo-6,7-dihydrobenzo[a]quinolizine-3-carbohydroxamic acid;
9-benzyloxy-N-[2-(dimethylamino)-1-methyl-ethyl]-6-ethyl-10-methoxy-2-oxo-6,7-dihydrobenzo[a]quinolizine-3-carboxamide;
9-benzyloxy-6-ethyl-10-methoxy-N-(2-methoxyethyl)-2-oxo-6,7-dihydrobenzo[a]quinolizine-3-carboxamide;
4-[6-ethyl-10-methoxy-9-(3-methoxypropoxy)-2-oxo-6,7-dihydrobenzo[a]quinolizine-3-carbonyl]morpholine-2-carboxylic acid;
6-ethyl-10-methoxy-9-(3-methoxypropoxy)-2-oxo-N-(1H-tetrazol-5-yl)-6,7-dihydrobenzo[a]quinolizine-3-carboxamide;
N-benzyl-6-ethyl-10-methoxy-9-(3-methoxypropoxy)-2-oxo-6,7-dihydrobenzo[a]quinolizine-3-carboxamide;
6-ethyl-10-methoxy-N-(2-methoxy-1-methyl-ethyl)-9-(3-methoxypropoxy)-2-oxo-6,7-dihydrobenzo[a]quinolizine-3-carboxamide;
9-ethoxy-6-ethyl-10-methoxy-N-(2-methoxy-1-methyl-ethyl)-2-oxo-6,7-dihydrobenzo[a]quinolizine-3-carboxamide;
6-ethyl-9-isobutoxy-10-methoxy-N-(2-methoxy-1-methyl-ethyl)-2-oxo-6,7-dihydrobenzo[a]quinolizine-3-carboxamide;
9-(cyclopropylmethoxy)-6-ethyl-10-methoxy-N-(2-methoxy-1-methyl-ethyl)-2-oxo-6,7-dihydrobenzo[a]quinolizine-3-carboxamide;
6-ethyl-3-(hydroxymethyl)-10-methoxy-9-(3-methoxypropoxy)-6,7-dihydrobenzo[a]quinolizin-2-one;
4-[[6-ethyl-10-methoxy-9-(3-methoxypropoxy)-2-oxo-6,7-dihydrobenzo[a]quinolizin-3-yl]methyl]morpholine-3-carboxylic acid;
1-[[6-ethyl-10-methoxy-9-(3-methoxypropoxy)-2-oxo-6,7-dihydrobenzo[a]quinolizin-3-yl]methyl]piperidine-2-carboxylic acid;
1-[[6-ethyl-10-methoxy-9-(3-methoxypropoxy)-2-oxo-6,7-dihydrobenzo[a]quinolizin-3-yl]methyl]pyrrolidine-2-carboxylic acid;

6-ethyl-10-methoxy-9-(3-methoxypropoxy)-3-(1-piperidylmethyl)-6,7-dihydrobenzo[a]quinolizin-2-one;
6-ethyl-10-methoxy-9-(3-methoxypropoxy)-3-(pyrrolidin-1-ylmethyl)-6,7-dihydrobenzo[a]quinolizin-2-one;
6-ethyl-10-methoxy-9-(3-methoxypropoxy)-3-(morpholinomethyl)-6,7-dihydrobenzo[a]quinolizin-2-one;
6-ethyl-10-methoxy-9-(3-methoxypropoxy)-3-(methylaminomethyl)-6,7-dihydrobenzo[a]quinolizin-2-one;
3-[(dimethylamino)methyl]-6-ethyl-10-methoxy-9-(3-methoxypropoxy)-6,7-dihydrobenzo[a]quinolizin-2-one;
6-ethyl-10-methoxy-3-(methoxymethyl)-9-(3-methoxypropoxy)-6,7-dihydrobenzo[a]quinolizin-2-one;
6-cyclobutyl-10-methoxy-9-(3-methoxypropoxy)-2-oxo-N-(1H-tetrazol-5-yl)-6,7-dihydrobenzo[a]quinolizine-3-carboxamide;
(6R)-6-ethyl-9,10-dimethoxy-2-oxo-N-(1H-tetrazol-5-yl)-6,7-dihydrobenzo[a]quinolizine-3-carboxamide;
6-tert-butyl-10-methoxy-9-(3-methoxypropoxy)-2-oxo-N-(1H-tetrazol-5-yl)-6,7-dihydrobenzo[a]quinolizine-3-carboxamide;
6-cyclobutyl-10-methoxy-9-(3-methoxypropoxy)-2-oxo-N-(1H-tetrazol-5-yl)-6,7-dihydrobenzo[a]quinolizine-3-carboxamide;
11-chloro-6-isopropyl-9-(2-methoxyethoxy)-2-oxo-N-(1H-tetrazol-5-yl)-6,7-dihydrobenzo[a]quinolizine-3-carboxamide;
9,10-dimethoxy-2-oxo-N-(1H-tetrazol-5-yl)-6-(2,2,2-trifluoroethyl)-6,7-dihydrobenzo[a]quinolizine-3-carboxamide;
6-isopropyl-10-methoxy-9-(3-methoxypropoxy)-2-oxo-N-(1H-tetrazol-5-yl)-6,7-dihydrobenzo[a]quinolizine-3-carboxamide;
10-chloro-6-isopropyl-9-(3-methoxypropoxy)-2-oxo-N-(1H-tetrazol-5-yl)-6,7-dihydrobenzo[a]quinolizine-3-carboxamide; and
(+)-10-chloro-6-isopropyl-9-(3-methoxypropoxy)-2-oxo-N-(1H-tetrazol-5-yl)-6,7-dihydrobenzo[a]quinolizine-3-carboxamide;
or a pharmaceutically acceptable salt thereof.

16. A compound of formula I according to claim 1, selected from the group consisting of
9-benzyloxy-6-ethyl-10-methoxy-N-methylsulfonyl-2-oxo-6,7-dihydrobenzo[a]quinolizine-3-carboxamide;
6-ethyl-10-methoxy-9-(3-methoxypropoxy)-2-oxo-N-(1H-tetrazol-5-yl)-6,7-dihydrobenzo[a]quinolizine-3-carboxamide;
9-ethoxy-6-ethyl-10-methoxy-N-(2-methoxy-1-methylethyl)-2-oxo-6,7-dihydrobenzo[a]quinolizine-3-carboxamide;
6-ethyl-9-isobutoxy-10-methoxy-N-(2-methoxy-1-methyl-ethyl)-2-oxo-6,7-dihydrobenzo[a]quinolizine-3-carboxamide;
3-[(dimethylamino)methyl]-6-ethyl-10-methoxy-9-(3-methoxypropoxy)-6,7-dihydrobenzo[a]quinolizin-2-one;
6-ethyl-10-methoxy-3-(methoxymethyl)-9-(3-methoxypropoxy)-6,7-dihydrobenzo[a]quinolizin-2-one;
6-tert-butyl-10-methoxy-9-(3-methoxypropoxy)-2-oxo-N-(1H-tetrazol-5-yl)-6,7-dihydrobenzo[a]quinolizine-3-carboxamide;
6-cyclobutyl-10-methoxy-9-(3-methoxypropoxy)-2-oxo-N-(1H-tetrazol-5-yl)-6,7-dihydrobenzo[a]quinolizine-3-carboxamide;
10-chloro-6-isopropyl-9-(3-methoxypropoxy)-2-oxo-N-(1H-tetrazol-5-yl)-6,7-dihydrobenzo[a]quinolizine-3-carboxamide; and
(+)-10-chloro-6-isopropyl-9-(3-methoxypropoxy)-2-oxo-N-(1H-tetrazol-5-yl)-6,7-dihydrobenzo[a]quinolizine-3-carboxamide;
or a pharmaceutically acceptable salt thereof.

* * * * *